US012216404B2

(12) United States Patent
Kojima et al.

(10) Patent No.: US 12,216,404 B2
(45) Date of Patent: Feb. 4, 2025

(54) ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

(71) Applicant: FUJIFILM Corporation, Tokyo (JP)

(72) Inventors: Masafumi Kojima, Shizuoka (JP); Minoru Uemura, Shizuoka (JP); Takashi Kawashima, Shizuoka (JP); Akiyoshi Goto, Shizuoka (JP); Kei Yamamoto, Shizuoka (JP); Kazuhiro Marumo, Shizuoka (JP); Keiyu Ou, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 713 days.

(21) Appl. No.: 17/106,170

(22) Filed: Nov. 29, 2020

(65) Prior Publication Data

US 2021/0088905 A1 Mar. 25, 2021

Related U.S. Application Data

(63) Continuation of application No. PCT/JP2019/026029, filed on Jul. 1, 2019.

(30) Foreign Application Priority Data

Aug. 29, 2018 (JP) .................... 2018-160287
Apr. 4, 2019 (JP) .................... 2019-072107

(51) Int. Cl.
*G03F 7/039* (2006.01)
*C08L 33/10* (2006.01)
*G03F 7/038* (2006.01)
*G03F 7/20* (2006.01)
*G03F 7/32* (2006.01)

(52) U.S. Cl.
CPC ............ *G03F 7/0392* (2013.01); *C08L 33/10* (2013.01); *G03F 7/0382* (2013.01); *G03F 7/32* (2013.01); *G03F 7/20* (2013.01)

(58) Field of Classification Search
None
See application file for complete search history.

(56) References Cited

U.S. PATENT DOCUMENTS

| 9,040,224 | B2 | 5/2015 | Kawaue et al. |
| 9,122,147 | B2 | 9/2015 | Hatakeyama et al. |
| 9,223,205 | B2 | 12/2015 | Ohashi et al. |
| 11,150,554 | B2 | 10/2021 | Nakamura et al. |
| 2013/0089819 | A1* | 4/2013 | Kawaue ............. C07C 309/09 560/221 |
| 2014/0178821 | A1* | 6/2014 | Kawaue ............. C07C 309/00 549/313 |
| 2015/0004545 | A1* | 1/2015 | Namai ............. G03F 7/027 549/399 |
| 2016/0320699 | A1 | 11/2016 | Yamada et al. |
| 2016/0376233 | A1* | 12/2016 | Yamazaki ............. G03F 7/2059 430/270.1 |
| 2017/0003591 | A1* | 1/2017 | Mochizuki ............. G03F 1/22 |
| 2017/0192355 | A1* | 7/2017 | Kojima ............. G03F 7/40 |
| 2017/0315442 | A1 | 11/2017 | Fukushima et al. |
| 2018/0299778 | A1* | 10/2018 | Nakamura ............ G03F 7/2041 |
| 2018/0321585 | A1 | 11/2018 | Kinoshita |
| 2019/0285983 | A1 | 9/2019 | Nishikori |

(Continued)

FOREIGN PATENT DOCUMENTS

| CN | 106094450 | 11/2016 |
| CN | 108463773 | 8/2018 |

(Continued)

OTHER PUBLICATIONS

"International Search Report (Form PCT/ISA/210) of PCT/JP2019/026029," mailed on Sep. 17, 2019, with English translation thereof, pp. 1-5.
"Written Opinion of the International Searching Authority (Form PCT/ISA/237) of PCT/JP2019/026029," mailed on Sep. 17, 2019, with English translation thereof, pp. 1-13.
"Office Action of Taiwan Counterpart Application", issued on Jan. 31, 2023, with English translation thereof, pp. 1-38.
"Office Action of Japan Counterpart Application", issued on Jan. 31, 2023, with English translation thereof, pp. 1-3.
"Dismissal of Amendment of Japan Counterpart Application", issued on Jan. 31, 2023, with English translation thereof, pp. 1-5.

(Continued)

*Primary Examiner* — Martin J Angebranndt
(74) *Attorney, Agent, or Firm* — JCIPRNET

(57) ABSTRACT

An actinic ray-sensitive or radiation-sensitive resin composition includes a photoacid generator A that generates an acid represented by General Formula (I), the acid having a pKa of −1.00 or more; one or more selected from the group consisting of a photoacid generator B that generates an acid having a pKa larger than that of an acid generated from the photoacid generator A by 1.00 or more, and a nitrogen-containing compound C having a pKa of a conjugate acid thereof larger than that of the acid generated from the photoacid generator A by 1.00 or more; and an acid-decomposable resin, in which in a case where the actinic ray-sensitive or radiation-sensitive resin composition includes a photoacid generator D that generates an acid having a pKa of less than −1.00, a ratio of the number of moles of the photoacid generator A to the number of moles of the photoacid generator D in the composition, is 1.0 or more.

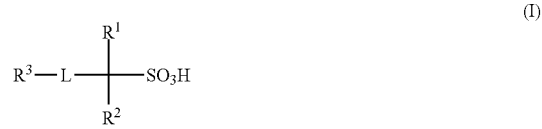

(I)

5 Claims, No Drawings

(56) References Cited

U.S. PATENT DOCUMENTS

2019/0294043 A1 9/2019 Asakawa et al.
2021/0109446 A1 4/2021 Goto et al.

FOREIGN PATENT DOCUMENTS

| | | | | |
|---|---|---|---|---|
| JP | 2006178317 | 7/2006 | | |
| JP | 2014157246 | 8/2014 | | |
| JP | 2014209167 | 11/2014 | | |
| JP | 2016206586 | 12/2016 | | |
| JP | 2017197489 | 11/2017 | | |
| KR | 20160128244 | 11/2016 | | |
| KR | 20170045136 | 4/2017 | | |
| KR | 20170123253 | 11/2017 | | |
| TW | 201344352 | 11/2013 | | |
| TW | 201409168 | 3/2014 | | |
| TW | 201736958 | 10/2017 | | |
| WO | WO-2014034190 A1 * | 3/2014 | ........... | C07C 309/08 |
| WO | WO-2015159830 A1 * | 10/2015 | ........... | C07C 309/06 |
| WO | 2017065207 | 4/2017 | | |
| WO | 2017122528 | 7/2017 | | |
| WO | 2018101339 | 6/2018 | | |
| WO | 2018116916 | 6/2018 | | |
| WO | 2020004306 | 1/2020 | | |

OTHER PUBLICATIONS

Office Action of Korea Counterpart Application, with English translation thereof, issued on Sep. 19, 2022, pp. 1-22.
Office Action of Japan Counterpart Application, with English translation thereof, issued on Aug. 16, 2022, pp. 1-5.
"Office Action of Japan Counterpart Application", issued on Feb. 15, 2022, with English translation thereof, p. 1-p. 5.
"Office Action of China Counterpart Application", issued on May 4, 2024, with English translation thereof, pp. 1-10.
"Office Action of China Counterpart Application", issued on Dec. 22, 2023, with English translation thereof, pp. 1-12.
"Office Action of China Counterpart Application", issued on Oct. 13, 2024, with English translation thereof, p. 1-p. 14.
"Office Action of Japan Counterpart Application", issued on Mar. 12, 2024, with English translation thereof, p. 1-p. 6.

* cited by examiner

ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

CROSS-REFERENCE TO RELATED APPLICATIONS

This application is a Continuation of PCT International Application No. PCT/JP2019/026029 filed on Jul. 1, 2019, which claims priority under 35 U.S.C § 119(a) to Japanese Patent Application No. 2018-160287 filed on Aug. 29, 2018, and Japanese Patent Application No. 2019-072107 filed on Apr. 4, 2019. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition, a resist film, a pattern forming method, and a method for manufacturing an electronic device.

2. Description of the Related Art

Since the advent of a resist for KrF excimer laser (248 nm), a pattern forming method utilizing chemical amplification is used in order to compensate for a decrease in sensitivity due to light absorption. For example, in a positive tone chemical amplification method, first, a photoacid generator included in the exposed area decomposes upon irradiation with light to generate an acid. Then, in a post-exposure baking step and the like, a solubility in a developer changes by, for example, changing an alkali-insoluble group contained in a resin included in an actinic ray-sensitive or radiation-sensitive resin composition to an alkali-soluble group by the catalytic action of an acid thus generated. Thereafter, development is performed using a basic aqueous solution, for example. As a result, the exposed area is removed to obtain a desired pattern.

In order to make a semiconductor element finer, the wavelength of an exposure light source has been shortened and a projection lens with a high numerical aperture (high NA) has been advanced, and currently, an exposure machine using an ArF excimer laser having a wavelength of 193 nm as a light source is under development.

Under these circumstances, various configurations have been proposed as actinic ray-sensitive or radiation-sensitive resin compositions.

For example, JP2014-209167A discloses a resist composition including a photodegradable quencher (DO) consisting of a compound represented by General Formula (d0).

(d0)

$R^1{-}O{-}\overset{O}{\underset{}{C}}{-}Y^1{-}\overset{R^2}{\underset{R^3}{C}}{-}SO_3^{\ominus} \quad (M^{m\oplus})_{1/m}$

SUMMARY OF THE INVENTION

The present inventors have specifically examined the techniques disclosed in JP2014-209167A, and have thus found that the resist composition of JP2014-209167A has room for improvement in the line width roughness (LWR) performance of a pattern obtained.

Therefore, an object of the present invention is to provide an actinic ray-sensitive or radiation-sensitive resin composition with which a pattern having excellent LWR performance is obtained.

In addition, another object of the present invention is to provide a resist film, a pattern forming method, and a method for manufacturing an electronic device, each relating to the actinic ray-sensitive or radiation-sensitive resin composition.

The present inventors have conducted intensive studies to accomplish the objects, and as a result, they have found that the objects can be accomplished using a photoacid generator having a specific structure, thereby completing the present invention.

That is, the present inventors have found that the objects can be accomplished by the following configurations.

[1] An actinic ray-sensitive or radiation-sensitive resin composition comprising:
a photoacid generator A that generates an acid represented by General Formula (I), the acid having a pKa of −1.00 or more;
one or more selected from the group consisting of a photoacid generator B that generates an acid having a pKa larger than that of an acid generated from the photoacid generator A by 1.00 or more, and a nitrogen-containing compound C having a pKa of a conjugate acid thereof larger than that of the acid generated from the photoacid generator A by 1.00 or more; and
an acid-decomposable resin,
in which the actinic ray-sensitive or radiation-sensitive resin composition may further include a photoacid generator D that is a compound different from the nitrogen-containing compound C and generates an acid having a pKa of less than −1.00, and
in a case where the actinic ray-sensitive or radiation-sensitive resin composition includes the photoacid generator D, a ratio of the number of moles of the photoacid generator A to the number of moles of the photoacid generator D in the actinic ray-sensitive or radiation-sensitive resin composition, is 1.0 or more.

[2] The actinic ray-sensitive or radiation-sensitive resin composition as described in [1],
in which in General Formula (I) which will be described later, L represents a divalent linking group consisting of a combination of one linking group S and one or more alkylene groups which may have a substituent, or a divalent linking group consisting of one linking group S.

[3] The actinic ray-sensitive or radiation-sensitive resin composition as described in [1] or [2],
in which in General Formula (I) which will be described later, $R^3$ represents an organic group having a cyclic structure.

[4] The actinic ray-sensitive or radiation-sensitive resin composition as described in any one of [1] to [3],
in which the acid-decomposable resin is a methacrylic ester-based resin.

[5] The actinic ray-sensitive or radiation-sensitive resin composition as described in any one of [1] to [4], in which in General Formula (I) which will be described later, L represents a divalent linking group consisting of one or more linking groups S.

[6] The actinic ray-sensitive or radiation-sensitive resin composition as described in any one of [1] to [5],
in which in General Formula (I) which will be described later, the linking group S represents a group selected from the group consisting of $*^A$—O—CO—O—$*^B$, $*^A$—CO—$*^B$, $*^A$—O—CO—$*^B$, $*^A$—O—$*^B$, $*^A$—S—$*^B$, and $*^A$—SO$_2$—$*^B$.

[7] A resist film formed from the actinic ray-sensitive or radiation-sensitive resin composition as described in any one of [1] to [6].

[8] A pattern forming method comprising:
forming a resist film using the actinic ray-sensitive or radiation-sensitive resin composition as described in any one of [1] to [6] on a support;
exposing the resist film; and
developing the exposed resist film using a developer.

[9] A method for manufacturing an electronic device, comprising the pattern forming method as described in [8].

According to the present invention, it is possible to provide an actinic ray-sensitive or radiation-sensitive resin composition with which a pattern thus formed has excellent LWR performance.

In addition, another object of the present invention is to provide a resist film, a pattern forming method, and a method for manufacturing an electronic device, each relating to the actinic ray-sensitive or radiation-sensitive resin composition.

DESCRIPTION OF THE PREFERRED EMBODIMENTS

Hereinafter, the present invention will be described in detail.

Description of configuration requirements described below may be made on the basis of representative embodiments of the present invention in some cases, but the present invention is not limited to such embodiments.

In citations for a group (atomic group) in the present specification, in a case where the group is cited without specifying whether it is substituted or unsubstituted, the group includes both a group having no substituent and a group having a substituent as long as this does not impair the spirit of the present invention. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

"Actinic rays" or "radiation" in the present specification means, for example, a bright line spectrum of a mercury lamp, far ultraviolet rays typified by an excimer laser, extreme ultraviolet rays (EUV light), X-rays, electron beams (EB), or the like. "Light" in the present specification means actinic rays or radiation.

Unless otherwise specified, "exposure" in the present specification encompasses not only exposure by a bright line spectrum of a mercury lamp, far ultraviolet rays typified by an excimer laser, extreme ultraviolet rays (EUV light), X-rays, or the like, but also lithography by particle rays such as electron beams and ion beams.

In the present specification, a numerical range expressed using "to" is used in a meaning of a range that includes the preceding and succeeding numerical values of "to" as the lower limit value and the upper limit value, respectively.

In the present specification, (meth)acrylate represents acrylate and methacrylate, and (meth)acryl represents acryl and methacryl.

In the present specification, the weight-average molecular weight (Mw), the number-average molecular weight (Mn), and the dispersity (also referred to as a molecular weight distribution) (Mw/Mn) of a resin are each defined as a value converted in terms of polystyrene by means of gel permeation chromatography (GPC) measurement (solvent: tetrahydrofuran, flow amount (amount of a sample injected): 10 µL, columns: TSK gel Multipore HXL-M manufactured by Tosoh Corporation, column temperature: 40° C., flow rate: 1.0 mL/min, detector: differential refractive index detector) using a GPC apparatus (HLC-8120 GPC manufactured by Tosoh Corporation).

In the present specification, the acid dissociation constant pKa (pKa) represents an acid dissociation constant pKa in an aqueous solution, and is defined, for example, in Chemical Handbook (II) (Revised 4th Edition, 1993, compiled by the Chemical Society of Japan, Maruzen Company, Ltd.). The lower the value of the acid dissociation constant pKa, the higher the acid strength. The value of the pKa is determined using the following software package 1 by computation from a value based on a Hammett substituent constant and the database of publicly known literature values. All of the values of pKa described in the present specification indicate values determined by computation using the software package.

Software Package 1: Advanced Chemistry Development (ACD/Labs) Software V 8.14 for Solaris (1994-2007 ACD/Labs).

In the present specification, examples of the halogen atom include a fluorine atom, a chlorine atom, a bromine atom, and an iodine atom.

[Actinic Ray-Sensitive or Radiation-Sensitive Resin Composition]

The actinic ray-sensitive or radiation-sensitive resin composition of the embodiment of the present invention (hereinafter also simply referred to as the "composition" or the "composition of the embodiment of the present invention") will be described.

The composition of the embodiment of the present invention is a so-called resist composition, and may be either a positive tone resist composition or a negative tone resist composition. In addition, the composition of the embodiment of the present invention may be either a resist composition for alkali development or a resist composition for organic solvent development.

The composition of the embodiment of the present invention is typically a chemically amplified resist composition.

The composition of the embodiment of the present invention includes a photoacid generator A, one or more selected from the group consisting of a photoacid generator B and a nitrogen-containing compound C, and an acid-decomposable resin.

The photoacid generator A is a compound which generates an acid represented by General Formula (I) which will be described later, the acid having a pKa of −1.00 or more.

The photoacid generator B is a compound that generates an acid having a pKa larger than that of the acid generated from the photoacid generator by 1.00 or more.

The nitrogen-containing compound C is a compound having a pKa of a conjugate acid thereof larger than that of the acid generated from the photoacid generator A by 1.00 or more.

Furthermore, the composition of the embodiment of the present invention may include a photoacid generator D.

The photoacid generator D is a compound that generates an acid having a pKa of less than −1.00.

In a case where the composition includes the photoacid generator D, a ratio of the number of moles of the photoacid generator A to the number of moles of the photoacid generator D in the composition is 1.0 or more.

Mechanism by which the objects of the present invention can be accomplished through such a configuration is not necessarily clear, but is presumed as follows by the present inventors.

In a case where a resist film is formed from the composition, the photoacid generator A that generates a relatively weak acid does not easily aggregate in the resist film and has good dispersibility. Furthermore, since the composition contains at least one of the photoacid generator B or the nitrogen-containing compound C, the diffusion of an acid generated from the photoacid generator A is controlled.

In addition, even in a case where the photoacid generator D is included in the composition, the content thereof is less than the content of the photoacid generator A (based on the amount of the substance), and thus, the amount of the photoacid generator D present in the state of aggregating in the resist film is suppressed. Therefore, it is presumed that a resist film formed using the composition of the embodiment of the present invention easily undergoes a uniform reaction upon exposure, and the LWR performance of a pattern thus obtained is improved.

<Acid-Decomposable Resin (Resin A)>

The composition of the embodiment of the present invention includes an acid-decomposable resin (hereinafter also referred to as a "resin A").

The acid-decomposable resin usually has a repeating unit having a group having a polarity that increases through decomposition by the action of an acid (hereinafter also referred to as an "acid-decomposable group").

In the pattern forming method of an embodiment of the present invention which will be described later, typically, in a case where an alkali developer is adopted as a developer, a positive tone pattern is suitably formed, and in a case where an organic developer is adopted as the developer, a negative tone pattern is suitably formed.

(Repeating Unit Having Acid-Decomposable Group)

The resin A preferably has a repeating unit having an acid-decomposable group.

The acid-decomposable group preferably has a structure in which a polar group is protected with a group that is eliminated through decomposition by the action of an acid (eliminable group).

Examples of the polar group include an acidic group (a group which dissociates in a 2.38%-by-mass aqueous tetramethylammonium hydroxide solution), such as a carboxyl group, a phenolic hydroxyl group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group, and an alcoholic hydroxyl group.

Moreover, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol group (for example, a hexafluoroisopropanol group) having the α-position substituted with an electron-withdrawing group such as a fluorine atom is excluded as a hydroxyl group. The alcoholic hydroxyl group is preferably a hydroxyl group having an acid dissociation constant (pKa) of 12 to 20.

As the polar group, a carboxyl group, a phenolic hydroxyl group, a fluorinated alcohol group (preferably a hexafluoroisopropanol group), or a sulfonic acid group is preferable.

The group which is preferable as the acid-decomposable group is a group in which a hydrogen atom is substituted with a group (eliminable group) that is eliminated by the action of an acid.

Examples of the group (eliminable group) that is eliminated by the action of an acid include —C($R_{36}$)($R_{37}$)($R_{38}$), —C($R_{36}$)($R_{37}$)(O$R_{39}$), and —C($R_{01}$)($R_{02}$)(O$R_{39}$).

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, an aralkyl group, or an alkenyl group.

As the alkyl group as each of $R_{36}$ to $R_{39}$, $R_{01}$, and $R_{02}$, an alkyl group having 1 to 8 carbon atoms is preferable, and examples thereof include a methyl group, an ethyl group, a propyl group, an n-butyl group, a sec-butyl group, a hexyl group, and an octyl group.

The cycloalkyl group as each of $R_{36}$ to $R_{39}$, $R_{01}$, and $R_{02}$ may be either a monocycle or polycycle. As the monocycle, a cycloalkyl group having 3 to 8 carbon atoms is preferable, and examples thereof include a cyclopropyl group, a cyclobutyl group, a cyclopentyl group, a cyclohexyl group, and a cyclooctyl group. As the polycycle, a cycloalkyl group having 6 to 20 carbon atoms is preferable, and examples thereof include an adamantyl group, a norbornyl group, an isobornyl group, a camphanyl group, a dicyclopentyl group, an α-pinene group, a tricyclodecanyl group, a tetracyclododecyl group, and an androstanyl group. Further, at least one carbon atom in the cycloalkyl group may be substituted with a heteroatom such as an oxygen atom.

The aryl group as each of $R_{36}$ to $R_{39}$, $R_{01}$, and $R_{02}$ is preferably an aryl group having 6 to 10 carbon atoms, and examples thereof include a phenyl group, a naphthyl group, and an anthryl group.

The aralkyl group as each of $R_{36}$ to $R_{39}$, $R_{01}$, and $R_{02}$ is preferably an aralkyl group having 7 to 12 carbon atoms, and examples thereof include a benzyl group, a phenethyl group, and a naphthylmethyl group.

The alkenyl group as each of $R_{36}$ to $R_{39}$, $R_{01}$, and $R_{02}$ is preferably an alkenyl group having 2 to 8 carbon atoms, and examples thereof include a vinyl group, an allyl group, a butenyl group, and a cyclohexenyl group.

The ring formed by the mutual bonding of $R_{36}$ and $R_{37}$ is preferably a (monocyclic or polycyclic) cycloalkyl group. As the monocyclic cycloalkyl group, a cyclopentyl group or a cyclohexyl group is preferable, and as the polycyclic cycloalkyl group, a norbornyl group, a tetracyclodecanyl group, a tetracyclododecanyl group, or an adamantyl group is preferable.

The acid-decomposable group preferably has a tertiary alkyl ester group, an acetal group, a cumyl ester group, an enol ester group, or an acetal ester group, and more preferably has the acetal group or the tertiary alkyl ester group.

The resin A preferably has a repeating unit represented by General Formula (AI) as a repeating unit having an acid-decomposable group.

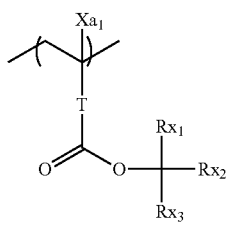

(AI)

In General Formula (AI), T represents a single bond or a divalent linking group.

Examples of the divalent linking group of T include an alkylene group, an arylene group, —COO-Rt-, and —O-Rt-. In the formulae, Rt represents an alkylene group, a cycloalkylene group, or an arylene group.

T is preferably the single bond or —COO-Rt-. Rt is preferably a chained alkylene group having 1 to 5 carbon atoms, and more preferably —CH$_2$—, —(CH$_2$)$_2$—, or —(CH$_2$)$_3$—.

T is more preferably the single bond.

In General Formula (AI), Xa$_1$ represents a hydrogen atom, a halogen atom, or a monovalent organic group.

Xa$_1$ is preferably a hydrogen atom or an alkyl group.

The alkyl group of Xa$_1$ may have a substituent, and examples of the substituent include a hydroxyl group and a halogen atom (preferably a fluorine atom).

The alkyl group of Xa$_1$ preferably has 1 to 4 carbon atoms, and examples thereof include a methyl group, an ethyl group, a propyl group, a hydroxymethyl group, and a trifluoromethyl group. The alkyl group of Xa$_1$ is preferably the methyl group.

In General Formula (AI), Rx$_1$ to Rx$_3$ each independently represent an alkyl group or a cycloalkyl group.

Any two of Rx$_1$, Rx$_2$, or Rx$_3$ may or may not be bonded to each other to form a ring structure.

The alkyl group of each of Rx$_1$, Rx$_2$, and Rx$_3$ may be linear or branched, and is preferably a methyl group, an ethyl group, an n-propyl group, an isopropyl group, an n-butyl group, an isobutyl group, a t-butyl group, or the like. The alkyl group preferably has 1 to 10 carbon atoms, more preferably has 1 to 5 carbon atoms, and still more preferably has 1 to 3 carbon atoms. In the alkyl groups of each of Rx$_1$, Rx$_2$, and Rx$_3$, a part of carbon-carbon bonds may be a double bond.

The cycloalkyl group of each of Rx$_1$, Rx$_2$, and Rx$_3$ may be either a monocycle or a polycycle. Examples of the monocyclic cycloalkyl group include a cyclopentyl group and a cyclohexyl group. Examples of the polycyclic cycloalkyl group include a norbornyl group, a tetracyclodecanyl group, a tetracyclododecanyl group, and an adamantyl group.

A ring formed by the bonding of two of Rx$_1$, Rx$_2$, and Rx$_3$ may be either a monocycle or a polycycle.

Examples of the monocycle include monocyclic cycloalkane rings such as a cyclopentyl ring, a cyclohexyl ring, a cycloheptyl ring, and a cyclooctane ring. Examples of the polycycle include polycyclic cycloalkyl rings such as a norbornane ring, a tetracyclodecane ring, a tetracyclododecane ring, and an adamantane ring. Among these, the cyclopentyl ring, the cyclohexyl ring, or the adamantane ring is preferable.

In addition, as a ring formed by the bonding of two of Rx$_1$, Rx$_2$, and Rx$_3$, a ring shown below is also preferable.

Specific examples of the monomer corresponding to the repeating unit represented by General Formula (AI) are shown below.

The following specific examples correspond to a case where Xa$_1$ in General Formula (AI) is a methyl group, but Xa$_1$ can be optionally substituted with a hydrogen atom, a halogen atom, or a monovalent organic group.

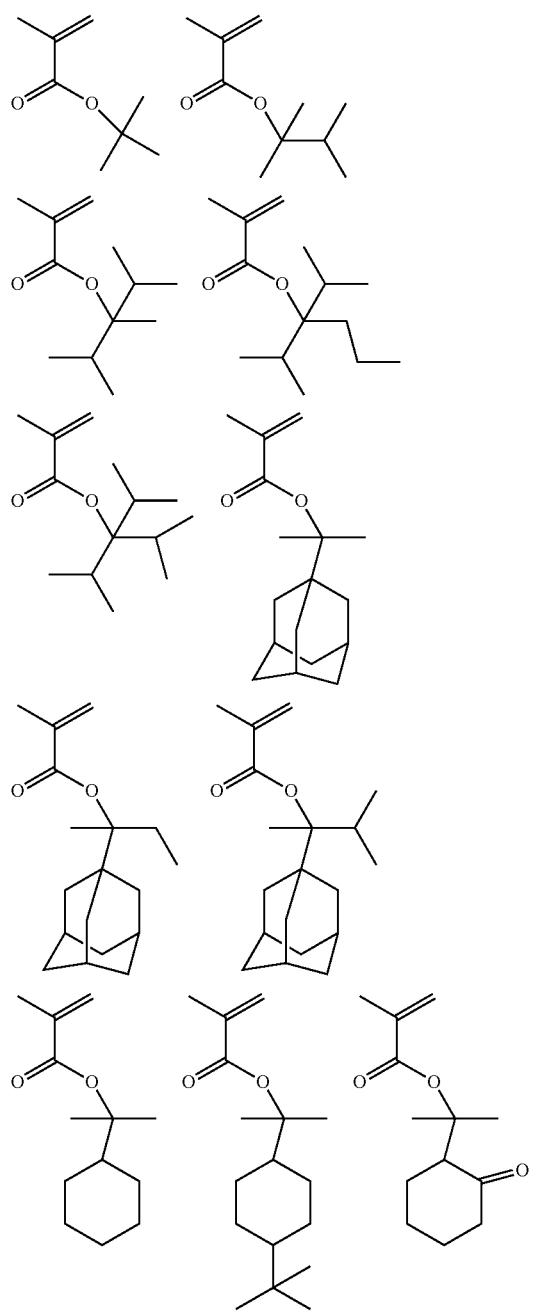

-continued

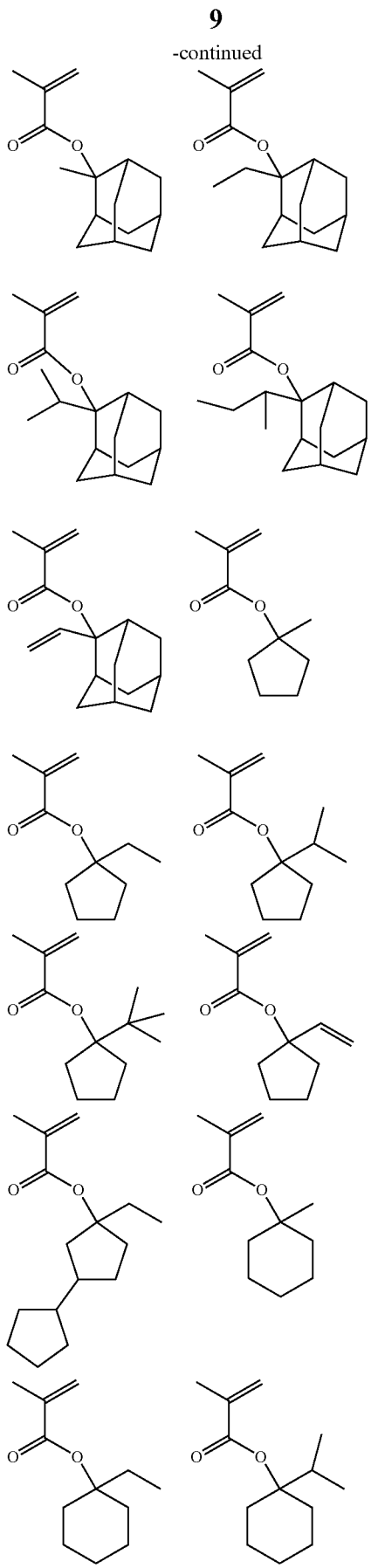

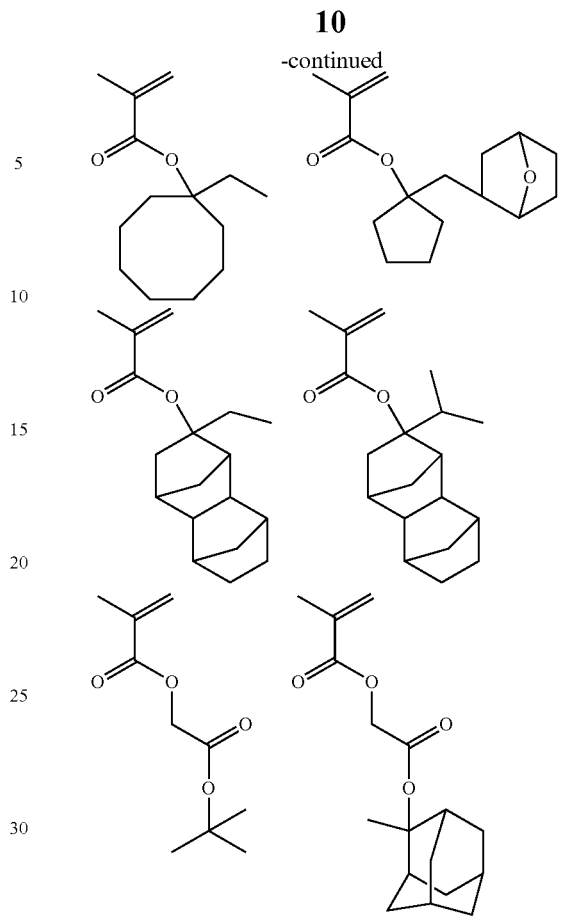

It is also preferable that the resin A has the repeating unit described in paragraphs <0336> to <0369> of the specification of US2016/0070167A1 as the repeating unit having an acid-decomposable group.

Furthermore, the resin A may have a repeating unit including a group that decomposes by the action of an acid to produce an alcoholic hydroxyl group described in paragraphs <0363> and <0364> of the specification of US2016/0070167A1 as the repeating unit having an acid-decomposable group.

The content of the repeating unit having an acid-decomposable group included in the resin A (in a case where the repeating units having an acid-decomposable group are present in a plural number, a total content thereof) is preferably 10% to 90% by mole, more preferably 20% to 80% by mole, and still more preferably 30% to 70% by mole, with respect to all the repeating units of the resin A.

The resin A may have the repeating units having an acid-decomposable group singly or in combination of two or more kinds thereof. In a case where the resin A has two or more kinds of the repeating units, the total content thereof is preferably within the suitable content range.

(Repeating Unit Having at Least One Selected from Group Consisting of Lactone Structure, Sultone Structure, and Carbonate Structure)

The resin A preferably has a repeating unit having at least one selected from the group consisting of a lactone structure, a sultone structure, and a carbonate structure.

As the lactone structure or the sultone structure, any structure which has a lactone ring or sultone ring may be used, but a lactone structure having a 5- to 7-membered ring or a sultone structure having a 5- to 7-membered ring is preferable.

A lactone structure in which another ring is fused with the 5- to 7-membered lactone ring so as to form a bicyclo structure or a spiro structure is also preferable. A sultone structure in which another ring is fused with a 5- to 7-membered sultone ring so as to form a bicyclo structure or a spiro structure is also preferable.

Among those, the resin A preferably has a repeating unit having a lactone structure represented by any of General Formulae (LC1-1) to (LC1-22) or a sultone structure represented by any of General Formulae (SL1-1) to (SL1-3). Further, the lactone structure or the sultone structure may be bonded directly to the main chain.

Among those, the lactone structure represented by General Formula (LC1-1), General Formula (LC1-4), General Formula (LC1-5), General Formula (LC1-8), General Formula (LC1-16), General Formula (LC1-21), or General Formula (LC1-22), or the sultone structure represented by General Formula (SL1-1) is preferable.

LC1-1
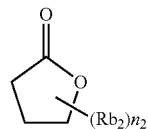

LC1-2
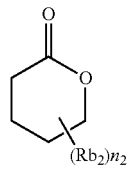

LC1-3
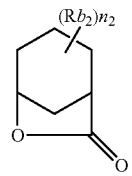

LC1-4
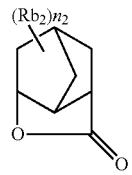

LC1-5
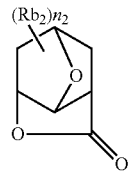

LC1-6
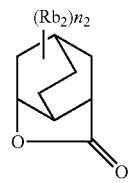

LC1-7
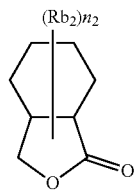

LC1-8
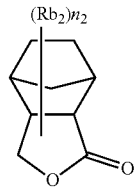

LC1-9
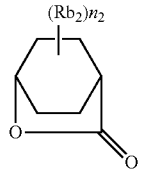

LC1-10
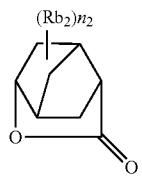

LC1-11
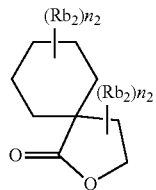

LC1-12
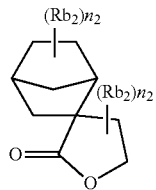

LC1-13
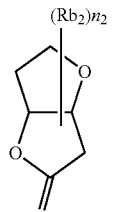

LC1-14
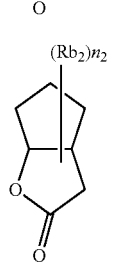

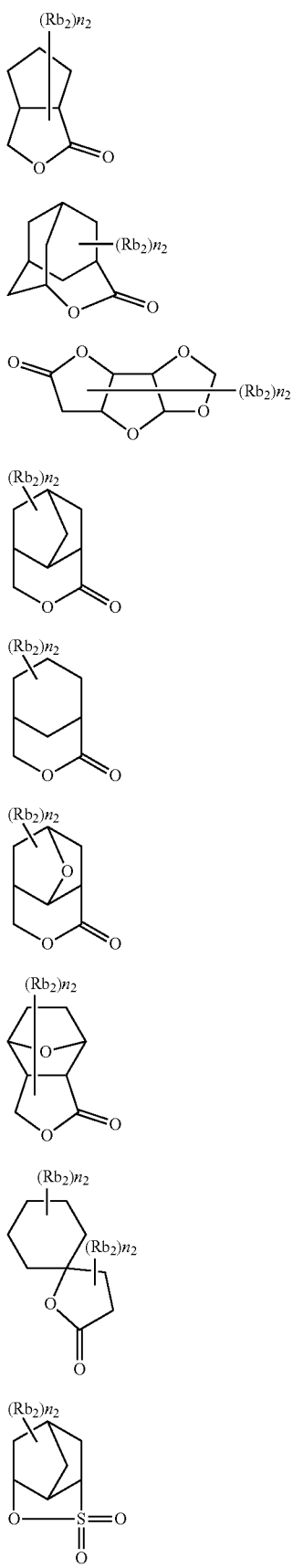

LC1-15

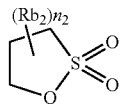

LC1-16

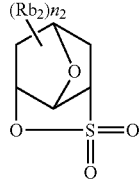

LC1-17

LC1-18

LC1-19

LC1-20

LC1-21

LC1-22

SL1-1

SL1-2

SL1-3

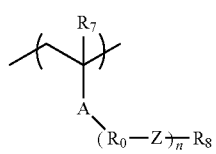

The lactone structure or the sultone structure may or may not have a substituent ($Rb_2$). As the substituent ($Rb_2$), an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, or an acid-decomposable group is preferable, and an alkyl group having 1 to 4 carbon atoms, the cyano group, or the acid-decomposable group is more preferable.

$n_2$ represents an integer of 0 to 4. In a case where $n_2$ is 2 or more, the substituents ($Rb_2$) which are present in a plural number may be the same as or different from each other. Further, the substituents ($Rb_2$) which are present in a plural number may be bonded to each other to form a ring.

As the repeating unit having a lactone structure or a sultone structure, a repeating unit represented by General Formula (III) is preferable.

$$\text{(III)}$$

In General Formula (III),

A represents an ester bond (a group represented by —COO—) or an amide bond (a group represented by —CONH—).

n is the number of repetitions of the structure represented by —$R_0$—Z—, represents an integer of 0 to 5, and is preferably 0 or 1, and more preferably 0. In a case where n is 0, (—$R_0$—Z—)n is a single bond.

$R_0$ represents an alkylene group, a cycloalkylene group, or a combination thereof. In a case where $R_0$'s are present in a plural number, $R_0$'s which are present in a plural number may be the same as or different from each other.

The alkylene group or the cycloalkylene group of $R_0$ may have a substituent.

Z represents a single bond, an ether bond, an ester bond, an amide bond, a urethane bond, or a urea bond. In a case where Z's are present in a plural number, Z's may be the same as or different from each other.

Among those, Z is preferably an ether bond or an ester bond, and more preferably the ester bond.

$R_8$ represents a monovalent organic group having a lactone structure or a sultone structure.

Among those, any of the structures represented by General Formulae (LC1-1) to (LC1-22) and the structures represented by General Formulae (SL1-1) to (SL1-3) is preferably a group obtained by removing one hydrogen atom from one carbon atom constituting the lactone structure or the sultone structure.

In addition, it is preferable that the carbon atom from which one hydrogen atom is removed is not a carbon atom constituting the substituent ($Rb_2$).

$R_7$ represents a hydrogen atom, a halogen atom, or a monovalent organic group (preferably a methyl group).

Examples of a monomer corresponding to the repeating unit having at least one selected from the group consisting of a lactone structure and a sultone structure are shown below.

In the following examples, the methyl group bonded to the vinyl group may be substituted with a hydrogen atom, a halogen atom, or a monovalent organic group.

-continued

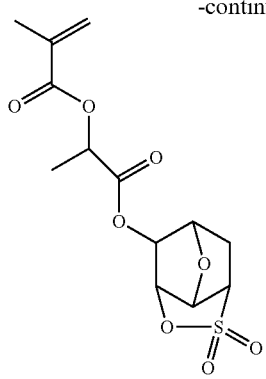
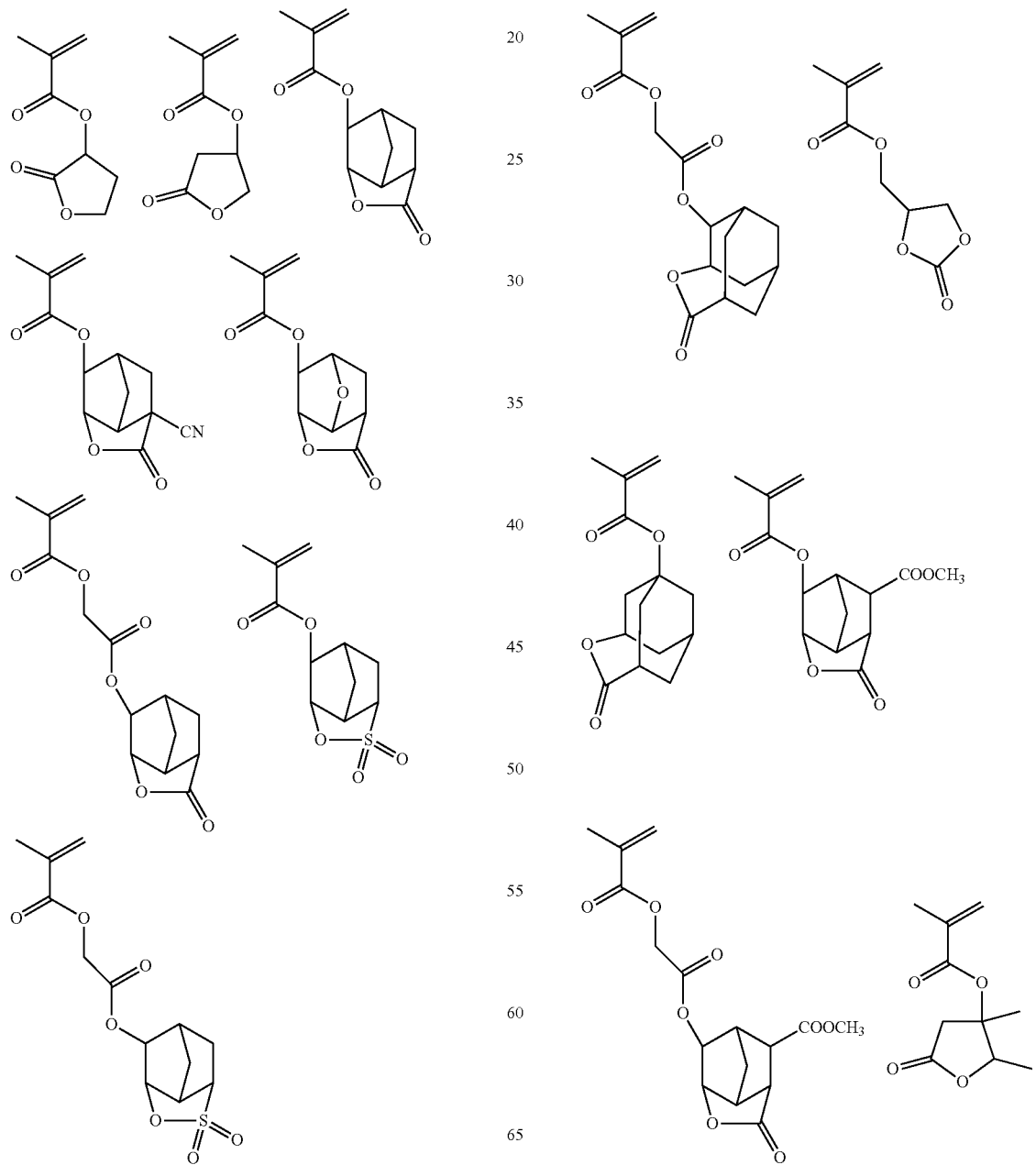

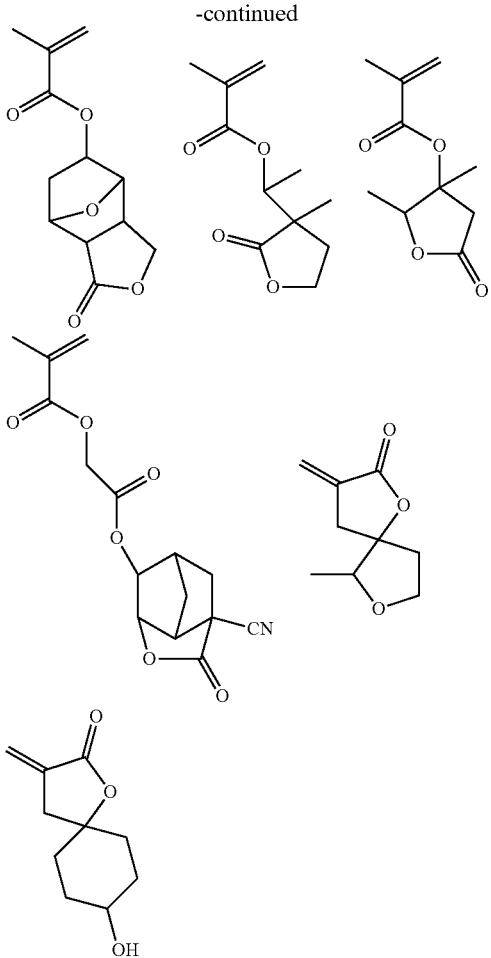

The resin A may have a repeating unit having a carbonate structure. As the carbonate structure, a cyclic carbonate ester structure is preferable.

As the repeating unit having a cyclic carbonate ester structure, a repeating unit represented by General Formula (A-1) is preferable.

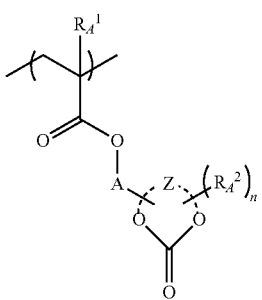

(A-1)

In General Formula (A-1), $R_A{}^1$ represents a hydrogen atom, a halogen atom, or a monovalent organic group (preferably a methyl group).

n represents an integer of 0 or more.

$R_A{}^2$ represents a substituent. In a case where n is 2 or more, $R_A{}^2$ which are present in a plural number may be the same as or different from each other.

A represents a single bond or a divalent linking group.

Z represents an atomic group that forms a monocycle or polycycle with a group represented by —O—CO—O— in the formula.

It is also preferable that the resin A has the repeating units described in paragraphs <0370> to <0414> of the specification of US2016/0070167A1 as a repeating unit having at least one selected from the group consisting of a lactone structure, a sultone structure, and a carbonate structure.

In a case where the resin A has a repeating unit having at least one selected from the group consisting of a lactone structure, a sultone structure, and a carbonate structure, the content of the repeating unit having at least one selected from the group consisting of a lactone structure, a sultone structure, and a carbonate structure included in the resin A is preferably 5% to 70% by mole, more preferably 10% to 65% by mole, and still more preferably 20% to 60% by mole, with respect to all the repeating units in the resin A.

The resin A may have only one kind or two or more kinds of repeating units having at least one selected from the group consisting of a lactone structure, a sultone structure, and a carbonate structure. In a case where the resin A has two or more kinds of the repeating units, the total content thereof is preferably within the suitable content range.

(Repeating Unit Having Proton Donating Group)

The resin A may have a repeating unit having a proton donating group, in addition to the above-mentioned repeating units.

The proton donating group is not particularly limited, and examples thereof include a group including a hydrogen atom bonded to a heteroatom such as an oxygen atom, a nitrogen atom, and a sulfur atom, and specifically, an acidic group (a group that dissociates in a 2.38%-by-mass aqueous tetramethylammonium hydroxide solution), such as a sulfonamido group, a carboxyl group, a hydroxyl group (as the hydroxyl group, an alcoholic hydroxyl group or a fluorinated alcohol group is preferable; further, the alcoholic hydroxyl group refers to a hydroxyl group bonded to a hydrocarbon group, which is other than a hydroxyl group (phenolic hydroxyl group) directly bonded to an aromatic ring; as the hydroxyl group, an aliphatic alcohol having an electron-withdrawing group such as a fluorine atom substituted at the α-position (hereinafter also referred to as a "fluorinated alcohol group", such as a hexafluoroisopropanol group) is excluded; and as the alcoholic hydroxyl group, the hydroxyl group having a pKa from 12 to 20 is preferable), a sulfonic acid group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group.

Among those, as the above-mentioned proton donating group, a sulfonamido group (as the sulfonamido group, an alkylsulfonamido group is preferable, and an alkylsulfonamido group represented by *—NH—SO$_2$—$R^X$ ($R^X$ represents an alkyl group having 1 to 10 carbon atoms (which may be in any of linear, branched, and cyclic forms); further, the alkyl group represented by Rx may have a substituent; examples of the substituent include a halogen atom (for example, a fluorine atom); and the alkyl group represented by $R^X$ preferably has 1 to 6 carbon atoms, and more preferably has 1 to 3 carbon atoms) is preferable), a carboxyl group, a hydroxyl group (as the hydroxyl group, an alcoholic hydroxyl group or a fluorinated alcohol group (for example, a hexafluoroisopropanol group) is preferable), or a sulfonic acid group is preferable, and the alkylsulfonamido group, the carboxyl group, or the hydroxyl group is more preferable.

The repeating unit having the above-mentioned proton donating group is preferably a repeating unit represented by General Formula (H2).

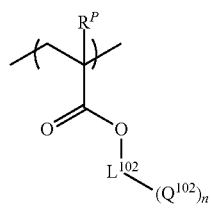

(H2)

In General Formula (H2), $R^P$ represents a hydrogen atom, a halogen atom, or a monovalent organic group (preferably a methyl group).

$L^{102}$ represents a substituted or unsubstituted hydrocarbon group having 1 to 30 carbon atoms, which may include a heteroatom.

The substituted or unsubstituted hydrocarbon group having 1 to 30 carbon atoms, which may include a heteroatom, represented by $L^{102}$, is not particularly limited, and examples thereof include a substituted or unsubstituted hydrocarbon group having 1 to 30 carbon atoms (preferably 1 to 20 carbon atoms, and more preferably having 1 to 15 carbon atoms), which may include —O—, —N($R^a$)—, —CO—, —S—, —SO$_2$—, or a group formed by combination thereof. $R^a$ represents a hydrogen atom or an alkyl group having 1 to 10 carbon atoms.

Furthermore, in a case where the hydrocarbon group includes a heteroatom, —CH$_2$— is substituted with the heteroatom.

The substituted or unsubstituted hydrocarbon group having 1 to 30 carbon atoms, which may include a heteroatom, represented by $L^{102}$ may be linear or branched, and may have a cyclic structure.

The substituted or unsubstituted hydrocarbon group having 1 to 30 carbon atoms, which may include a heteroatom, represented by $L^{102}$ preferably has one or more groups selected from the group consisting of an alkylene group and a cyclic hydrocarbon group, and is more preferably a group formed by combination of the alkylene group, the cyclic hydrocarbon group, or a group obtained by combination thereof. The alkylene group preferably has 1 to 5 carbon atoms. The cyclic hydrocarbon group may be a monocycle or a polycycle, and is preferably a non-aromatic ring (an adamantane ring or the like).

$Q^{102}$ represents a group having a proton donating group. $Q^{102}$ may be a proton donating group itself, as allowable.

Examples of the proton donating group are as described above.

n represents an integer of 1 or more, and preferably 1 to 5, and more preferably 1 or 2.

In a case where the resin A has a repeating unit having a proton donating group, the content of the repeating unit having a proton donating group included in the resin A is preferably 1% to 50% by mole, more preferably 3% to 40% by mole, and still more preferably 5% to 30% by mole, with respect to all the repeating units in the resin A.

The resin A may have only one kind or two or more kinds of the repeating units having a proton donating group. In a case where the resin A has two or more kinds of the repeating units, the total content thereof is preferably within the suitable content range.

(Repeating Unit Having Neither Acid-Decomposable Group Nor Polar Group)

The resin A may further have a repeating unit having neither an acid-decomposable group nor a polar group, in addition to the above-mentioned repeating units. The repeating unit having neither an acid-decomposable group nor a polar group preferably has an alicyclic hydrocarbon structure. Examples of the repeating unit having neither an acid-decomposable group nor a polar group include the repeating units described in paragraphs <0236> and <0237> of the specification of US2016/0026083A1.

Preferred examples of a monomer corresponding to the repeating unit having neither an acid-decomposable group nor a polar group are shown below.

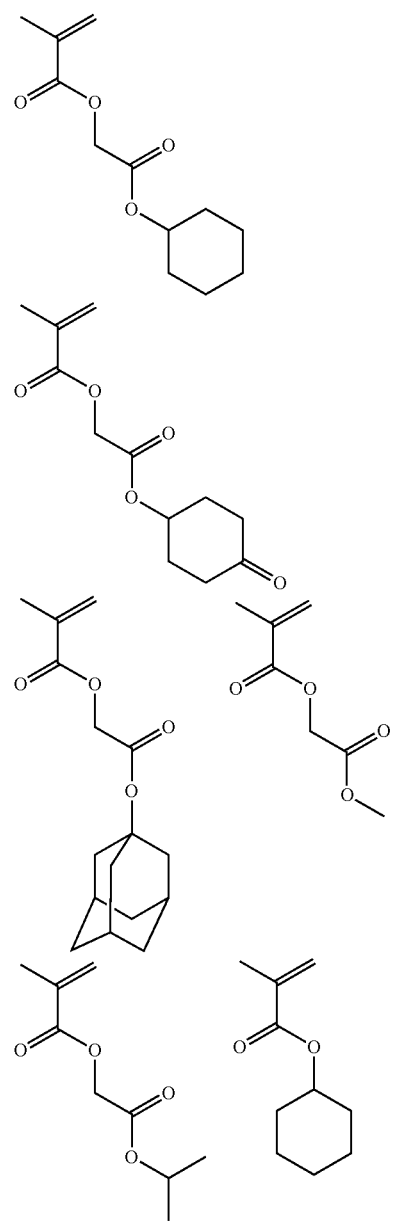

-continued

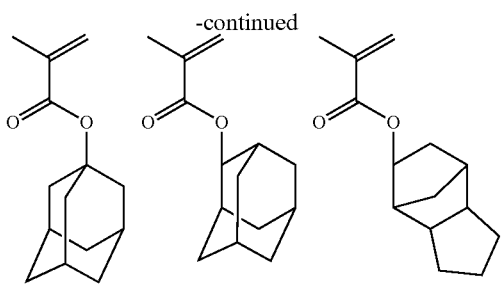

In addition to these, specific examples of the repeating unit having neither an acid-decomposable group nor a polar group include the repeating unit disclosed in paragraph <0433> of the specification of US2016/0070167A1.

In a case where the resin A has the repeating unit having neither an acid-decomposable group nor a polar group, the content of the repeating unit having neither an acid-decomposable group nor a polar group is preferably 5% to 40% by mole, more preferably 5% to 30% by mole, and still more preferably 5% to 25% by mole, with respect to all the repeating units in the resin A.

The resin A may have only one kind or two or more kinds of the repeating units having neither an acid-decomposable group nor a polar group. In a case where the resin A has two or more kinds of the repeating units, the total content thereof is preferably within the suitable content range.

The resin A may have a variety of repeating structural units, in addition to the above-mentioned repeating structural units, for the purpose of controlling dry etching resistance, suitability for a standard developer, adhesiveness to a substrate, and a resist profile, resolving power, heat resistance, sensitivity, and the like which are general characteristics required for a resist.

Examples of such a repeating structural unit include a repeating structural unit corresponding to a predetermined monomer, but are not limited thereto.

Examples of a predetermined monomer include a compound having one addition-polymerizable unsaturated bond, selected from acrylates, methacrylates, acrylamides, methacrylamides, allyl compounds, vinyl ethers, and vinyl esters.

In addition to these, an addition-polymerizable unsaturated compound that is copolymerizable with a monomer corresponding to the various repeating structural units may be used.

In the resin A, the content molar ratio of each repeating structural unit is appropriately set in order to adjust various performances.

In a case where the composition of the embodiment of the present invention is used for ArF exposure, it is preferable that the resin A has substantially no aromatic group from the viewpoint of transparency to ArF light. More specifically, the repeating unit having an aromatic group is preferably 5% by mole or less, more preferably 3% by mole or less, and ideally 0% by mole, with respect to all the repeating units in the resin A, that is, it is still more preferable that the repeating unit having an aromatic group is not included. In addition, the resin A preferably has a monocyclic or polycyclic alicyclic hydrocarbon structure.

The resin A is preferably a (meth)acrylic ester-based resin, and more preferably the methacrylic ester-based resin.

The (meth)acrylic ester-based resin (or the methacrylic ester-based resin) has a content of the (meth)acrylate-based repeating unit (or methacrylate-based repeating unit) of 80% by mole or more, preferably 90% by mole or more, more preferably 95% by mole or more, and still more preferably 99% by mole or more, with respect to all the repeating units of the resin A.

In the resin A, all the repeating units may be constituted with the (meth)acrylate-based repeating units. In this case, all of the repeating units may be the methacrylate-based repeating units, all of the repeating units may be the acrylate-based repeating units, and all of the repeating units are a combination of the methacrylate-based repeating units and the acrylate-based repeating units. Above all, the content of the acrylate-based repeating units is preferably 50% by mole or less with respect to all the repeating units of the resin A.

In addition, as the resin A, a known resin can be appropriately used. For example, the known resins disclosed in paragraphs <0055> to <0191> of the specification of US2016/0274458A1, paragraphs <0035> to <0085> of the specification of US2015/0004544A1, and paragraphs <0045> to <0090> of the specification of US2016/0147150A1 can be suitably used as the resin A.

In a case where the composition of the embodiment of the present invention is for KrF exposure, EB exposure, or EUV exposure, the resin A preferably has a repeating unit having an aromatic hydrocarbon group, and more preferably has a repeating unit including a phenolic hydroxyl group. Examples of the repeating unit including a phenolic hydroxyl group include a hydroxystyrene-based repeating unit and a hydroxystyrene (meth)acrylate-based repeating unit.

In a case where the composition of the embodiment of the present invention is for KrF exposure, EB exposure, or EUV exposure, it is preferable that the resin A has a structure in which a hydrogen atom of the phenolic hydroxyl group is protected with a group (eliminable group) that is eliminated through decomposition by the action of an acid.

In this case, the content of the repeating unit having an aromatic hydrocarbon group included in the resin A is preferably 30% to 100% by mole, more preferably 40% to 100% by mole, and still more preferably 50% to 100% by mole, with respect to all the repeating units in the resin A.

The weight-average molecular weight of the resin A is preferably 1,000 to 200,000, more preferably 2,000 to 20,000, still more preferably 3,000 to 15,000, and particularly preferably 3,000 to 12,000. The dispersity (Mw/Mn) is usually 1.0 to 3.0, preferably 1.0 to 2.6, more preferably 1.0 to 2.0, and still more preferably 1.1 to 2.0.

The resin A may be used singly or in combination of two or more kinds thereof.

The content of the resin A in the composition is usually 20% by mass or more, preferably 40% by mass or more, more preferably 60% by mass or more, and still more preferably 75% by mass or more, with respect to the total solid content in the composition. An upper limit thereof is not particularly limited, but is preferably 95% by mass or less, and more preferably 90% by mass or less.

In a case where two or more kinds of the resins A are used in the composition, the total content thereof is preferably within the suitable content range.

In addition, the solid content is intended to mean components excluding the solvent in the composition, and any of components other than the solvent are regarded as a solid content even in a case where they are liquid components.

<Photoacid Generator A>

The composition of the embodiment of the present invention includes a photoacid generator A.

The photoacid generator A is a compound that generates an acid upon irradiation with actinic rays or radiation.

An acid generated from the photoacid generator A has a pKa of −1.00 or more (preferably −1.00 to 5.00, more preferably −0.50 to 3.00, and still more preferably 0.00 to 2.00).

In addition, the acid generated from the photoacid generator A is a compound represented by General Formula (I).

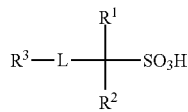

In Formula (1), $R^1$ and $R^2$ each independently represent a substituent that is not an electron-withdrawing group, or a hydrogen atom.

Examples of the substituent that is not the electron-withdrawing group include a hydrocarbon group, a hydroxyl group, an oxyhydrocarbon group, an oxycarbonyl hydrocarbon group, an amino group, a hydrocarbon-substituted amino group, and a hydrocarbon-substituted amido group.

Furthermore, it is preferable that the substituents which are not electron-withdrawing groups are each independently —R', —OH, —OR', —OCOR', —NH$_2$, —NR'$_2$, —NHR', or —NHCOR. R' is a monovalent hydrocarbon group.

Examples of the monovalent hydrocarbon group represented by R' include:

monovalent chain hydrocarbon groups such as alkyl groups such as a methyl group, an ethyl group, a propyl group, and a butyl group; alkenyl groups such as an ethenyl group, a propenyl group, and a butenyl group; and alkynyl group such as an ethynyl group, a propynyl group, and a butynyl group;

monovalent aliphatic hydrocarbon groups such as cycloalkyl groups such as a cyclopropyl group, a cyclobutyl group, a cyclopentyl group, a cyclohexyl group, a norbornyl group, and an adamantyl group; and cycloalkenyl groups such as a cyclopropenyl group, a cyclobutenyl group, a cyclopentenyl group, and a norbornenyl group; and monovalent aromatic hydrocarbon groups such as aryl groups such as a phenyl group, a tolyl group, a xylyl group, a mesityl group, a naphthyl group, a methylnaphthyl group, an anthryl group, and a methylanthryl group; and aralkyl groups such as a benzyl group, a phenethyl group, a phenylpropyl group, a naphthylmethyl group, and an anthrylmethyl group.

Among those, $R^1$ and $R^2$ are each independently preferably the hydrocarbon group (preferably a cycloalkyl group) or the hydrogen atom.

In General Formula (I), L represents a divalent linking group consisting of a combination of one or more linking groups S and one or more alkylene groups which may have a substituent, or a divalent linking group consisting of one or more linking groups S.

The linking group S is a group selected from the group consisting of $*^A$—O—CO—O—$*^B$, $*^A$—CO—$*^B$, $*^A$—COO$*^B$, $*^A$—O—CO—$*^B$, $*^A$—O—$*^B$, $*^A$—S—$*^B$, and $*^A$—SO$_2$—$*^B$.

It should be noted that in a case where L is "a divalent linking group consisting of a combination of one or more linking groups S and one or more alkylene groups which have no substituent, which is one form of "a divalent linking group consisting of a combination of one or more linking groups S and one or more alkylene groups which may have a substituent", the linking group S is a group selected from the group consisting of $*^A$—O—CO—O—$*^B$, $*^A$—CO—$*^B$, $*^A$—O—CO—$*^B$, $*^A$—O—$*^B$, $*^A$—S—$*^B$, and $*^A$—SO$_2$—$*^B$. In other words, in a case where the alkylene groups in the "divalent linking group consisting of a combination of one or more linking groups S and one or more alkylene groups which may have a substituent" are all unsubstituted alkylene groups, the linking group S is a group selected from the group consisting of $*^A$—O—CO—O—$*^B$, $*^A$—CO—$*^B$, $*^A$—O—CO—$*^B$, $*^A$—O—$*^B$, $*^A$—S—$*^B$, and $*^A$—SO$_2$—$*^B$.

$*^A$ represents a bonding position on the $R^3$ side in General Formula (I) and $*^B$ represents a bonding position on the —SO$_3$H side in General Formula (I).

In the divalent linking group consisting of a combination of one or more linking groups S and one or more alkylene groups which may have a substituent, only one linking group S may be present, or two or more linking groups S may be present. Similarly, with regard to the alkylene group which may have a substituent, only one alkylene group which may have a substituent may be present, or two or more alkylene groups may be present. In a case where the linking groups S are present in a plural number, the linking groups S that are present in a plural number may be the same as or different from each other. In a case where the alkylene groups are present in a plural number, the alkylene groups that are present in a plural number may be the same as or different from each other.

Furthermore, the linking groups S may be successively bonded to each other. It should be noted that it is preferable that groups selected from the group consisting of $*^A$—CO—$*^B$, $*^A$—O—CO—$*^B$, and $*^A$—O—$*^B$ are successively bonded not to form "$*^A$—O—CO—O—$*^B$". In addition, it is preferable that groups selected from the group consisting of $*^A$—CO—$*^B$ and $*^A$—O—$*^B$ are successively bonded not to form an of "$*^A$—O—CO—$*^B$" and "$*^A$—CO—O—$*^B$".

Also in the divalent linking group consisting of one or more linking groups S, only one linking group S may be present, or two or more linking groups S may be present. In a case where the linking groups S are present in a plural number, the linking groups S that are present in a plural number may be the same as or different from each other.

Also in this case, it is preferable that "$*^A$—O—CO—O—$*^B$" is not formed by the successive bonding of groups selected from the group consisting of $*^A$—CO—$*^B$, $*^A$—O—CO—$*^B$, and $*^A$—O—$*^B$. In addition, it is preferable that groups selected from the group consisting of $*^A$—CO—$*^B$ and $*^A$—O—$*^B$ are successively bonded not to form any of "$*^A$—O—CO—$*^B$" and "$*^A$—CO—O—$*^B$".

It should be noted that in any case, in L, an atom at the β-position with respect to —SO$_3$H is not a carbon atom having a fluorine atom as a substituent.

Furthermore, in a case where the atom at the β-position is a carbon atom, the carbon atom only needs to be not directly substituted with a fluorine atom, and the carbon atom may have a substituent having a fluorine atom (for example, a fluoroalkyl group such as a trifluoromethyl group).

In addition, the atom at the β-position is, in other words, the atom in L directly bonded to —C($R^1$)($R^2$)— in General Formula (I).

Above all, it is preferable that L has only one linking group S.

That is, it is preferable that L represents a divalent linking group consisting of a combination of one linking group S and one or more alkylene groups which may have a substituent, or a divalent linking group consisting of one linking group S.

L is preferably, for example, a group represented by General Formula (II).

$$*^a\text{—}(CR^{2a}{}_2)_X\text{-}Q\text{-}(CR^{2b}{}_2)_Y\text{—}*^b \quad (II)$$

In General Formula (II), $*^a$ represents a bonding position with $R^3$ in General Formula (I).

$*^b$ represents a bonding position with —C($R^1$)($R^2$)— in General Formula (I).

X and Y each independently represent an integer of 0 to 10, and is preferably an integer of 0 to 3.

$R^{2a}$ and $R^{2b}$ each independently represent a hydrogen atom or a substituent.

In a case where $R^{2a}$'s and $R^{2b}$'s are each present in a plural number, $R^{2a}$'s which are present in a plural number and $R^{2b}$'s which are present in a plural number may each be the same as or different from each other.

It should be noted that in a case where Y is 1 or more, $R^{2b}$ in $CR^{2b}{}_2$ which is directly bonded to —C($R^1$)($R^2$)— in General Formula (I) is other than a fluorine atom.

Q represents $*^A\text{—O—CO—O—}*^B$, $*^A\text{—CO—}*^B$, $*^A\text{—CO—O—}*^B$, $*^A\text{—O—CO—}*^B$, $*^A\text{—O—}*^B$, $*^A\text{—S—}*^B$, or $*^A\text{—SO}_2\text{—}*^B$.

It should be noted that in a case where X+Y in General Formula (II) is 1 or more and both of $R^{2a}$ and $R^{2b}$ in General Formula (II) are all hydrogen atoms, Q represents $*^A\text{—O—CO—O—}*^B$, $*^A\text{—CO—}*^B$, $*^A\text{—O—CO—}*^B$, $*^A\text{—O—}*^B$, $*^A\text{—S—}*^B$, or $*^A\text{—SO}_2\text{—}*^B$.

$*^A$ represents a bonding position on the $R^3$ side in General Formula (I) and $*^B$ represents a bonding position on the —SO$_3$H side in General Formula (I).

In General Formula (I), $R^3$ represents an organic group.

The organic group is not limited as long as it has one or more carbon atoms, may be a linear group (for example, a linear alkyl group such as a methyl group, an ethyl group, an n-propyl group, and an n-butyl group) or a branched group (for example, a branched alkyl group such as an isopropyl group and a t-butyl group), and may have a cyclic structure. The organic group may or may not have a substituent. The organic group may or may not have a heteroatom (a oxygen atom, a sulfur atom, a nitrogen atom, and/or the like).

Among those, $R^3$ is preferably an organic group having a cyclic structure. The cyclic structure may be a monocycle or a polycycle, and may have a substituent. The ring in the organic group containing a cyclic structure is preferably directly bonded to L in General Formula (I).

The organic group having a cyclic structure may or may not have, for example, a heteroatom (an oxygen atom, a sulfur atom, a nitrogen atom, and/or the like). The heteroatom may be substituted with one or more of carbon atoms forming the cyclic structure.

The organic group having a cyclic structure is preferably, for example, a hydrocarbon group with a cyclic structure, a lactone ring group, or a sultone ring group. Among those, the organic group having a cyclic structure is preferably a hydrocarbon group with a cyclic structure.

The hydrocarbon group with a cyclic structure is preferably a monocyclic or polycyclic cycloalkyl group. Such a group may have a substituent.

The cycloalkyl group may be a monocycle (a cyclohexyl group or the like) or a polycycle (an adamantyl group or the like), and preferably has 5 to 12 carbon atoms.

As the lactone group and the sultone group, for example, a group obtained by removing one hydrogen atom from one carbon atom constituting the lactone structure or the sultone structure in any of the structures represented by General Formulae (LC1-1) to (LC1-22) mentioned above and the structures represented by General Formulae (SL1-1) to (SL1-3) as described above is preferable.

In addition, it is preferable that the carbon atom from which one hydrogen atom is removed is not a carbon atom constituting the substituent (Rb$_2$).

The photoacid generator A is not particularly limited as long as an acid generated satisfies the above-mentioned requirements, and may be an onium salt compound or a zwitterion.

Among those, the photoacid generator A is preferably an onium salt compound having an anion and a cation.

The photoacid generator is preferably a compound represented by General Formula (ZaI) (compound (ZaI)) or a compound represented by General Formula (ZaI) (compound (ZaII)).

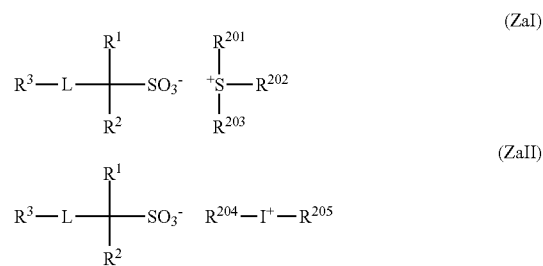

$R^1$, $R^2$, L, and $R^3$ have the same definitions as $R^1$, $R^2$, L, and $R^3$ in General Formula (I) mentioned above, respectively.

In General Formula (ZaI), $R^{201}$, $R^{202}$, and $R^{203}$ each independently represent an organic group.

The organic group as each of $R^{201}$, $R^{202}$, and $R^{203}$ usually has 1 to 30 carbon atoms, and preferably has 1 to 20 carbon atoms. In addition, two of $R^{201}$ to $R^{203}$ may be bonded to each other to form a ring structure, and the ring may include an oxygen atom, a sulfur atom, an ester group, an amido group, or a carbonyl group. Examples of the group formed by the bonding of two of $R^{201}$ to $R^{203}$ include an alkylene group (for example, a butylene group and a pentylene group), and —CH$_2$—CH$_2$—O—CH$_2$—CH$_2$—.

Suitable aspects of the cation in General Formula (ZaI) include corresponding groups in a compound (ZaI-1), a compound (ZaI-2), and a compound represented by General Formula (ZaI-3b) (compound (ZaI-3b)), and a compound represented by General Formula (ZaI-4b) (compound (ZaI-4b)), each of which will be described later.

Furthermore, the photoacid generator A may be a compound having a plurality of the structures represented by General Formula (ZaI). For example, it may be a compound having a structure in which at least one of $R^{201}$, $R^{202}$, or $R^{203}$ of a compound represented by General Formula (ZaI) and at least one of $R^{201}$, $R^{202}$, or $R^{203}$ of another compound represented by General Formula (ZaI) are bonded via a single bond or a linking group.

First, the compound (ZaI-1) will be described.

The compound (ZaI-1) is an arylsulfonium compound in which at least one of $R^{201}$, $R^{202}$, or $R^{203}$ in General Formula (ZaI) is an aryl group, that is, a compound having arylsulfonium as a cation.

In the arylsulfonium compound, all of $R^{201}$ to $R^{203}$ may be aryl groups, or some of $R^{201}$ to $R^{203}$ may be an aryl group, and the rest may be an alkyl group or a cycloalkyl group.

In addition, one of $R^{201}$ to $R^{203}$ may be an aryl group, two of $R^{201}$ to $R^{203}$ may be bonded to each other to form a ring structure, and an oxygen atom, a sulfur atom, an ester group, an amido group, or a carbonyl group may be included in the ring. Examples of a group formed by the bonding of two of $R^{201}$ to $R^{203}$ include an alkylene group (for example, a butylene group, a pentylene group, or —$CH_2$—$CH_2$—O—$CH_2$—$CH_2$—) in which one or more methylene groups are substituted with an oxygen atom, a sulfur atom, an ester group, an amido group, and/or a carbonyl group.

Examples of the arylsulfonium compound include a triarylsulfonium compound, a diarylalkylsulfonium compound, an aryldialkylsulfonium compound, a diarylcycloalkylsulfonium compound, and an aryldicycloalkylsulfonium compound.

As the aryl group included in the arylsulfonium compound, a phenyl group or a naphthyl group is preferable, and the phenyl group is more preferable. The aryl group may be an aryl group which has a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium compound has two or more aryl groups, the two or more aryl groups may be the same as or different from each other.

The alkyl group or the cycloalkyl group contained in the arylsulfonium compound, as necessary, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

The aryl group, the alkyl group, and the cycloalkyl group of each of $R^{201}$ to $R^{203}$ may each independently have an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a halogen atom, a hydroxyl group, or a phenylthio group as a substituent.

Next, the compound (ZaI-2) will be described.

The compound (ZaI-2) is a compound in which $R^{201}$ to $R^{203}$ in Formula (ZaI) each independently represent an organic group having no aromatic ring. Here, the aromatic ring also encompasses an aromatic ring including a heteroatom.

The organic group having no aromatic ring as each of $R^{201}$ to $R^{203}$ generally has 1 to 30 carbon atoms, and preferably 1 to 20 carbon atoms.

$R^{201}$ to $R^{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Preferred examples of the alkyl group and the cycloalkyl group of each of $R^{201}$ to $R^{03}$ include a linear alkyl group having 1 to 10 carbon atoms or a branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group).

$R^{201}$ to $R^{203}$ may be each further substituted with a halogen atom, an alkoxy group (for example, having 1 to 5 carbon atoms), a hydroxyl group, a cyano group, or a nitro group.

Next, the compound (ZaI-3b) will be described.

The compound (ZaI-3b) is a compound represented by General Formula (ZaI-3b) and having a phenacylsulfonium salt structure.

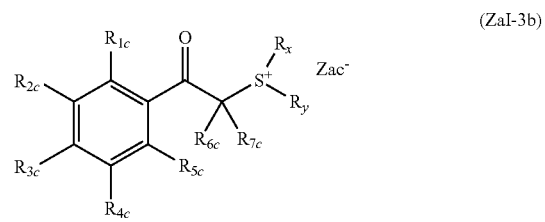

(ZaI-3b)

In General Formula (ZaI-3b), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ each independently represent a hydrogen atom, an alkyl group (a t-butyl group or the like), a cycloalkyl group, a halogen atom, a cyano group, or an aryl group.

$R_x$ and $R_y$ each independently represent an alkyl group, a cycloalkyl group, a 2-oxoalkyl group, a 2-oxocycloalkyl group, an alkoxycarbonylalkyl group, an allyl group, or a vinyl group.

Any two or more of $R_{1c}$, ..., or $R_{5c}$, $R_{5c}$ and $R_{6c}$, $R_{6c}$ and $R_{7c}$, $R_{5c}$ and $R_x$, and $R_x$ and $R_y$, may each be bonded to each other to form a ring, and the ring may each independently include an oxygen atom, a sulfur atom, a ketone group, an ester bond, or an amide bond.

Examples of the ring include an aromatic or non-aromatic hydrocarbon ring, an aromatic or non-aromatic heterocycle, and a polycyclic fused ring in which two or more of these rings are combined. Examples of the ring include a 3- to 10-membered ring, and the ring is preferably a 4- to 8-membered ring, and more preferably a 5- or 6-membered ring.

Examples of the group formed by the combination of any two or more of $R_{1c}$, ..., or $R_{5c}$, $R_{6c}$ and $R_{7c}$, and $R_x$ and $R_y$, include an alkylene group such as a butylene group and a pentylene group. The methylene group in this alkylene group may be substituted with a heteroatom such as an oxygen atom.

As the group formed by the combination of $R_{5c}$ and $R_{6c}$, and $R_{5c}$ and $R_x$, a single bond or an alkylene group is preferable. Examples of the alkylene group include a methylene group and an ethylene group.

$Zac^-$ has the same definition as "$R^3$-L-C($R^1$)($R^2$)—$SO_3^-$" in General Formula (ZaI).

Next, the compound (ZaI-4b) will be described.

The compound (ZaI-4b) is a compound represented by General Formula (ZaI-4b).

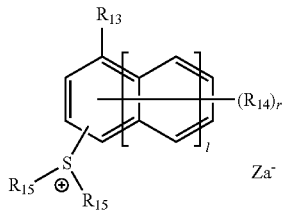

(ZaI-4b)

In General Formula (ZaI-4b), l represents an integer of 0 to 2.

r represents an integer of 0 to 8.

$R_{13}$ represents a hydrogen atom, a fluorine atom, a hydroxyl group, an alkyl group, an alkoxy group, an alkoxycarbonyl group, or a group having a cycloalkyl group (which may be the cycloalkyl group itself or a group including the cycloalkyl group in a part thereof). Such a group may have a substituent.

$R_{14}$ represents a hydroxyl group, an alkyl group, an alkoxy group, an alkoxycarbonyl group, an alkylcarbonyl group, an alkylsulfonyl group, a cycloalkylsulfonyl group, or a group having a cycloalkyl group (which may be the cycloalkyl group itself or a group including the cycloalkyl group in a part thereof). Such a group may have a substituent. In a case where $R_{14}$'s are present in a plural number, $R_{14}$'s each independently represent the group such as a hydroxyl group.

$R_{15}$'s each independently represent an alkyl group, a cycloalkyl group, or a naphthyl group. Such a group may have a substituent. Two $R_{15}$'s may be bonded to each other to form a ring. In a case where two $R_{15}$'s are bonded to each other to form a ring, the ring skeleton may include a heteroatom such as an oxygen atom and a nitrogen atom. In one aspect, it is preferable that two $R_{15}$'s are alkylene groups and are bonded to each other to form a ring structure.

$Za^-$ has the same definition as "$R^3$-L-C($R^1$)($R^2$)—$SO_3^-$" in General Formula (ZaI).

In General Formula (ZaI-4b), the alkyl groups of each of $R_{13}$, $R_{14}$, and $R_{15}$ are linear or branched. The alkyl group preferably has 1 to 10 carbon atoms. As the alkyl group, a methyl group, an ethyl group, an n-butyl group, a t-butyl group, or the like is more preferable.

Next, General Formula (ZaII) will be described.

In General Formula (ZaII), $R^{204}$ and $R^{205}$ each independently represent an aryl group, an alkyl group, or a cycloalkyl group.

As the aryl group of each of $R^{204}$ and $R^{205}$, a phenyl group or a naphthyl group is preferable, and the phenyl group is more preferable. The aryl group of each of $R^{204}$ and $R^{205}$ may be an aryl group which has a heterocycle having an oxygen atom, a nitrogen atom, a sulfur atom, or the like. Examples of the skeleton of the aryl group having a heterocycle include pyrrole, furan, thiophene, indole, benzofuran, and benzothiophene.

As the alkyl group and the cycloalkyl group of each of $R^{204}$ and $R^{205}$, a linear alkyl group having 1 to 10 carbon atoms or a branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group) is preferable.

The aryl group, the alkyl group, and the cycloalkyl group of each of $R^{204}$ and $R^{205}$ may each independently have a substituent. Examples of the substituent that the aryl group, alkyl group and cycloalkyl group of each of $R^{204}$ and $R^{205}$ may have include, for example, an alkyl group (for example, having 1 to 15 carbon atoms) and a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, and a phenylthio group.

"$R^3$-L-C($R^1$)($R^2$)—$SO_3^-$" in General Formula (ZaII) is an anion, and has the same definition as "$R^3$-L-C($R^1$)($R^2$)—$SO_3^-$" in General Formula (ZaI).

Preferred examples of anions and cations in a case where the photoacid generator A is an onium salt compound consisting of the anions and the cations are shown below.

Any combination of the cations and the anions can be used as the photoacid generator A.

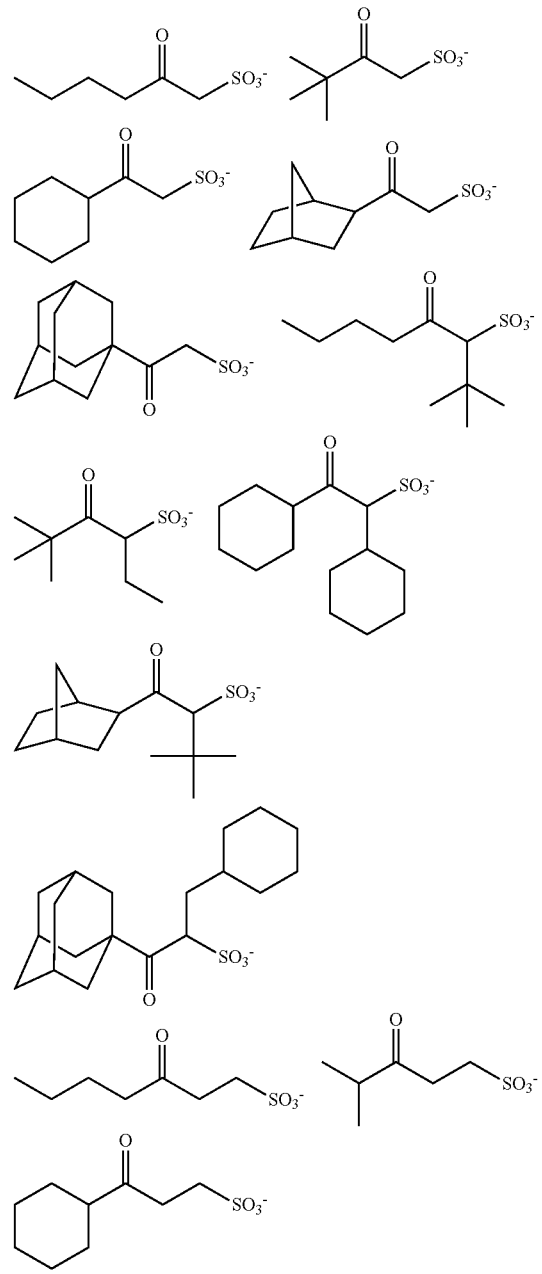

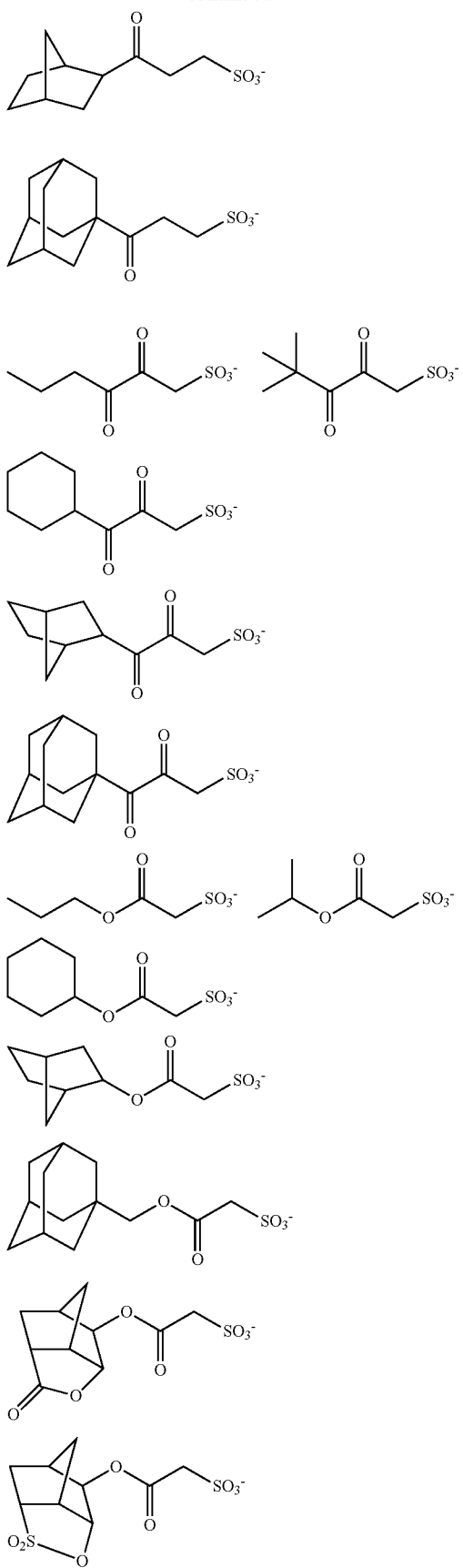
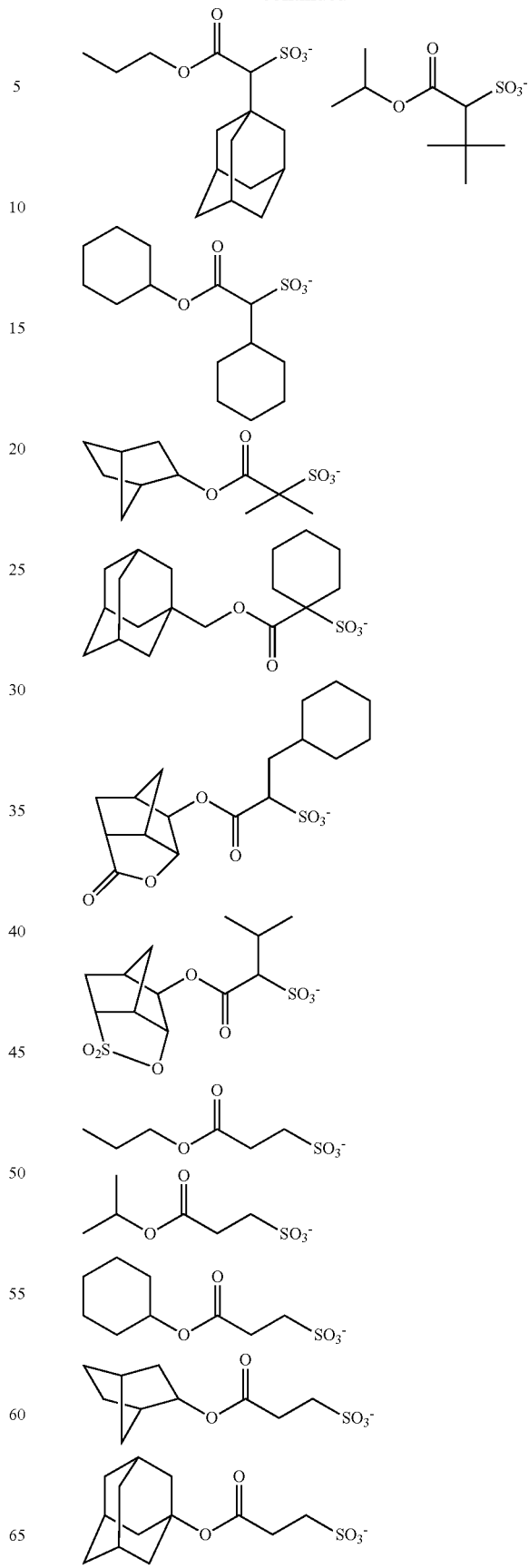

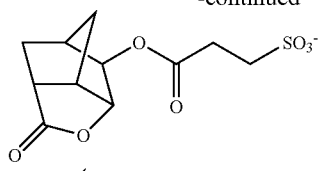
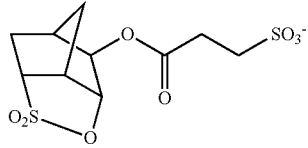
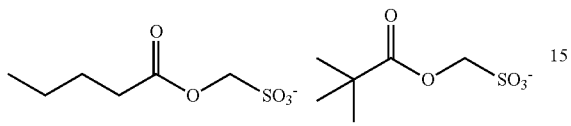
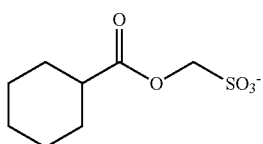
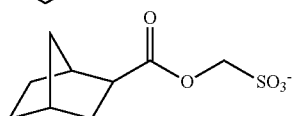
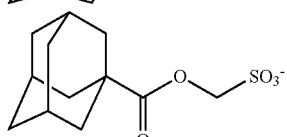
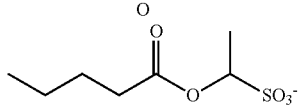
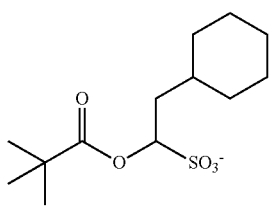
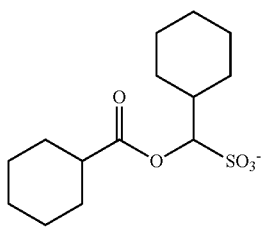
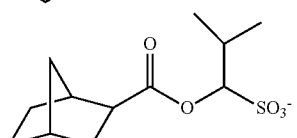
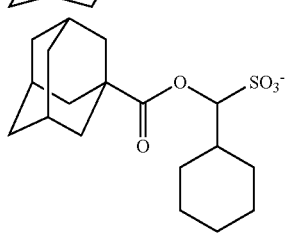
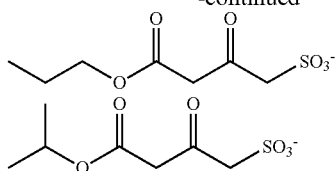
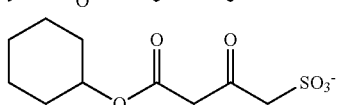
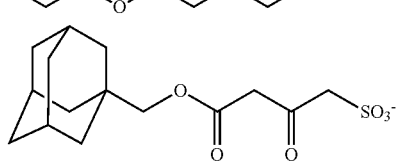
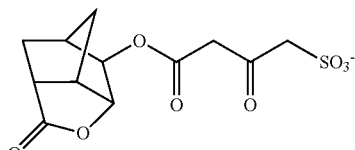
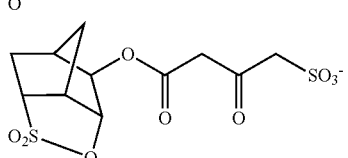
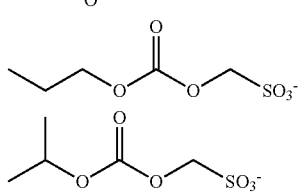
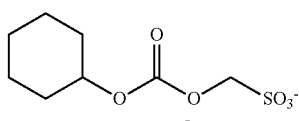
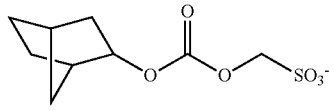
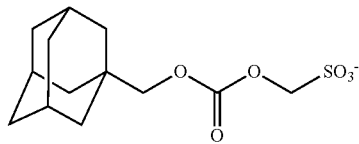
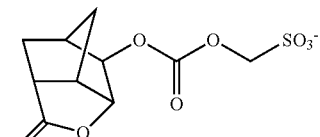
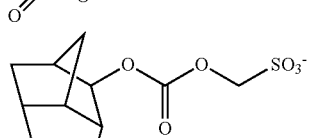
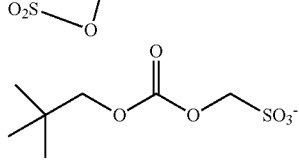

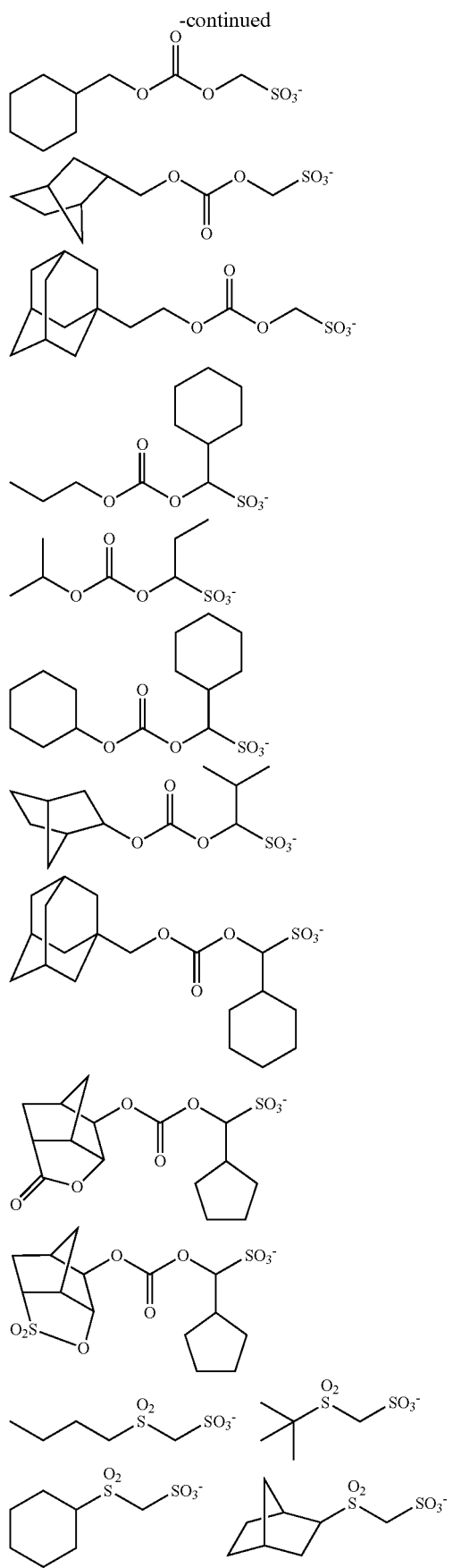
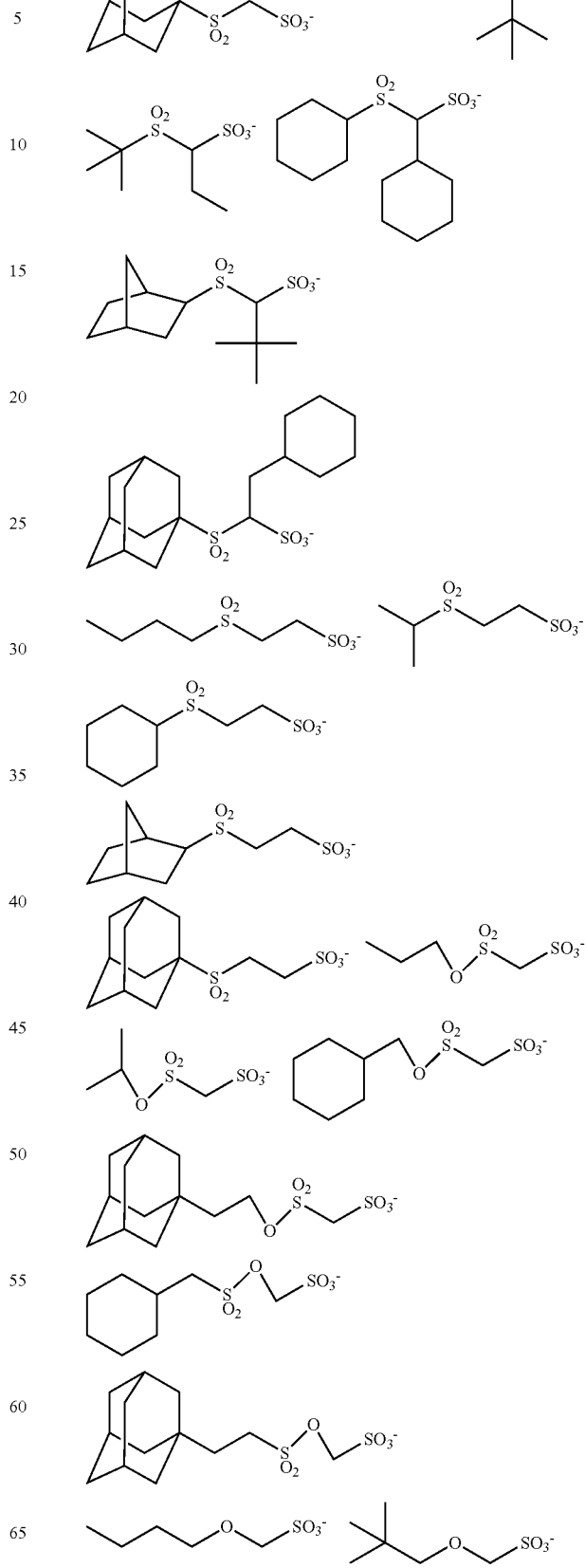

-continued
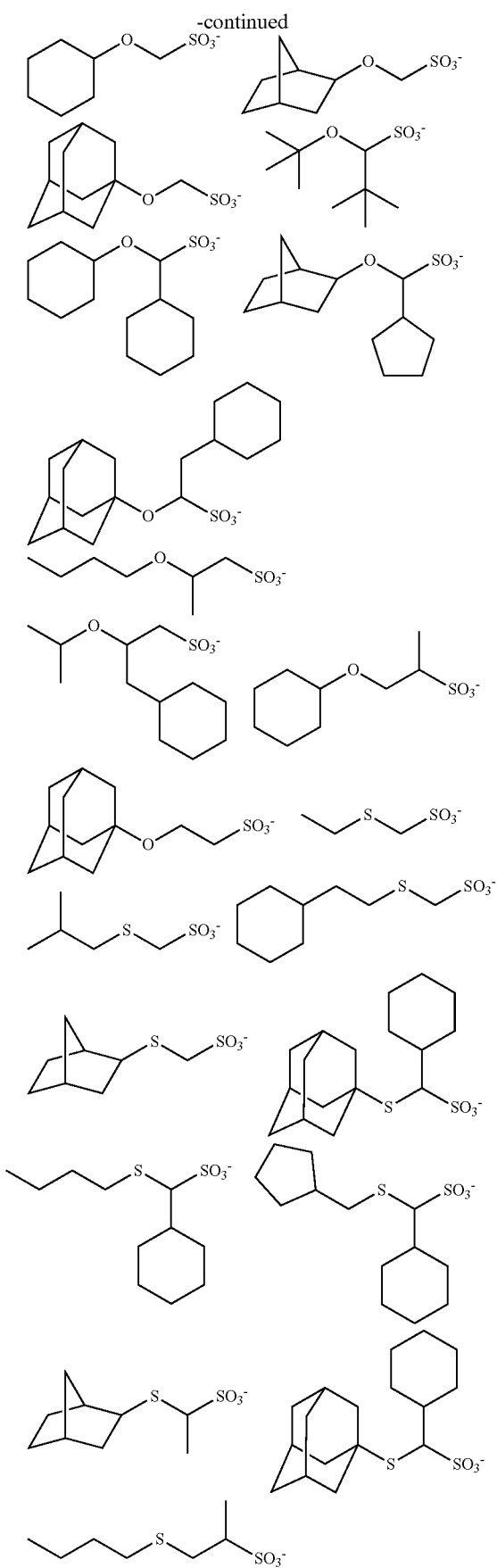
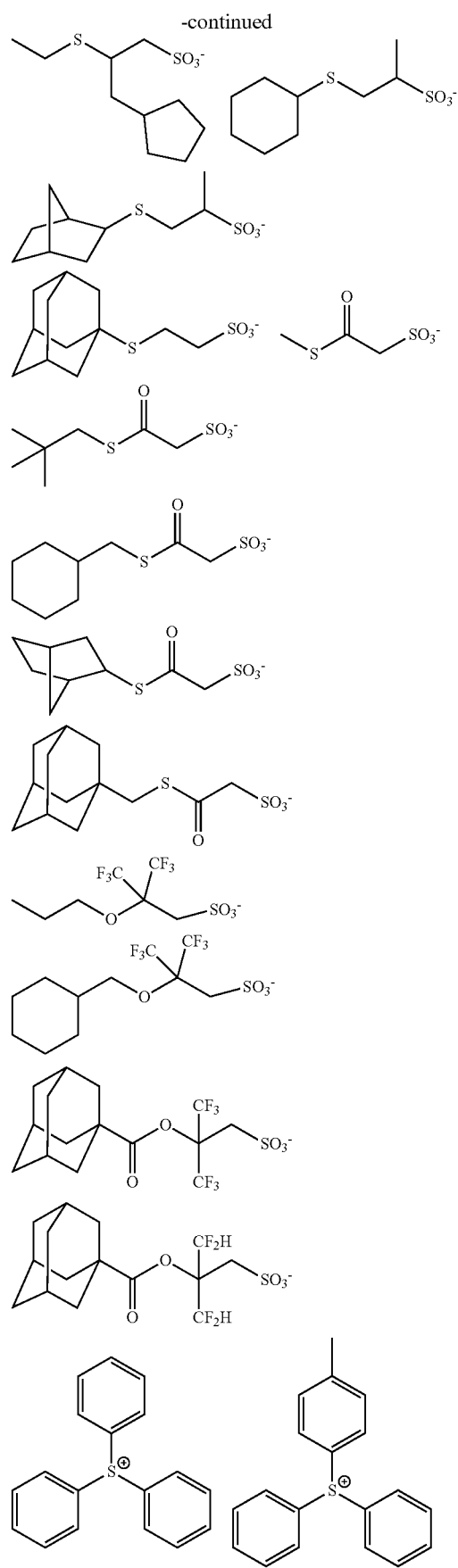

-continued
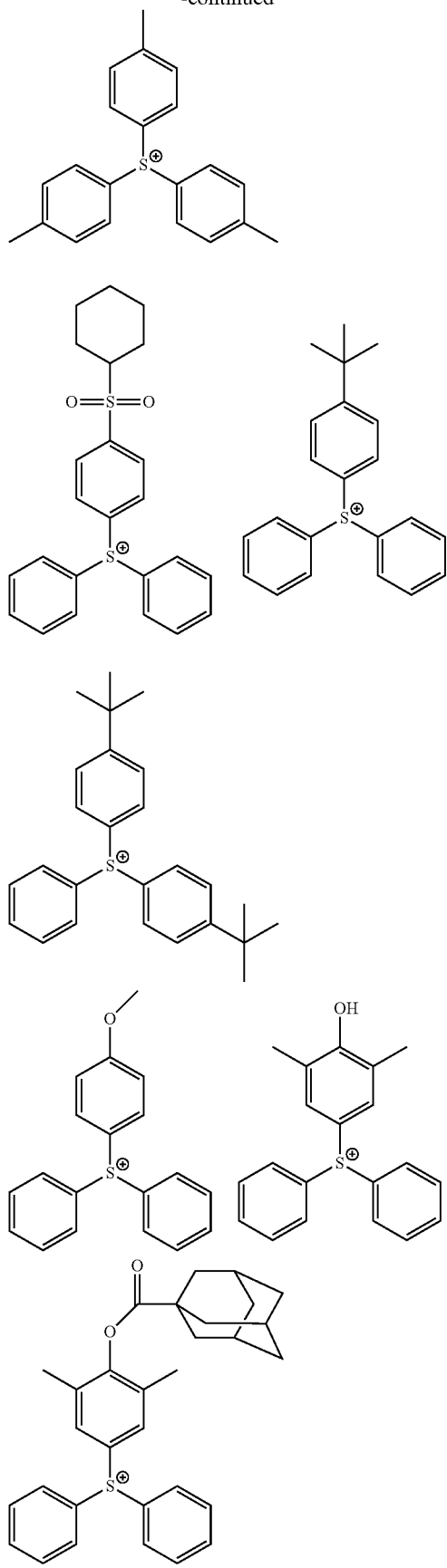
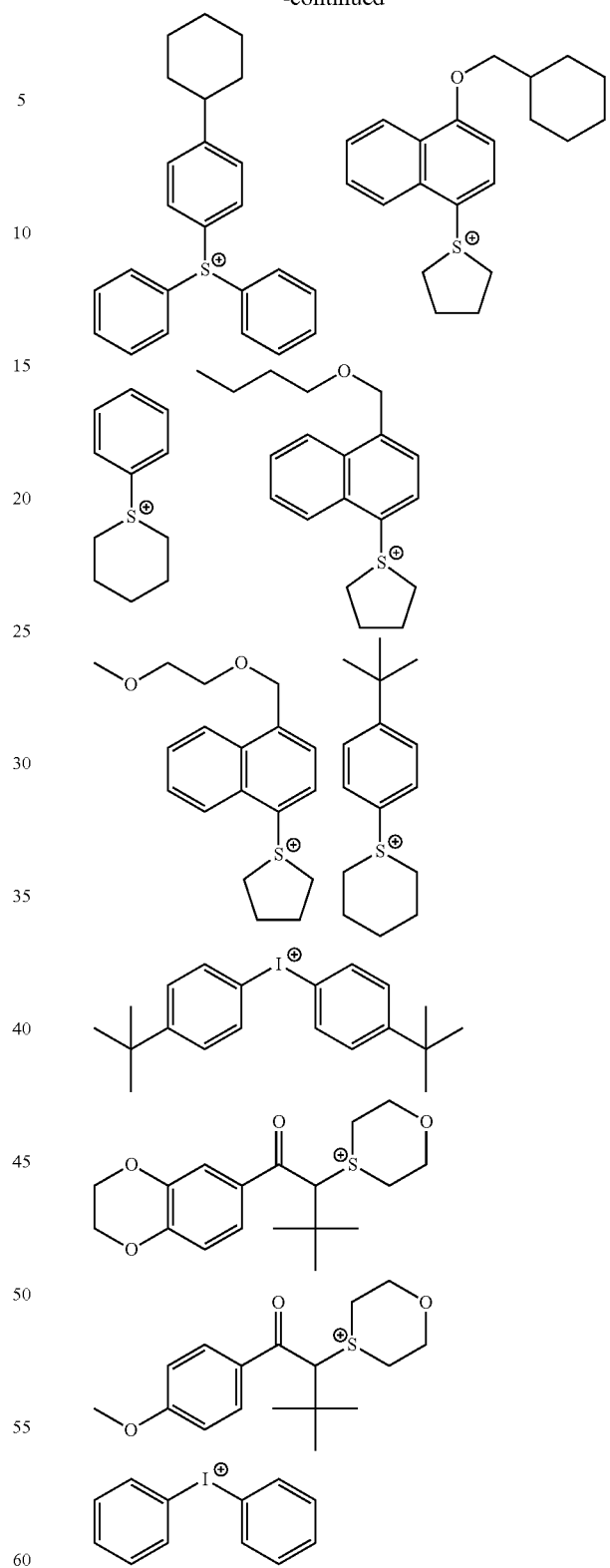
The photoacid generator A may be in a form of a low-molecular-weight compound or a form incorporated into a part of a polymer. Further, a combination of the form of a low-molecular-weight compound and the form incorporated into a part of a polymer may also be used.

The photoacid generator A is preferably in the form of a low-molecular-weight compound.

In a case where the photoacid generator is in the form of a low-molecular-weight compound, the molecular weight is preferably 3,000 or less, more preferably 2,000 or less, and still more preferably 1,000 or less.

The content of the photoacid generator A is preferably 0.1% to 35% by mass, more preferably 0.5% to 25% by mass, still more preferably 3% to 20% by mass, and particularly preferably 3% to 18% by mass, with respect to a total solid content of the composition.

The content of the photoacid generator A is preferably 0.01 to 1.00 mmol, more preferably 0.05 to 0.70 mmol, and still more preferably 0.10 to 0.40 mmol, with respect to 1 g of the solid content of the composition.

The photoacid generators A may be used singly or in combination of two or more kinds thereof. In a case where two or more kinds of the photoacid generators A are used, the total content thereof is preferably within the suitable content range.

<Photoacid Generator B>

The composition further includes at least one of a photoacid generator B or a nitrogen-containing compound C.

The photoacid generator B is a compound that generates an acid upon irradiation with actinic rays or radiation.

The photoacid generator B is a compound that generates an acid having a pKa larger than that of the acid generated from the photoacid generator by 1.00 or more.

The difference between the pKa of an acid generated from the photoacid generator B and the pKa of an acid generated from the photoacid generator A is preferably 1.00 to 12.00, more preferably 1.00 to 5.00, and still more preferably 1.00 to 3.00.

In addition, the pKa of the acid generated from the photoacid generator B varies depending on the type of the photoacid generator A used, but is, for example, preferably 0.00 to 12.00, more preferably 0.50 to 6.00, and still more preferably 1.00 to 4.00.

The photoacid generator B is preferably an onium salt compound consisting of an anion and a cation. As such the onium salt compound, compounds represented by General Formulae (d1-1) to (d1-3) are preferable.

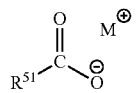

(d1-1)

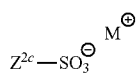

(d1-2)

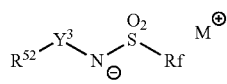

(d1-3)

In Formula (d1-1), $R^{51}$ represents a hydrocarbon group (for example, an aryl group such as a phenyl group) which may have a substituent (for example, a hydroxyl group).

In Formula (d1-2), $Z^{2c}$ represents a hydrocarbon group having 1 to 30 carbon atoms, which may have a substituent (provided that a carbon atom adjacent to S is not substituted with a fluorine atom).

The hydrocarbon group for $Z^{2c}$ may be linear or branched, and may have a cyclic structure. Further, the carbon atom in the hydrocarbon group (preferably the carbon atom forming a cyclic structure in a case where the hydrocarbon group has the cyclic structure) may be carbonyl carbon (—CO—). Examples of the hydrocarbon group include a group having a norbornyl group which may have a substituent. The carbon atom forming the norbornyl group may be carbonyl carbon.

In addition, it is preferable that "$Z^{2c}$—$SO_3^-$" in General Formula (d1-2) is different from "$R^3$-L-C($R^1$)($R^2$)—$SO_3^-$" in General Formula (1) mentioned above.

In Formula (d1-3), $R^{52}$ represents an organic group. The organic group is preferably an alkyl group, and more preferably an alkyl group having 1 to 10 carbon atoms. The alkyl group may be linear or branched, and may have a cyclic structure. As the substituent which may be contained in the alkyl group, a fluorine atom is preferable. The alkyl group may be a perfluoroalkyl group.

$Y^3$ represents a single bond, —CO—, an alkylene group, or an arylene group. The alkylene group may be linear or branched, and may have a cyclic structure. The alkylene group preferably has 1 to 7 carbon atoms. The arylene group preferably has 6 to 15 carbon atoms.

Rf represents a hydrocarbon group. The hydrocarbon group preferably has 1 to 30 carbon atoms. It may be linear or branched, and may have a cyclic structure. Further, the carbon atom in the hydrocarbon group (preferably the carbon atom forming a cyclic structure in a case where the hydrocarbon group has the cyclic structure) may be carbonyl carbon (—CO—). Examples of the hydrocarbon group include a group having a norbornyl group which may have a substituent. The carbon atom forming the norbornyl group may be carbonyl carbon. As the hydrocarbon group, an alkyl group such as a methyl group is also preferable.

Examples of the substituent which may be further contained in the hydrocarbon group include a fluorine atom.

In Formulae (d1-1) to (d1-3), $M^+$'s are each independently an ammonium cation, a sulfonium cation, or an iodonium cation.

As the sulfonium cation and the iodonium cation, for example, the sulfonium cation and the iodonium cation (more specifically the cations in a compound represented by General Formula (ZaI) and a compound represented by General Formula (ZaII)) in the cation which may be contained in the photoacid generator A can be similarly used.

The photoacid generator B may be a compound which has a cation site and an anion site in the same molecule, and has the cation site and the anion site linked by a covalent bond.

As the compound, a compound represented by General Formula (C-1) or a compound represented by General Formula (C-2) is preferable.

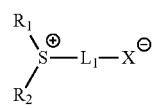

(C-1)

(C-2)

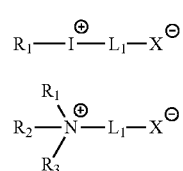

(C-3)

In General Formulae (C-1) to (C-3), $R_1$, $R_2$, and $R_3$ each independently represent a substituent having 1 or more carbon atoms.

L$_1$ represents a divalent linking group or a single bond that links a cationic group (S$^+$, I$^+$, or N$^+$) with —X$^+$.

—X$^-$ represents —COO$^-$, —SO$_3^-$—, —SO$_2^-$, or —N$^-$—R$_4$.

R$_4$ represents a monovalent substituent having at least one of a carbonyl group (—CO—), a sulfonyl group (—SO$_2$—), or a sulfinyl group (—S(=O)—) at a site for linking to an adjacent N atom.

R$_1$, R$_2$, R$_3$, R$_4$, and L$_1$ may be bonded to each other to form a ring.

In addition, in General Formula (C-3), two of R$_1$ to R$_3$ together represent one divalent substituent, and may be bonded to an N atom through a double bond.

Examples of the substituent having 1 or more carbon atoms in each of R$_1$ to R$_3$ include an alkyl group, a cycloalkyl group, an aryl group (preferably having 6 to 15 carbon atoms), an alkyloxycarbonyl group, a cycloalkyloxycarbonyl group, an aryloxycarbonyl group, an alkylaminocarbonyl group, a cycloalkylaminocarbonyl group, and an arylaminocarbonyl group. Among those, an alkyl group, a cycloalkyl group, or an aryl group is preferable.

Examples of L, as a divalent linking group include a linear or branched alkylene group, a cycloalkylene group, an arylene group (preferably having 6 to 15 carbon atoms), a carbonyl group, an ether bond, an ester bond, an amide bond, an urethane bond, an urea bond, and a group formed by combination of two or more of these groups. Among those, the alkylene group, the arylene group, the ether bond, the ester bond, or the group formed by combination of two or more of these groups is preferable.

The photoacid generator B is a compound that generates an acid having a pKa larger than that of the acid generated from the photoacid generator by 1.00 or more, and may be an onium salt compound having a nitrogen atom in the cationic moiety. The onium salt compound having a nitrogen atom in the cationic moiety preferably has a basic site including a nitrogen atom in the cationic moiety.

The basic site is preferably an amino group, and more preferably an aliphatic amino group. Further, all of the atoms adjacent to the nitrogen atom in the basic site are preferably hydrogen atoms or carbon atoms. In addition, from the viewpoint of improving basicity, it is preferable that an electron-withdrawing functional group (such as a carbonyl group, a sulfonyl group, a cyano group, and a halogen atom) is not directly linked to the nitrogen atom.

The acid generator B may be in a form of a low-molecular-weight compound or a form incorporated into a part of a polymer. Further, a combination of the form of a low-molecular-weight compound and the form incorporated into a part of a polymer may also be used.

The photoacid generator B is preferably in the form of a low-molecular-weight compound.

In a case where the photoacid generator B is in the form of a low-molecular-weight compound, the molecular weight is preferably 3,000 or less, more preferably 2,000 or less, and still more preferably 1,000 or less.

In a case where the photoacid generator B is included in the composition, the content thereof is preferably 0.1% to 15% by mass, more preferably 0.5% to 10% by mass, and still more preferably 1% to 5% by mass, with respect to a total solid content of the composition.

In a case where the photoacid generator B is included in the composition, the content thereof is preferably 0.005 to 0.50 mmol, more preferably 0.01 to 0.10 mmol, and still more preferably 0.01 to 0.05 mmol, with respect to 1 g of the solid content of the composition.

The photoacid generators B may be used singly or in combination of two or more kinds thereof. In a case where two or more photoacid generators B are used in the composition, the total content thereof is preferably within the suitable content range.

<Nitrogen-Containing Compound C>

The composition includes at least one of the photoacid generator B or a nitrogen-containing compound C.

The nitrogen-containing compound C is a compound which is different from the photoacid generator A.

The nitrogen-containing compound C is a compound which has at least one nitrogen atom and has a pKa of a conjugate acid thereof larger than that of the acid generated from the photoacid generator A by 1.00 or more.

The nitrogen-containing compound C may be a compound that generates an acid upon irradiation with actinic rays or radiation as long as it satisfies the requirement that the pKa of a conjugate acid is larger than that of the acid generated from the photoacid generator A by 1.00 or more.

Further, in a case where a compound has a nitrogen atom and has a pKa of a conjugate acid thereof larger than the acid generated from the photoacid generator A by 1.00 or more, even the compound that generates an acid having a pKa higher than that of the acid generated from the photoacid generator A by 1.00 or more corresponds to the nitrogen-containing compound C, but does not correspond to the photoacid generator B.

It is preferable that the nitrogen atom contained in the nitrogen-containing compound C is other than a nitrogen anion (N$^-$) and/or a nitrogen cation (N$^+$). That is, even in a case where the nitrogen-containing compound includes the nitrogen anion (N$^-$) and/or the nitrogen cation (N$^+$), it is preferable that the nitrogen-containing compound further has a nitrogen atom other than the nitrogen anion (N$^-$) and/or the nitrogen cation (N$^+$).

A difference between the pKa of the conjugate acid of the nitrogen-containing compound C and the pKa of the acid generated from the photoacid generator A is preferably 1.00 to 14.00, more preferably 2.00 to 13.00, and still more preferably 3.00 to 12.00.

In addition, the pKa of the conjugate acid of the nitrogen-containing compound C varies depending on the type of the photoacid generator A used, but is preferably 0.00 to 14.00, more preferably 3.00 to 13.00, and still more preferably 3.50 to 12.50.

The nitrogen-containing compound C acts as a quencher that suppresses a reaction of the acid-decomposable resin in the unexposed area by excessive generated acids by trapping the acids generated from the photoacid generator A and the like upon exposure.

Examples of the nitrogen-containing compound C include a basic compound (DA) having a nitrogen atom, a basic compound (DB) having a nitrogen atom, which has a basicity reduced or eliminated by irradiation with actinic rays or radiation, a low-molecular-weight compound (DD) having a nitrogen atom, which has a group that is eliminated by the action of an acid, and an onium salt compound (DE) having a nitrogen atom in a cationic moiety.

(Basic Compound (DA))

As the basic compound (DA), compounds having structures represented by General Formulae (A) to (E) are preferable.

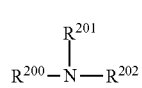

(A)

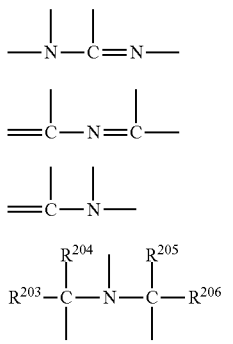

(B)

(C)

(D)

(E)

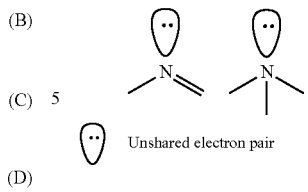

⊙ Unshared electron pair

In General Formulae (A) and (E), $R^{200}$, $R^{201}$, and $R^{202}$ may be the same as or different from each other, and each independently represent a hydrogen atom, an alkyl group (preferably having 1 to 20 carbon atoms), a cycloalkyl group (preferably having 3 to 20 carbon atoms), or an aryl group (preferably having 6 to 20 carbon atoms). $R^{201}$ and $R^{202}$ may be bonded to each other to form a ring.

$R^{203}$, $R^{204}$, $R^{205}$, and $R^{206}$ may be the same as or different from each other and each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl group in each of General Formulae (A) and (E) is more preferably unsubstituted.

As the basic compound (DA), guanidine, aminopyrrolidine, pyrazole, pyrazoline, piperazine, aminomorpholine, aminoalkylmorpholine, piperidine, or the like is preferable; and a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether group, an aniline derivative having a hydroxyl group and/or an ether group, or the like is more preferable.

(Compound (DB))

The nitrogen-containing compound C may be a basic compound (DB) (hereinafter also referred to as a "compound (DB)") having a nitrogen atom, which has a basicity reduced or eliminated by irradiation with actinic rays or radiation. The compound (DB) is a compound which has a proton-accepting functional group and decomposes under irradiation with actinic rays or radiation to exhibit deterioration in proton-accepting properties, no proton-accepting properties, or a change from the proton-accepting properties to acidic properties.

The proton-accepting functional group refers to a functional group having a group or an electron which is capable of electrostatically interacting with a proton, and for example, means a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following formula.

Preferred examples of the partial structure of the proton-accepting functional group include crown ether, azacrown ether, primary to tertiary amines, pyridine, imidazole, and pyrazine structures.

The compound (DB) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease in the equilibrium constant at chemical equilibrium in a case where a proton adduct is generated from the compound (DB) having the proton-accepting functional group and the proton.

The proton-accepting properties can be confirmed by performing pH measurement.

The pKa of the compound generated by decomposition of the compound (DB) upon irradiation with actinic rays or radiation preferably is pKa<−1, more preferably −13<pKa<−1, and still more preferably 13<pKa<−3.

The compound thus generated may undergo intramolecular neutralization to have a pKa of −1 or more.

The compound (DB) is preferably a compound represented by General Formula (c-1).

$$R-B-X-A-W_1-N^--W_2-R_f[C^+] \quad (c\text{-}1)$$

In General Formula (c-1), $W_1$ and $W_2$ each independently represent —$SO_2$— or —CO—.

$R_f$ represents an alkyl group which may have a substituent, a cycloalkyl group which may have a substituent, or an aryl group which may have a substituent.

A represents a single bond or a divalent linking group.

X represents a single bond, —$SO_2$—, or —CO—.

B represents a single bond, an oxygen atom, or —N(Rx)Ry-.

Rx represents a hydrogen atom or an organic group.

Ry represents a single bond or a divalent organic group.

R represents an organic group having a proton-accepting functional group.

Rx may be bonded to Ry to form a ring, and may be bonded to R to form a ring.

[C$^+$] represents a counter cation.

It is preferable that at least one of $W_1$ or $W_2$ is —$SO_2$—, and it is more preferable that the both are —$SO_2$—.

$R_f$ is preferably an alkyl group having 1 to 6 carbon atoms, which may have a fluorine atom, more preferably a perfluoroalkyl group having 1 to 6 carbon atoms, and still more preferably a perfluoroalkyl group having 1 to 3 carbon atoms.

The divalent linking group for A is preferably a divalent linking group having 2 to 12 carbon atoms, and examples thereof include an alkylene group and a phenylene group. Among those, an alkylene group having at least one fluorine atom is preferable, and the alkylene group preferably has 2 to 6 carbon atoms, and more preferably has 2 to 4 carbon atoms. The alkylene chain may have a linking group such as an oxygen atom or a sulfur atom. The alkylene group is preferably an alkylene group in which 30% to 100% of the hydrogen atoms have been substituted with fluorine atoms, and more preferably an alkylene group in which the carbon atom bonded to the X and/or $W_1$ site has a fluorine atom. Among those, the divalent linking group for A is preferably a perfluoroalkylene group, and more preferably a perfluoroethylene group, a perfluoropropylene group, or a perfluorobutylene group.

In a case where B represents —N(Rx)Ry-, the organic group for $R_x$ preferably has 2 to 30 carbon atoms, and examples thereof include an alkyl group, a cycloalkyl group which may have an oxygen atom in the ring, an aryl group, an aralkyl group, and an alkenyl group.

The alkyl group for $R_x$ may have a substituent, and is preferably a linear or branched alkyl group having 1 to 20 carbon atoms, and an oxygen atom, a sulfur atom, and/or a nitrogen atom may be contained in the alkyl chain.

Furthermore, examples of the alkyl group having a substituent include a linear or branched alkyl group substituted with a cycloalkyl group (for example, an adamantylmethyl group, an adamantylethyl group, a cyclohexylethyl group, and a camphor residue).

The cycloalkyl group for $R_x$ may have a substituent and is preferably a cycloalkyl group having 3 to 20 carbon atoms. Further, the cycloalkyl group may have an oxygen atom in the ring.

The aryl group for $R_x$ may have a substituent, and is preferably an aryl group having 6 to 14 carbon atoms.

The aralkyl group for $R_x$ may have a substituent, and is preferably an aralkyl group having 7 to 20 carbon atoms.

The alkenyl group for $R_x$ may have a substituent, and examples thereof include a group having a double bond at any position of the alkyl group mentioned as $R_x$.

In a case where B represents —N($R_x$)$R_y$—, the divalent organic group for $R_y$ is preferably an alkylene group. Further, in this case, examples of the ring formed by the mutual bonding of $R_x$ and $R_y$ include a 5- to 8-membered ring including a nitrogen atom, and particularly preferably a 6-membered ring. The nitrogen atom included in the ring may be a nitrogen atom other than the nitrogen atom directly bonded to X in —N($R_x$)$R_y$—.

In a case where B represents —N($R_x$)$R_y$—, it is preferable that R and $R_x$ are bonded to each other to form a ring. In a case of forming a ring, stability is improved, and the storage stability of a composition using the same ring structure is improved. The number of carbon atoms forming the ring is preferably 4 to 20 and may be either a monocycle or a polycycle, and the ring may include an oxygen atom, a sulfur atom and/or a nitrogen atom. The nitrogen atom included in the ring may be a nitrogen atom other than the nitrogen atom directly bonded to X in —N($R_x$)$R_y$—.

Examples of the monocycle include a 4-membered ring, a 5-membered ring, a 6-membered ring, a 7-membered ring, and an 8-membered ring, each of which includes a nitrogen atom. Examples of such a ring structure include a piperazine ring and a piperidine ring. The polycycle includes a structure constituted with a combination of 2 or 3 or more monocyclic structures. Each of the monocycle and the polycycle may have a substituent, which is preferably a halogen atom, a hydroxyl group, a cyano group, a carboxyl group, a carbonyl group, a cycloalkyl group (preferably having 3 to 10 carbon atoms), an aryl group (preferably having 6 to 14 carbon atoms), an alkoxy group (preferably having 1 to 10 carbon atoms), an acyl group (preferably having 2 to 15 carbon atoms), an acyloxy group (preferably having 2 to 15 carbon atoms), an alkoxycarbonyl group (preferably having 2 to 15 carbon atoms), an aminoacyl group (preferably 2 to 20 carbon atoms), or a lactone ring group (preferably a group formed by removing one hydrogen atom from a lactone structure represented by any of General Formulae (LC1-1) to (LC1-22) mentioned above). These substituents may have a substituent where available. In a case where the aryl group and the cycloalkyl group each further have a substituent, examples of the substituent include an alkyl group (preferably having 1 to 15 carbon atoms). Examples of the substituent which may be further contained in the aminoacyl group include an alkyl group (preferably having 1 to 15 carbon atoms).

The proton-accepting functional group in R is as described above, and preferably has, as a partial structure thereof, a structure of, for example, a crown ether, primary to tertiary amines, and a nitrogen-containing heterocycle (pyridine, imidazole, pyrazine, and the like).

Furthermore, as the proton-accepting functional group, a functional group having a nitrogen atom is preferable, and a group having a primary to tertiary amino group or a nitrogen-containing heterocyclic group is more preferable. In these structures, it is preferable that all of the atoms adjacent to the nitrogen atom included in the structure are carbon atoms or hydrogen atoms. In addition, it is preferable that an electron-withdrawing functional group (such as a carbonyl group, a sulfonyl group, a cyano group, and a halogen atom) is not directly linked to the nitrogen atom.

The organic group for the organic group (the group R) including such a proton-accepting functional group preferably has 2 to 30 carbon atoms, examples thereof include an alkyl group, a cycloalkyl group, an aryl group, an aralkyl group, and an alkenyl group, and each of the groups may have a substituent.

In the alkyl group, the cycloalkyl group, the aryl group, the aralkyl group, and the alkenyl group, each of which includes a proton-accepting functional group in R, examples of the alkyl group, the cycloalkyl group, the aryl group, the aralkyl group, and the alkenyl group include the same groups as those of the alkyl group, the cycloalkyl group, the aryl group, the aralkyl group, and the alkenyl group mentioned as $R_x$, respectively.

The substituent which may be contained in each of the groups include a halogen atom, a hydroxyl group, a nitro group, a cyano group, a carboxyl group, a cycloalkyl group (preferably having 3 to 10 carbon atoms; a part of the group may be substituted with a heteroatom or a group having a heteroatom (an ester group or the like)), an aryl group (preferably having 6 to 14 carbon atoms), an alkoxy group (preferably having 1 to 10 carbon atoms), an acyl group (preferably having 2 to 20 carbon atoms), an acyloxy group (preferably having 2 to 10 carbon atoms), an alkoxycarbonyl group (preferably having 2 to 20 carbon atoms), and an aminoacyl group (preferably having 2 to 20 carbon atoms). Examples of the substituent which may be contained in the cyclic group in the aryl group, the cycloalkyl group, and the like include an alkyl group (preferably having 1 to 20 carbon atoms). Examples of the substituent which is contained in the aminoacyl group include 1 or 2 alkyl groups (preferably having 1 to 20 carbon atoms).

[$C^+$] is preferably a sulfonium cation or an iodonium cation as a counter cation. As the sulfonium cation and the iodonium cation, for example, a sulfonium cation and an iodonium cation for the cation which may be contained in the photoacid generator A (more specifically the cation in the compound represented by General Formula (ZaI), the cation in the compound represented by General Formula (ZaII), or the like) can be similarly used.

(Compound (DD))

The nitrogen-containing compound C may be a low-molecular-weight compound (DD) having a nitrogen atom and a group that is eliminated by the action of an acid (hereinafter also referred to as a "compound (DD)"). The compound (DD) is preferably an amine derivative having, on the nitrogen atom, a group that is eliminated by the action of an acid.

As the group that is eliminated by the action of an acid, an acetal group, a carbonate group, a carbamate group, a tertiary ester group, a tertiary hydroxyl group, or a hemiaminal ether group is preferable, and the carbamate group or the hemiaminal ether group is more preferable.

The molecular weight of the compound (DD) is preferably 100 to 1,000, more preferably 100 to 700, and still more preferably 100 to 500.

The compound (DD) may have a carbamate group having a protective group on the nitrogen atom. The protective group constituting the carbamate group is preferably a group represented by General Formula (d-1).

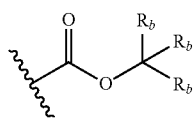

(d-1)

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably 1 to 10 carbon atoms). $R_b$'s may be linked to each other to form a ring.

The alkyl group, a cycloalkyl group, aryl group, and aralkyl group represented by $R_b$ may be each independently substituted with a hydroxyl group, a cyano group, an amino group, a pyrrolidino group, a piperidino group, a morpholino group, an oxo group, or another functional group, an alkoxy group, or a halogen atom. The same applies to the alkoxyalkyl group represented by $R_b$.

$R_b$ is preferably a linear or branched alkyl group, a cycloalkyl group, or an aryl group, and more preferably the linear or branched alkyl group, or the cycloalkyl group.

Examples of the ring formed by the mutual linking of two of $R_b$'s include an alicyclic hydrocarbon, an aromatic hydrocarbon, a heterocyclic hydrocarbon, and derivatives thereof.

Examples of the specific structure of the group represented by General Formula (d-1) include, but are not limited to, the structures disclosed in paragraph <0466> of the specification of US2012/0135348A1.

The compound (DD) is preferably a compound having a structure represented by General Formula (6).

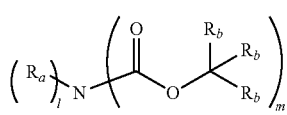

(6)

In General Formula (6), l represents an integer of 0 to 2, m represents an integer of 1 to 3, and these satisfy l+m=3.

$R_a$ represents a hydrogen atom, an alkyl group, a cycloalkyl group, an aryl group, or an aralkyl group. In a case where l is 2, two of $R_a$'s may be the same as or different from each other, and the two of $R_a$'s may be linked to each other to form a heterocycle with the nitrogen atom in the formula. This heterocycle may include a heteroatom other than the nitrogen atom in the formula.

$R_b$ has the same definition as $R_b$ in General Formula (d-1), and preferred examples are also the same.

In General Formula (6), the alkyl group, the cycloalkyl group, the aryl group, and the aralkyl group as $R_a$ may be substituted with the same groups as the group mentioned above as a group which may be each independently substituted in the alkyl group, the cycloalkyl group, the aryl group, and the aralkyl group as $R_b$.

Specific examples of the alkyl group, the cycloalkyl group, the aryl group, and the aralkyl group (these groups may be substituted with the groups as described above) of $R_a$ include the same groups as the specific examples as described above with respect to $R_b$.

(Compound (DE))

The nitrogen-containing compound C may be an onium salt compound (DE) having a nitrogen atom in the cationic moiety (hereinafter also referred to as a "compound (DE)"). However, in a case where the compound (DE) generates an acid upon irradiation with actinic rays or radiation, the pKa of an acid generated is smaller than a value obtained by adding 1 to the pKa of an acid generated from the photoacid generator A.

The compound (DE) is preferably a compound having a basic site including a nitrogen atom in the cationic moiety.

The basic site is preferably an amino group, and more preferably an aliphatic amino group. Further, all of the atoms adjacent to the nitrogen atom in the basic site are preferably hydrogen atoms or carbon atoms. In addition, from the viewpoint of improving basicity, it is preferable that an electron-withdrawing functional group (such as a carbonyl group, a sulfonyl group, a cyano group, and a halogen atom) is not directly linked to the nitrogen atom.

In a case where the composition contains the nitrogen-containing compound C, the content of the nitrogen-containing compound C in the composition is preferably 0.1% to 15% by mass, more preferably 0.1% to 10% by mass, and more preferably 0.5% to 8.0% by mass, with respect to the total solid content of the composition.

The nitrogen-containing compounds C may be used singly or in combination of two or more kinds thereof. In a case where two or more kinds of the nitrogen-containing compounds C are used in the composition, the total content thereof is preferably within the suitable content range.

The composition only needs to include at least one selected from the group consisting of the photoacid generator B and the nitrogen-containing compound C, and may include only one or both of them.

<Photoacid Generator D>

The composition of the embodiment of the present invention may or may not include a photoacid generator D that generates an acid having a pKa of less than −1.00.

It should be noted that the photoacid generator D is a compound different from the above-mentioned nitrogen-containing compound C.

That is, even a compound that generates an acid having a pKa of less than −1.00 upon irradiation with actinic rays or radiation corresponds to the nitrogen-containing compound C as long as the compound has a nitrogen atom and has a pKa of a conjugate acid thereof larger than the acid generated from the photoacid generator A by 1.00 or more, but does not correspond to the photoacid generator D.

In a case where the composition includes the photoacid generator D, a ratio of the number of moles of the photoacid generator A to the number of moles of the photoacid generator D in the composition (the content of the photoacid generator A/the content of the photoacid generator D (molar ratio) is 1.0 or more, preferably 1.5 or more, more preferably 2.0 or more, still more preferably 5.0 or more, and particularly preferably 10 or more. An upper limit thereof is not particularly limited, but is, for example, 20 or less.

In a case where the composition includes the photoacid generator D, the content of the photoacid generator D is preferably 15% by mass or less, more preferably 7% by mass or less, still more preferably 4% by mass or less, and particularly preferably 1% by mass or less, with respect to the total solid content of the composition. A lower limit thereof is not particularly limited, but is, for example, 0.1% by mass or more.

In a case where the composition includes the photoacid generator D, the content of the photoacid generator D is preferably 0.13 mmol or less, more preferably 0.10 mmol or less, still more preferably 0.07 mmol or less, and particularly preferably 0.03 mmol or less, with respect to 1 g of the solid content of the composition. A lower limit thereof is not particularly limited, but is, for example, 0.001 mmol or more.

<Hydrophobic Resin>

The composition of the embodiment of the present invention may include a hydrophobic resin. Further, the hydrophobic resin is preferably a resin different from the resin A.

In a case where the composition of the embodiment of the present invention includes the hydrophobic resin, it is easy to control the static and/or dynamic contact angle on the surface of a resist film (actinic ray-sensitive or radiation-sensitive film). Thus, it is possible to improve development characteristics, suppress generation of out gas, improve immersion liquid tracking properties upon liquid immersion exposure, and reduce liquid immersion defects, for example.

It is preferable that the hydrophobic resin is designed to be unevenly distributed on a surface of a resist film, but unlike the surfactant, the hydrophobic resin does not necessarily have a hydrophilic group in a molecule thereof and may not necessarily contribute to homogeneous mixing of polar materials and non-polar materials.

The hydrophobic resin is preferably a resin having a repeating unit having at least one selected from the group consisting of a "fluorine atom", a "silicon atom", or a "CH$_3$ partial structure which is included in a side chain portion of a resin" from the viewpoint of uneven distribution on a film surface layer.

In a case where the hydrophobic resin includes a fluorine atom and/or a silicon atom, the fluorine atom and/or the silicon atom described above in the hydrophobic resin may be included in the main chain of a resin or may be included in a side chain.

In a case where the hydrophobic resin includes a fluorine atom, it is preferably a resin which has an alkyl group having a fluorine atom, a cycloalkyl group having a fluorine atom, or an aryl group having a fluorine atom as a partial structure having a fluorine atom.

The hydrophobic resin preferably has at least one group selected from the following (x) to (z) groups:

(x) an acid group,
(y) a group having a solubility in an alkali developer that increases through decomposition by the action of the alkali developer (hereinafter also referred to as a polarity conversion group), and
(z) a group that decomposes by the action of an acid.

Examples of the acid group (x) include a phenolic hydroxyl group, a carboxyl group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group. As the acid group, the fluorinated alcohol group (preferably hexafluoroisopropanol group), the sulfonimido group, or the bis(alkylcarbonyl)methylene group is preferable.

Examples of the group (y) having a solubility in an alkali developer that increases through decomposition by the action of the alkali developer include a lactone group, a carboxyester group (—COO—), an acid anhydride group (—CO—O—CO—), an acid imido group (—NHCONH—), a carboxythioester group (—COS—), a carbonate ester group (—O—CO—O—), a sulfuric ester group (—OSO$_2$O—), and a sulfonic ester group (—SO$_2$O—), and the lactone group or the carboxyester group (—COO—) is preferable.

The repeating unit including such the group is, for example, a repeating unit in which the group is directly bonded to the main chain of a resin, and examples thereof include a repeating unit with an acrylic ester or a methacrylic ester. In this repeating unit, such the group may be bonded to the main chain of the resin via a linking group. Alternatively, this repeating unit may also be incorporated into a terminal of the resin by using a polymerization initiator or a chain transfer agent having such the group during polymerization.

Examples of the repeating unit having a lactone group include the same repeating units as the repeating unit having a lactone structure described earlier in the section of the resin A.

In a case where the hydrophobic resin has a repeating unit having the group (y) having a solubility in an alkali developer that increases through decomposition by the action of the alkali developer, the content of the repeating unit is preferably 1% to 100% by mole, more preferably 3% to 98% by mole, and still more preferably 5% to 95% by mole, with respect to all the repeating units in the hydrophobic resin.

Examples of the repeating unit having the group (z) that decomposes by the action of an acid in the hydrophobic resin include the same repeating units as the repeating units having an acid-decomposable group exemplified in the resin A. The repeating unit having a group (z) that decomposes by the action of an acid may have at least any one of a fluorine atom or a silicon atom. In a case where the hydrophobic resin has the repeating unit having a group (z) that decomposes by the action of an acid, the content of the repeating unit is preferably 1% to 80% by mole, more preferably 10% to 80% by mole, and still more preferably 15% to 60% by mole, with respect to all the repeating units in the hydrophobic resin.

The hydrophobic resin may further have a repeating unit which is different from the above-mentioned repeating units.

In a case where the hydrophobic resin has a repeating unit including a fluorine atom, the content of the repeating unit is preferably 10% to 100% by mole, and more preferably 30% to 100% by mole, with respect to all the repeating units in the hydrophobic resin. In addition, in a case where the hydrophobic resin has a repeating units including a silicon atom, the content of the repeating unit is preferably 10% to 100% by mole, and more preferably 20% to 100% by mole, with respect to all the repeating units in the hydrophobic resin.

On the other hand, in a case where the hydrophobic resin includes a CH₃ partial structure in the side chain portion thereof, a form in which the hydrophobic resin does not substantially include a fluorine atom and a silicon atom is preferable. Further, it is preferable that the hydrophobic resin is constituted with substantially only repeating units which are constituted with only atoms selected from a carbon atom, an oxygen atom, a hydrogen atom, a nitrogen atom, and a sulfur atom.

The weight-average molecular weight of the hydrophobic resin in terms of standard polystyrene is preferably 1,000 to 100,000, and more preferably 1,000 to 50,000.

A total content of the residual monomers and/or oligomer components included in the hydrophobic resin is preferably 0.01% to 5% by mass, and more preferably 0.01% to 3% by mass. In addition, the dispersity (Mw/Mn) is preferably 1.0 to 5.0, and more preferably 1.0 to 3.0.

As the hydrophobic resin, known resins can be appropriately selected and used singly or as a mixture. For example, the known resins disclosed in paragraphs <0451> to <0704> of the specification of US2015/0168830A1 and paragraphs <0340> to <0356> of the specification of US2016/0274458A1 can be suitably used as the hydrophobic resin. In addition, the repeating units disclosed in paragraphs <0177> to <0258> of the specification of US2016/0237190A1 are also preferable as the repeating units constituting the hydrophobic resin.

Preferred examples of a monomer corresponding to the repeating unit constituting the hydrophobic resin are shown below.

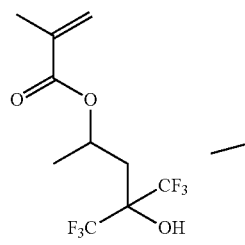
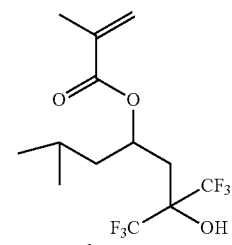
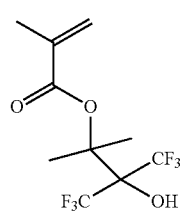
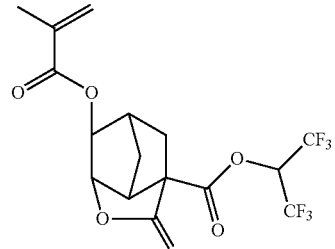
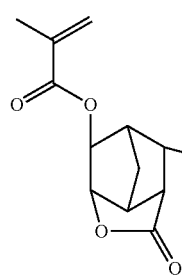
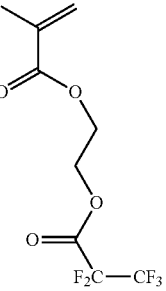

-continued

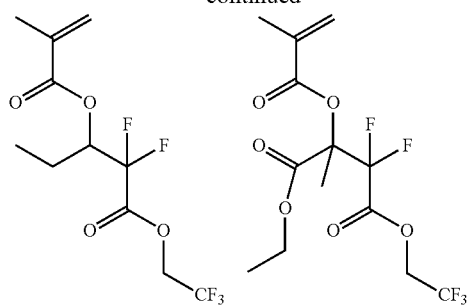
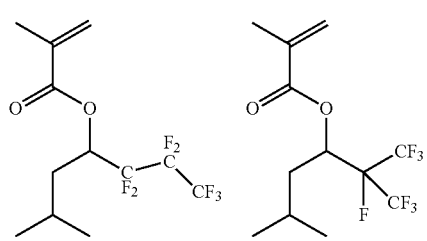
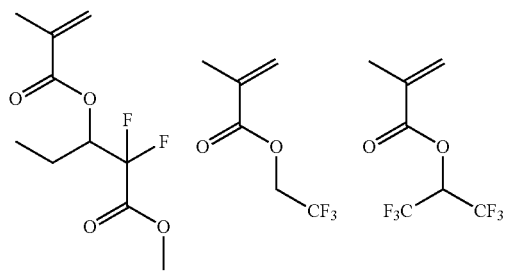
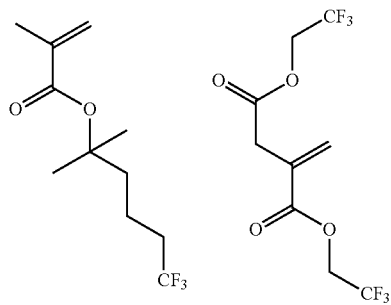
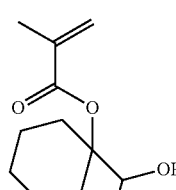
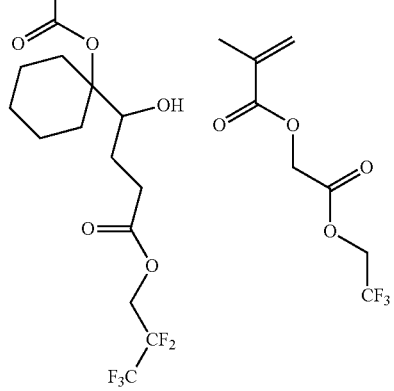

-continued

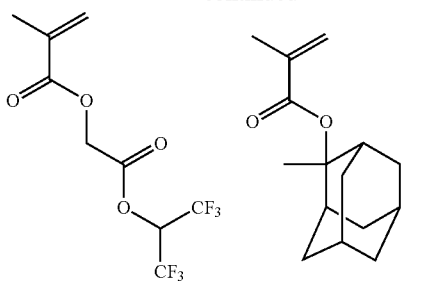
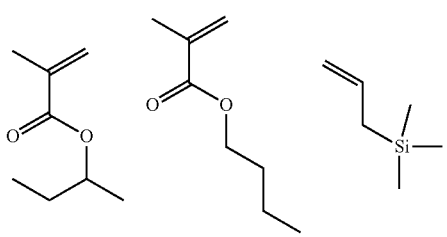
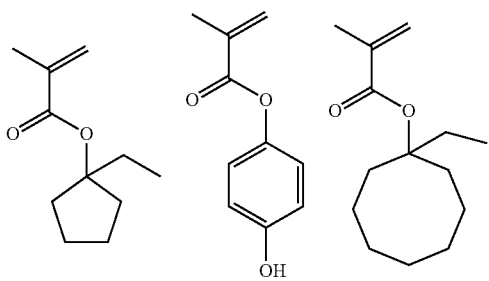
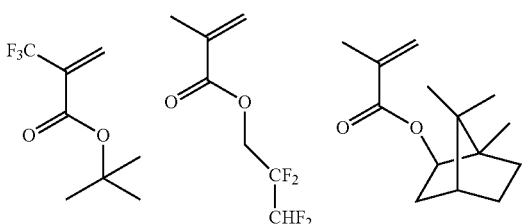
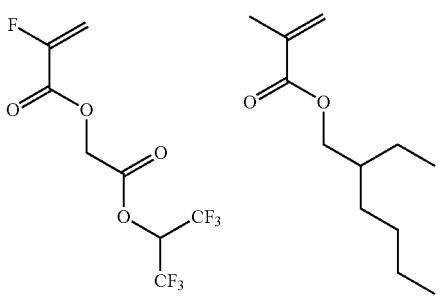
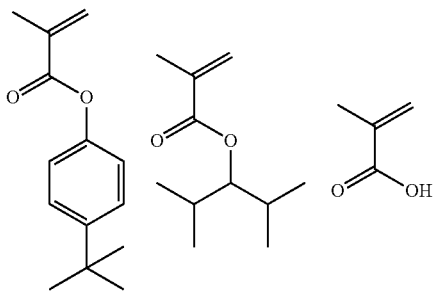

-continued

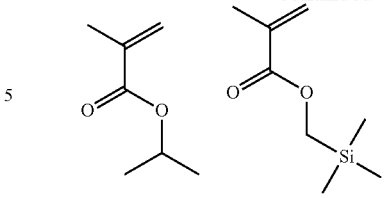

The hydrophobic resins may be used singly or in combination of two or more kinds thereof.

It is also preferable to use a mixture of two or more kinds of hydrophobic resins having different levels of surface energy from the viewpoint of satisfying both the immersion liquid tracking properties and the development characteristics upon liquid immersion exposure.

The content of the hydrophobic resin in the composition is preferably 0.01% to 10% by mass, more preferably 0.03% to 8.0% by mass, and still more preferably 0.10% to 1.0% by mass, with respect to the total solid content of the composition of the embodiment of the present invention. In a case where two or more kinds of hydrophobic resins are used, the total content thereof is preferably within the suitable content range.

<Solvent>

The composition of the embodiment of the present invention may include a solvent.

In the composition of the embodiment of the present invention, a known resist solvent can be appropriately used. For example, the known solvents disclosed in paragraphs <0665> to <0670> of the specification of US2016/0070167A1, paragraphs <0210> to <0235> of the specification of US2015/0004544A1, paragraphs <0424> to <0426> of the specification of US2016/0237190A1, and paragraphs <0357> to <0366> of the specification of US2016/0274458A1 can be suitably used.

Examples of the solvent which can be used in preparation of the composition include organic solvents such as alkylene glycol monoalkyl ether carboxylate, alkylene glycol monoalkyl ether, alkyl lactate ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

As the organic solvent, a mixed solvent obtained by mixing a solvent having a hydroxyl group in the structure and a solvent having no hydroxyl group may be used.

As the solvent having a hydroxyl group and the solvent having no hydroxyl group, the above-exemplified compounds can be appropriately selected, but as the solvent having a hydroxyl group, alkylene glycol monoalkyl ether or alkyl lactate is preferable, and propylene glycol monomethyl ether (PGME), propylene glycol monoethyl ether (PGEE), methyl 2-hydroxyisobutyrate, or ethyl lactate is more preferable. Further, as the solvent having no hydroxyl group, alkylene glycol monoalkyl ether acetate, alkyl alkoxypropionate, a monoketone compound which may have a ring, a cyclic lactone, alkyl acetate, or the like is preferable, and among these, propylene glycol monomethyl ether acetate (PGMEA), ethyl ethoxypropionate, 2-heptanone, γ-butyrolactone, cyclohexanone, cyclopentanone, or butyl acetate is more preferable, and propylene glycol monomethyl ether acetate, γ-butyrolactone, ethyl ethoxypropionate, cyclohexanone, cyclopentanone, or 2-heptanone is still more preferable. As a solvent having no hydroxyl group, propylene carbonate is also preferable.

A mixing ratio (mass ratio) of the solvent having a hydroxyl group to the solvent having no hydroxyl group is preferably 1/99 to 99/1, more preferably 10/90 to 90/10, and still more preferably 20/80 to 60/40. A mixed solvent including 50% by mass or more of the solvent having no hydroxyl group is preferable from the viewpoint of coating evenness.

It is preferable that the solvent includes propylene glycol monomethyl ether acetate. In this case, the solvent may be a single solvent of propylene glycol monomethyl ether acetate or a mixed solvent of two or more kinds including propylene glycol monomethyl ether acetate.

The concentration of the solid content in the composition of the embodiment of the present invention is preferably 1.0% to 10% by mass, more preferably 2.0% to 5.7% by mass, and still more preferably 2.0% to 5.3% by mass. That is, in a case where the composition includes a solvent, the content of the solvent in the composition is preferably adjusted so as to satisfy the suitable range of the concentration of the solid content. Furthermore, the concentration of the solid content is a mass percentage of other resist components excluding the solvent with respect to the total mass of the composition.

By setting the concentration of the solid content in the composition to an appropriate range to attain an appropriate viscosity and improving the coating property or the film-forming property, it is possible to adjust the film thickness of a resist film (actinic ray-sensitive or radiation-sensitive film) consisting of the composition of the embodiment of the present invention.

<Surfactant>

The composition of the embodiment of the present invention may include a surfactant.

The surfactant is preferably a fluorine-based and/or silicon-based surfactant (specifically a fluorine-based surfactant, a silicon-based surfactant, or a surfactant having both a fluorine atom and a silicon atom).

In a case where the composition of the embodiment of the present invention includes the surfactant, it is easy to obtain a pattern with good sensitivity and resolution and less adhesiveness and development defects in a case where an exposure light source of 250 nm or less, in particular, 220 nm or less is used.

Examples of the fluorine-based and/or silicon-based surfactants include the surfactants described in paragraph <0276> of the specification of US2008/0248425A.

In addition, another surfactant other than the fluorine-based and/or silicon-based surfactants described in paragraph <0280> of the specification of US2008/0248425A can also be used.

The surfactants may be used singly or in combination of two or more kinds thereof.

In a case where the composition of the embodiment of the present invention contains a surfactant, the content of the surfactant is preferably 0.0001% to 2% by mass, and more preferably 0.0005% to 1% by mass, with respect to the total solid content of the composition.

The surfactants may be used singly or in combination of two or more kinds thereof.

In a case where two or more kinds of the surfactants are used, the total content thereof is preferably within the suitable content range.

On the other hand, in a case where the content of the surfactant is 10 ppm by mass or more with respect to the total solid content of the composition, the uneven distribution of the hydrophobic resin on the surface is enhanced. As a result, the surface of the resist film can be made more hydrophobic, and the water following property during liquid immersion exposure is improved.

<Other Additives>

The composition of the embodiment of the present invention may further include a resin other than those described above, a crosslinking agent, an acid proliferation agent, a dye, a plasticizer, a photosensitizer, a light absorber, an alkali-soluble resin, a dissolution inhibitor, a dissolution accelerator, or the like.

<Preparation Method>

The composition of the embodiment of the present invention is preferably used by dissolving the components in a predetermined organic solvent (preferably the mixed solvent), and filtering the solution through a filter and applying it onto a predetermined support (substrate).

The pore size of a filter for use in filtration through the filter is preferably pore size of 0.1 μm or less, more preferably 0.05 m or less, and still more preferably 0.03 m or less. Further, in a case where the concentration of the solid content of the composition is high (for example, 25% by mass or more), the pore size of a filter used for filter filtration is preferably 3 μm or less, more preferably 0.5 μm or less, and still more preferably 0.3 m or less. As the filter, a polytetrafluoroethylene-made, polyethylene-made, or nylon-made filter is preferable. In the filtration through a filter as shown in the specification of JP2002-062667A, circulating filtration may be performed or the filtration may be performed by connecting plural kinds of filters in series or in parallel. In addition, the composition may be filtered in plural times. Furthermore, the composition may be subjected to a deaeration treatment or the like before or after filtration through a filter.

<Applications>

The composition of the embodiment of the present invention relates to an actinic ray-sensitive or radiation-sensitive resin composition whose properties change by undergoing a reaction upon irradiation with actinic rays or radiation. More specifically, the composition of the embodiment of the present invention relates to an actinic ray-sensitive or radiation-sensitive resin composition which is used in a step of manufacturing a semiconductor such as an integrated circuit (IC), for manufacture of a circuit board for a liquid crystal, a thermal head, or the like, the manufacture of a mold structure for imprinting, other photofabrication steps, or production of a planographic printing plate or an acid-curable composition. A pattern formed in the present invention can be used in an etching step, an ion implantation step, a bump electrode forming step, a rewiring forming step, microelectromechanical systems (MEMS), or the like.

[Pattern Forming Method and Resist Film]

The present invention also relates to a pattern forming method using the actinic ray-sensitive or radiation-sensitive resin composition. Hereinafter, the pattern forming method of the embodiment of the present invention will be described. Further, the resist film (actinic ray-sensitive or radiation-sensitive film) of the embodiment of the present invention will be described together with the description of the pattern forming method.

The pattern forming method of the embodiment of the present invention has:

(i) a step of forming a resist film (actinic ray-sensitive or radiation-sensitive film) on a support using the above-described actinic ray-sensitive or radiation-sensitive resin composition (resist film forming step (film forming step)), (ii) a step of exposing the resist film (irradiating the resist film with actinic rays or radiation) (exposing step), and (iii) a step of developing the exposed resist film with a developer (developing step).

The pattern forming method of the embodiment of the present invention is not particularly limited as long as it includes the steps (i) to (iii), and may further include the following steps.

In the pattern forming method of the embodiment of the present invention, the exposing method in the exposing step (ii) may be liquid immersion exposure.

The pattern forming method of the embodiment of the present invention preferably includes a prebaking (PB) step (iv) before the exposing step (ii).

The pattern forming method of the embodiment of the present invention preferably includes a post-exposure baking (PEB) step (v) after the exposing step (ii) and before the developing step (iii).

The pattern forming method of the embodiment of the present invention may include the exposing step (ii) a plurality of times.

The pattern forming method of the embodiment of the present invention may include the prebaking step (iv) a plurality of times.

The pattern forming method of the embodiment of the present invention may include the post-exposure baking step (v) a plurality of times.

In the pattern forming method of the embodiment of the present invention, the above-described resist film forming step (film forming step) (i), exposing step (ii), and developing step (iii) can be performed by a generally known method.

The thickness of the resist film is preferably 110 nm or less, and more preferably 95 nm or less, from the viewpoint of improving resolving power.

In addition, a resist underlayer film (for example, spin on glass (SOG), spin on carbon (SOC), and an antireflection film) may be formed between the resist film and the support, as desired. As a material constituting the resist underlayer film, known organic or inorganic materials can be appropriately used.

A protective film (topcoat) may be formed on the upper layer of the resist film. As the protective film, a known material can be appropriately used. For example, the compositions for forming a protective film disclosed in the specification of US2007/0178407A, the specification of US2008/0085466A, the specification of US2007/0275326A, the specification of US2016/0299432A, the specification of US2013/0244438A, or the specification of WO2016/157988A can be suitably used. The composition for forming a protective film preferably includes the above-described acid diffusion control agent.

A protective film may be formed on the upper layer of the resist film including the above-mentioned hydrophobic resin.

The support is not particularly limited, and a substrate which is generally used in a step of manufacturing a semiconductor such as an IC, and a step for manufacturing a circuit board for a liquid crystal, a thermal head, or the like, and other lithographic steps of photofabrication can be used. Specific examples of the support include an inorganic substrate such as silicon, $SiO_2$, and SiN.

For any of the prebaking step (iv) and the post-exposure baking step (v), the baking temperature is preferably 70° C. to 130° C., and more preferably 80° C. to 120° C.

For any of the prebaking step (iv) and the post-exposure baking step (v), the baking time is preferably 30 to 300 seconds, more preferably 30 to 180 seconds, and still more preferably 30 to 90 seconds.

The baking may be performed using a unit included in an exposing device and a developing device, and may also be performed using a hot plate or the like.

A light source wavelength used in the exposing step is not limited, and examples thereof include infrared rays, visible light, ultraviolet rays, far ultraviolet rays, extreme ultraviolet rays (EUV), X-rays, and electron beams. Among those, far ultraviolet rays are preferable, and a wavelength thereof is preferably 250 nm or less, more preferably 220 nm or less, and still more preferably 1 to 200 nm. Specifically, a KrF excimer laser (248 nm), an ArF excimer laser (193 nm), an $F_2$ excimer laser (157 nm), X-rays, EUV (13 nm), or electron beams are preferable, and the KrF excimer laser, the ArF excimer laser, EUV, or the electron beams are more preferable.

In the developing step (iii), the developer may be either an alkali developer or a developer including an organic solvent (hereinafter also referred to as an organic developer).

As the alkali developer, a quaternary ammonium salt typified by tetramethylammonium hydroxide is usually used, but in addition to this, an aqueous alkaline solution such as an inorganic alkali, primary to tertiary amines, an alcoholamine, and a cyclic amine can also be used.

Furthermore, the alkali developer may include an appropriate amount of alcohols and/or a surfactant. The alkali concentration of the alkali developer is usually 0.1% to 20% by mass. The pH of the alkali developer is usually 10 to 15.

A time period for performing development the using the alkali developer is usually 10 to 300 seconds.

The alkali concentration, the pH, and the development time using the alkali developer can be appropriately adjusted depending on a pattern formed.

The organic developer is preferably a developer including at least one organic solvent selected from the group consisting of a ketone-based solvent, an ester-based solvent, an alcohol-based solvent, an amide-based solvent, an ether-based solvent, and a hydrocarbon-based solvent.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, pentyl acetate, isopentyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butyrate, methyl 2-hydroxyisobutyrate, isoamyl acetate, isobutyl isobutyrate, and butyl propionate.

As the alcohol-based solvent, the amide-based solvent, the ether-based solvent, and the hydrocarbon-based solvent, the solvents disclosed in paragraphs <0715> to <0718> of the specification of US2016/0070167A1 can be used.

A plurality of the solvents may be mixed or the solvent may be used in admixture with a solvent other than those described above or water. The moisture content in the entire developer is preferably less than 50% by mass, more preferably less than 20% by mass, and still more preferably less than 10% by mass, and particularly preferably, moisture is not substantially included.

The content of the organic solvent with respect to the organic developer is preferably 50% to 100% by mass, more preferably 80% to 100% by mass, still more preferably 90% to 100% by mass, and particularly preferably 95% to 100% by mass, with respect to the total amount of the developer.

The developer may include an appropriate amount of a known surfactant, as desired.

The content of the surfactant is usually 0.001% to 5% by mass, preferably 0.005% to 2% by mass, and still more preferably 0.01% to 0.5% by mass, with respect to the total amount of the developer.

The organic developer may include the acid diffusion control agent.

Examples of the developing method include a method in which a substrate is dipped in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), and a method in which a developer is continuously jetted onto a substrate spun at a constant rate while scanning a developer jetting nozzle at a constant rate (a dynamic dispense method).

A combination of a step of performing development using an aqueous alkali solution (an alkali developing step) and a step of performing development using a developer including an organic solvent (an organic solvent developing step) may be used. Thus, a finer pattern can be formed since a pattern can be formed by keeping only a region with an intermediate exposure intensity from not being dissolved.

It is preferable that the method includes a step of performing washing using a rinsing liquid (a rinsing step) after the developing step (iii).

As the rinsing liquid used in the rinsing step after the developing step with an alkali developer, for example, pure water can be used. The pure water may include an appropriate amount of a surfactant. Moreover, after the developing step or the rinsing step, a treatment for removing the developer or the rinsing liquid adhering on a pattern by a supercritical fluid may be added. In addition, after the rinsing treatment or the treatment using a supercritical fluid, a heating treatment for removing moisture remaining in the pattern may be performed.

The rinsing liquid used in the rinsing step after the developing step with a developer including an organic solvent is not particularly limited as long as the rinsing liquid does not dissolve the pattern, and a solution including a common organic solvent, pure water, or the like can be used. As the rinsing liquid, a rinsing liquid including at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent include the same solvents as the solvents described for the developer including an organic solvent.

As the rinsing liquid used in the rinsing step in this case, a rinsing liquid including a monohydric alcohol is more preferable.

Here, examples of the monohydric alcohol used in the rinsing step include linear, branched, or cyclic monohydric alcohols. Specific examples thereof include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol, and methyl isobutyl carbinol.

The monohydric alcohol preferably has 5 or more carbon atoms, and examples thereof include 1-hexanol, 2-hexanol, 4-methyl-2-pentanol, 1-pentanol, 3-methyl-1-butanol, and methyl isobutyl carbinol.

The respective components in a plural number may be mixed or the components may also be used in admixture with an organic solvent other than the solvents.

A moisture content in the rinsing liquid used in the rinsing step after the developing step using the developer including the organic solvent is preferably 10% by mass or less, more preferably 5% by mass or less, and still more preferably 3% by mass or less. In a case where the moisture content is 10% by mass or less, good development characteristics are obtained.

The rinsing liquid after the developing step using the developer including the organic solvent may include an appropriate amount of the surfactant.

In the rinsing step, the developed substrate is subjected to a washing treatment using a rinsing liquid. A method for the washing treatment is not particularly limited, but examples thereof include a method in which a rinsing liquid is continuously jetted on a substrate rotated at a constant rate (a rotation application method), a method in which a substrate is dipped in a tank filled with a rinsing liquid for a certain period of time (a dip method), and a method in which a rinsing liquid is sprayed on a substrate surface (a spray method). Among those, a method in which a washing treatment is carried out using the rotation application method, and a substrate is rotated at a rotation speed of 2,000 to 4,000 rpm after washing, thereby removing the rinsing liquid from the substrate is preferable. Furthermore, it is also preferable that the method includes a baking step after the rinsing step (postbaking). The developer and the rinsing liquid remaining between and inside the patterns are removed by the baking step. In the baking step after the rinsing step, the baking temperature is usually 40° C. to 160° C., and preferably 70° C. to 95° C., and the baking time is usually 10 seconds to 3 minutes, and preferably 30 seconds to 90 seconds.

It is preferable that various materials (for example, a resist solvent, a developer, a rinsing liquid, a composition for forming an antireflection film, and a composition for forming a topcoat) used in the actinic ray-sensitive or radiation-sensitive resin composition of the embodiment of the present invention, and the pattern forming method of the embodiment of the present invention do not include impurities such as metal components, isomers, and residual monomers. The content of the impurities included in these materials is preferably 1 ppm by mass or less, more preferably 100 ppt by mass or less, and still more preferably 10 ppt by mass or less, and particularly preferably, the impurities are not substantially included (no higher than a detection limit of a measurement device).

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a polytetrafluoroethylene-made, polyethylene-made, or nylon-made filter is preferable. As the filter, a filter which has been washed with an organic solvent in advance may be used. In the step of filtration using a filter, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step. As the filter, a filter having a reduced amount of eluates as disclosed in the specification of JP2016-201426A is preferable.

In addition to the filtration using a filter, removal of impurities using an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used. Examples of the metal adsorbing material include the materials disclosed in the specification of JP2016-206500A.

In addition, examples of a method for reducing the impurities such as metals included in various materials include a method in which a raw material having a low metal content is selected as a raw material constituting various materials and the raw material constituting the various materials is subjected to filtration using a filter; and a method in which distillation under conditions suppressing contamination as much as possible by performing a lining with TEFLON (registered trademark), or the like in the inside of a device is performed. It is also preferable to carry out a glass lining treatment in all steps in a manufacturing facility for synthesizing various materials (a binder, PAG and the like) of the resist component in order to reduce metals to a ppt order. Preferred conditions in the filtration using a filter to be performed on the raw material constituting the various materials are the same as the above-described conditions.

In order to prevent impurities from being incorporated, it is preferable that various materials are stored in the container described in the specification of US2015/0227049A, the specification of JP2015-123351A, the specification of JP2017-013804A, or the like.

A method for improving the surface roughness of a pattern may be applied to a pattern formed by the pattern forming method of the embodiment of the present invention. Examples of the method for improving the surface roughness of a pattern include the method of treating a pattern by plasma of a hydrogen-containing gas, as disclosed in the specification of US2015/0104957A. In addition, known methods as described in the specification of JP2004-235468A, the specification of US2010/0020297A, and Proc. of SPIE Vol. 8328 83280N-1 "EUV Resist Curing Technique for LWR Reduction and Etch Selectivity Enhancement" may be applied.

In addition, a pattern formed by the method can be used as a core material (core) of the spacer process disclosed in, for example, the specification of JP1991-270227A (JP-H03-270227A) and the specification of US2013/0209941A.

[Method for Manufacturing Electronic Device]

Moreover, the present invention further relates to a method for manufacturing an electronic device, the method including the above-described pattern forming method. The electronic device manufactured by the method for manufacturing an electronic device of an embodiment of the present invention is suitably mounted on electric or electronic equipment (for example, home electronics, office automation (OA)-related equipment, media-related equipment, optical equipment, and telecommunication equipment).

Examples

Hereinbelow, the present invention will be described in more detail with reference to Examples. The materials, the amounts of materials used, the proportions, the treatment details, the treatment procedure, and the like shown in the Examples below may be modified as appropriate as long as the modifications do not depart from the spirit of the present invention. Therefore, the scope of the present invention should not be construed as being limited to the Examples shown below.

[Actinic Ray-Sensitive or Radiation-Sensitive Resin Composition]

[Components]

Components included in an actinic ray-sensitive or radiation-sensitive resin composition (hereinafter also referred to as a "composition") used in each of Examples or Comparative Examples are shown below.

<Acid-Decomposable Resin (Resin A)>

An acid-decomposable resin (resin A) used for producing the composition is shown below. In the following formulae, * represents a bonding position.

The number attached to the repeating unit of each resin indicates a molar fraction of each repeating unit.

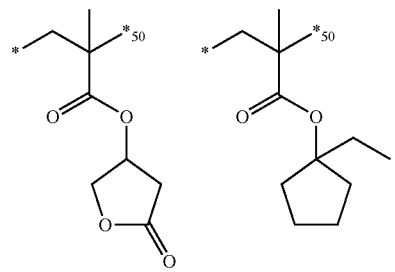

Mw = 7800
Mw/Mn = 1.64

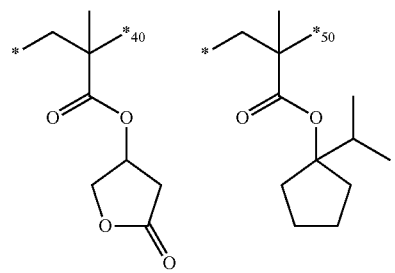

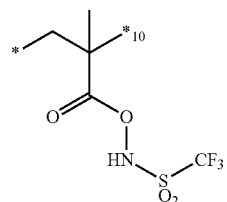

Mw = 8900
Mw/Mn = 1.52

-continued
P-3
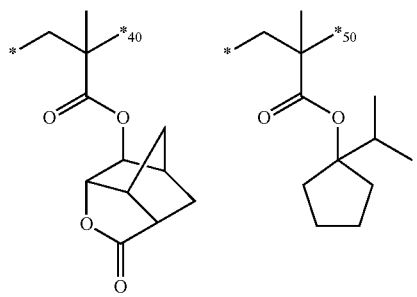
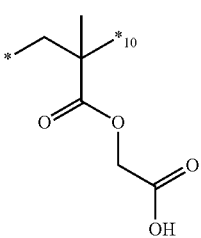
Mw = 8100
Mw/Mn = 1.56
P-4
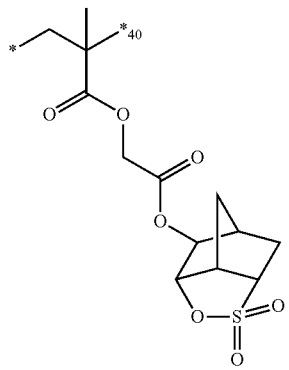
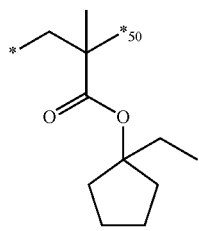
Mw = 6900
Mw/Mn = 1.55
P-5
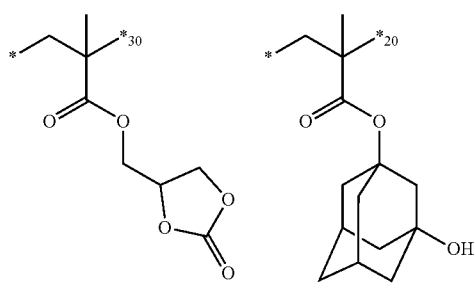
Mw = 7600
Mw/Mn = 1.61
-continued
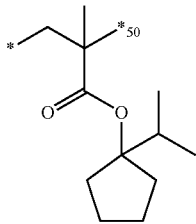
Mw = 7600
Mw/Mn = 1.61
P-6
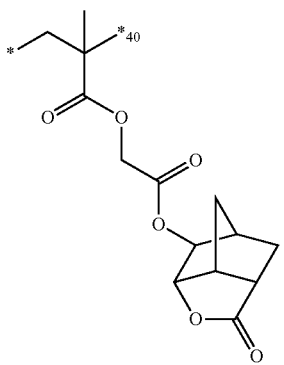 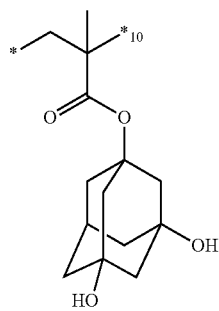
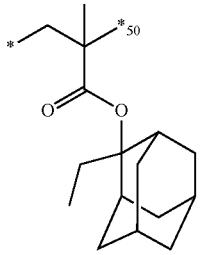
Mw = 9600
Mw/Mn = 1.69
P-7
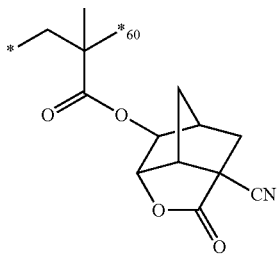 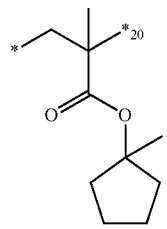
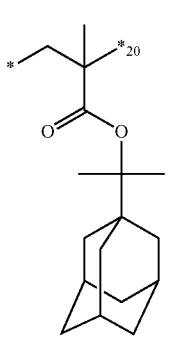
Mw = 7800
Mw/Mn = 1.21

-continued

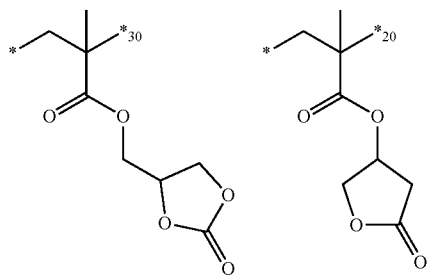

Mw = 5200
Mw/Mn = 1.57

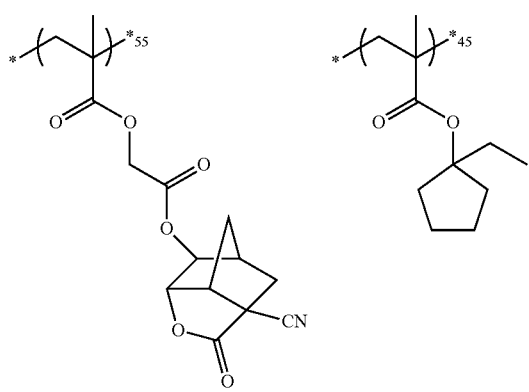

Mw = 11000
Mw/Mn = 1.30

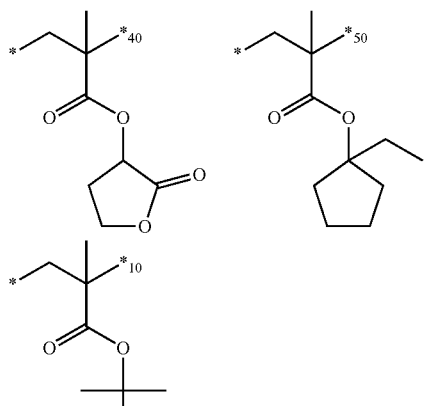

Mw = 8500
Mw/Mn = 1.86

<Photoacid Generators>

(PAG-1)

PAG-1 was synthesized according to the following scheme.

P-8

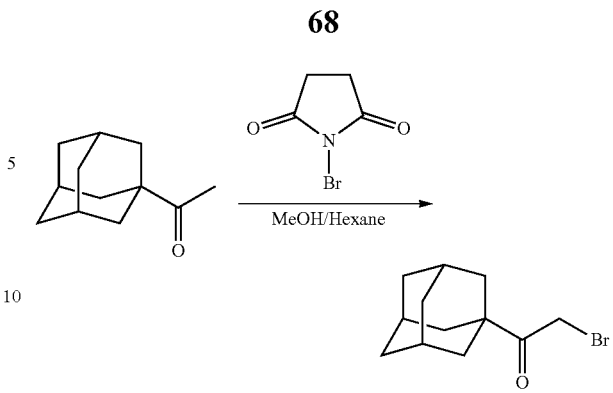

A mixed liquid prepared by mixing 1-acetyladamantane (75 g), N-bromosuccinimide (90 g), methanol (450 mL), and hexane (75 mL) was stirred at 60° C. for 2 hours. After cooling the mixed liquid to room temperature, the mixed liquid was filtered, the filtrate was recovered, and the solvent was evaporated. The obtained residue was recrystallized from ethanol to obtain 1-adamantyl bromomethyl ketone (70 g) as a white solid (yield 65%).

P-9

The results obtained by analyzing the obtained 1-adamantyl bromomethyl ketone (white solid) by a nuclear magnetic resonance (NMR) method were as follows.

$^1$H NMR (400 MHz, CDCl$_3$) δ 1.69-1.78 (m, 6H), 1.89 (s, 6H), 2.07 (s, 3H), 4.14 (s, 2H).

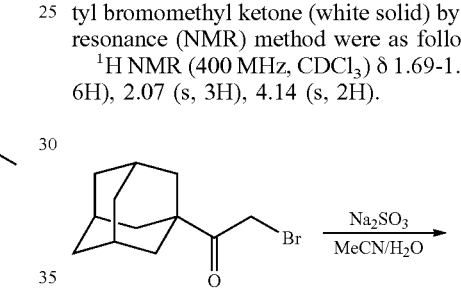

P-10

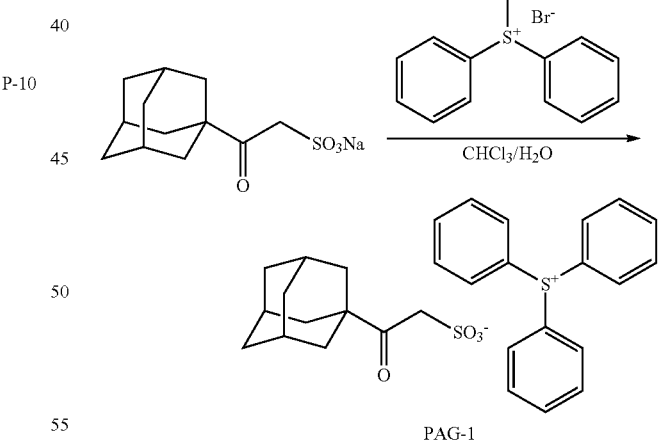

PAG-1

A mixed liquid prepared by mixing 1-adamantyl bromomethyl ketone (65 g), sodium sulfite (38.2 g), acetonitrile (200 mL), and water (130 mL) was stirred at 85° C. for 6 hours. The mixed liquid was transferred to a separating funnel, and the aqueous phase was washed twice with hexane to obtain an aqueous solution. Triphenylsulfonium bromide (60.8 g) and chloroform (130 mL) were added to the obtained aqueous solution to prepare a reaction solution, which was stirred for 1 hour. The reaction solution was transferred to a separating funnel and the organic phase was washed with water (65 mL) three times. The solvent was evaporated from the organic phase with an evaporator to obtain PAG-1 (92.1 g) which is a target compound, as a white solid (yield 70%).

The results obtained by analyzing the obtained PAG-1 (white solid) by the NMR method are as follows.

$^1$H NMR (400 MHz, CDCl$_3$) δ 1.63-1.71 (m, 6H), 1.87-1.88 (m, 6H), 2.00 (s, 3H), 4.10 (s, 2H), 7.65-7.74 (m, 9H), 7.84-7.86 (m, 6H).

(PAG-2 to PAG-6)

PAG-2 to PAG-6 and PAG-10 to PAG-20 were synthesized with reference to the method for synthesizing PAG-1.

Photoacid generators used for the preparation of the composition are shown below.

Among the following photoacid generators, PAG-1 to PAG-6 and PAG-10 to PAG-20 correspond to the photoacid generator A. PAG-7 to PAG-8 and PAG-21 to PAG-23 correspond to the photoacid generator B in relation to the photoacid generator A used in the present Example. PAG-9 corresponds to the photoacid generator D.

The pKa value attached to each photoacid generator indicates a pKa of an acid generated from the photoacid generator.

PAG-1

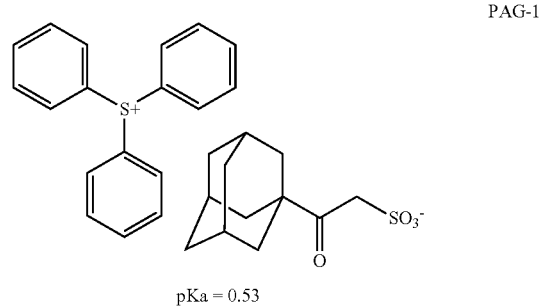

pKa = 0.53

PAG-2

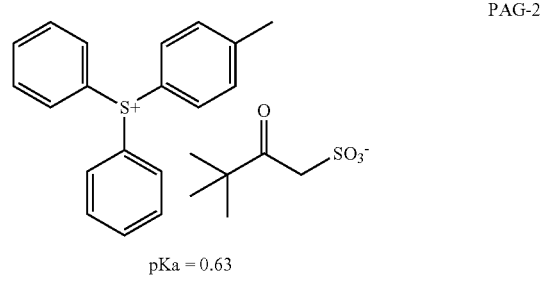

pKa = 0.63

PAG-3

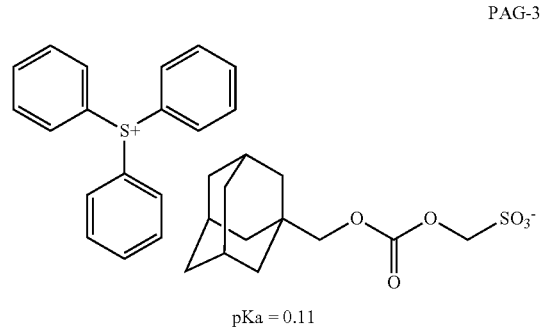

pKa = 0.11

PAG-4

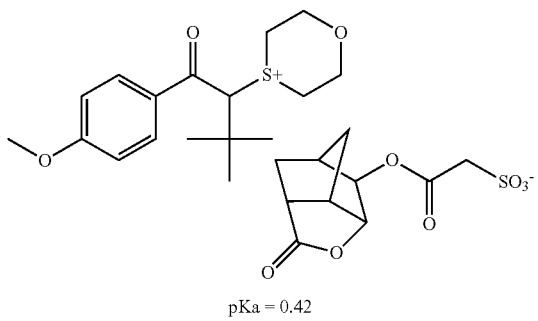

pKa = 0.42

PAG-5

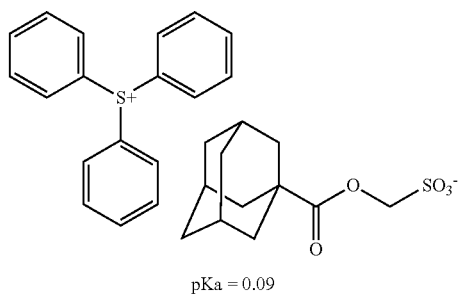

pKa = 0.09

PAG-6

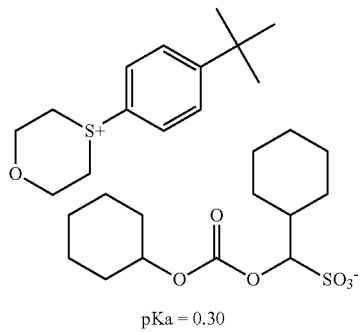

pKa = 0.30

PAG-7

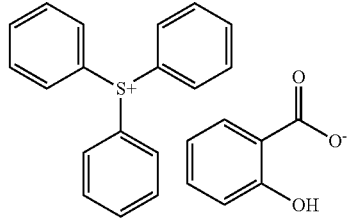

pKa = 3.01

PAG-8

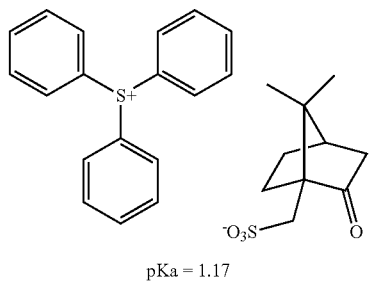

pKa = 1.17

-continued
PAG-9
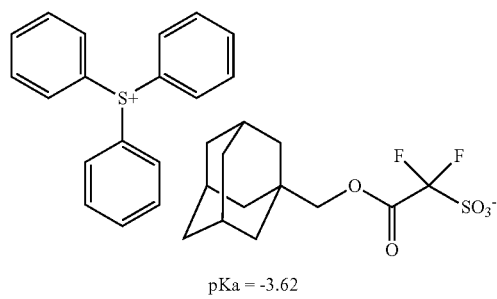
pKa = -3.62
PAG-10
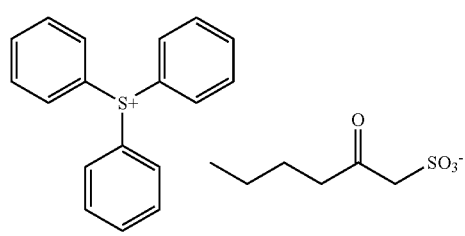
pKa = 0.53
PAG-11
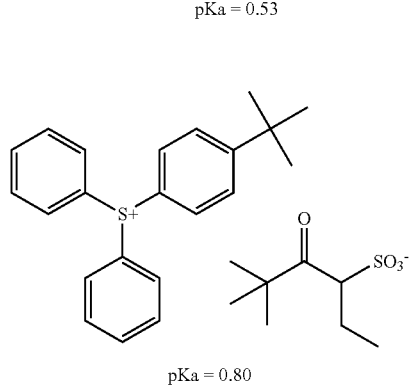
pKa = 0.80
PAG-12
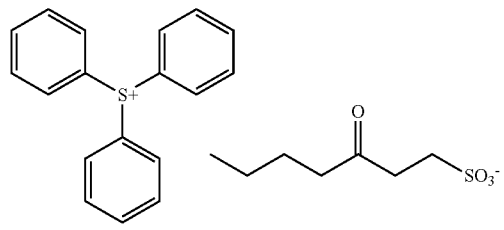
pKa = 1.36
PAG-13
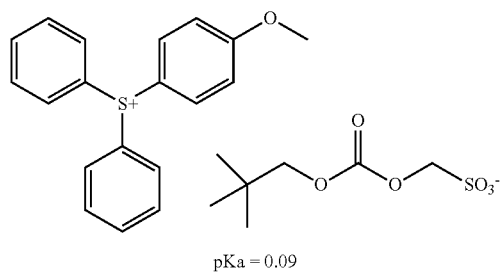
pKa = 0.09
-continued
PAG-14
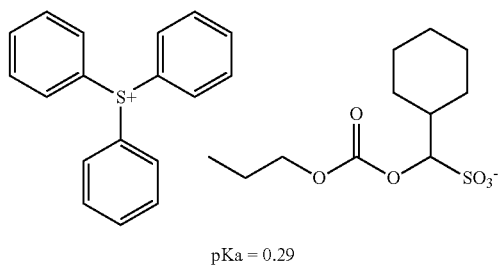
pKa = 0.29
PAG-15
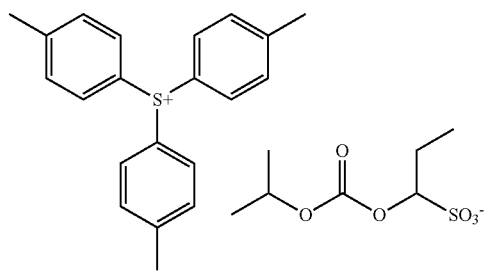
pKa = 0.35
PAG-16
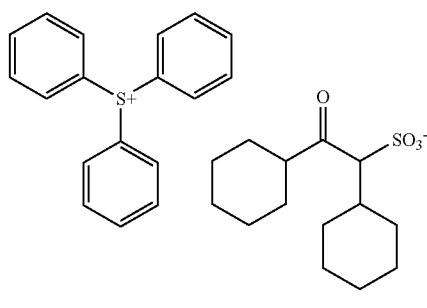
pKa = 0.72
PAG-17
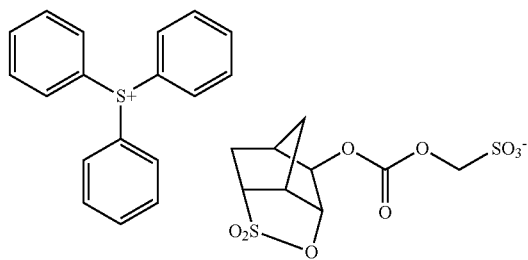
pKa = 0.04
PAG-18
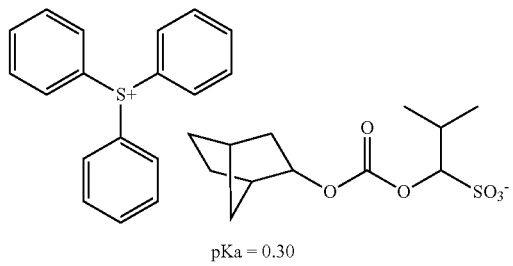
pKa = 0.30

-continued

PAG-19

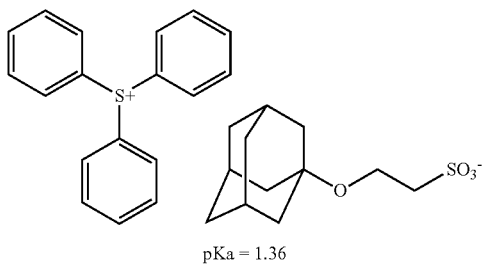

pKa = 1.36

PAG-20

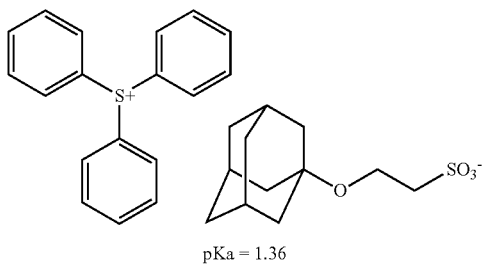

pKa = 0.87

PAG-21

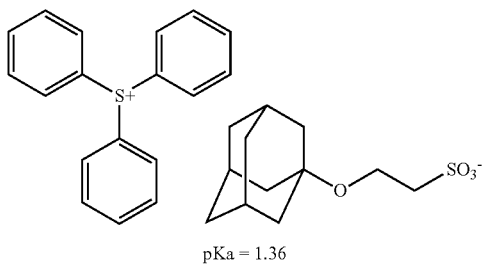

pKa = 11.55

PAG-22

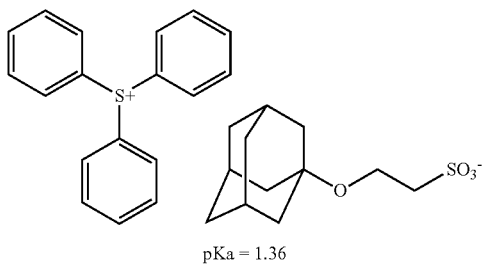

pKa = 4.18

PAG-23

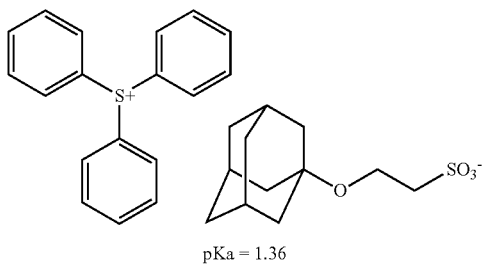

pKa = 1.53

<Nitrogen-Containing Compound>

A nitrogen-containing compound used to prepare the composition (nitrogen-containing compound C) is shown below.

The pKaH value attached to each nitrogen-containing compound indicates a pKa value of a conjugate acid of the nitrogen-containing compound.

Q-1

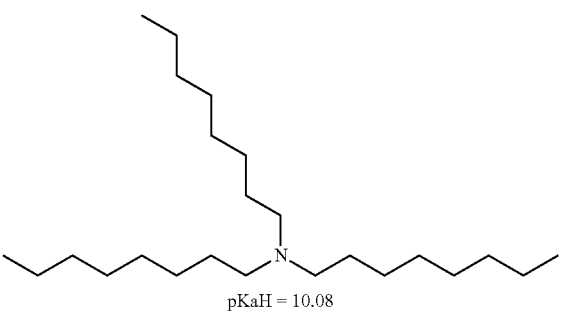

pKaH = 10.08

Q-2

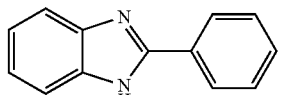

pKah = 11.72

Q-3

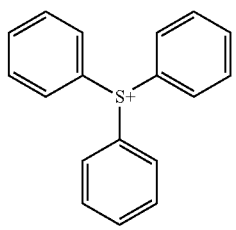

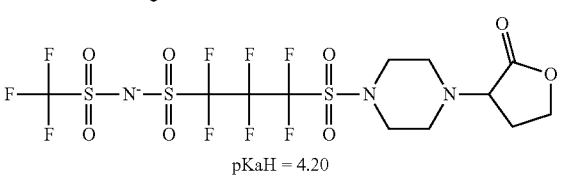

pKaH = 4.20

Q-4

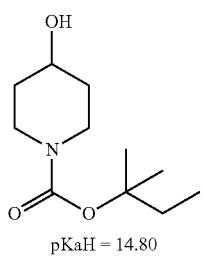

pKaH = 14.80

<Hydrophobic Resin>

A hydrophobic resins used to prepare the composition are shown below.

In the following formulae, * represents a bonding position.

The number attached to the repeating unit of each hydrophobic resin indicates a molar fraction of each repeating unit.

(1b)

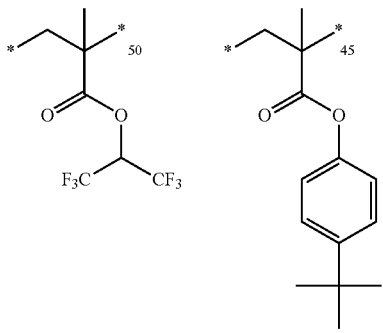

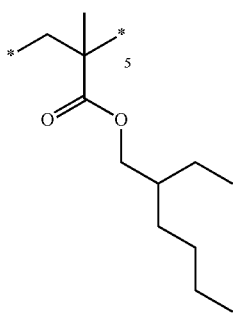

Mw = 7000
Mw/Mn = 1.30

(2b)

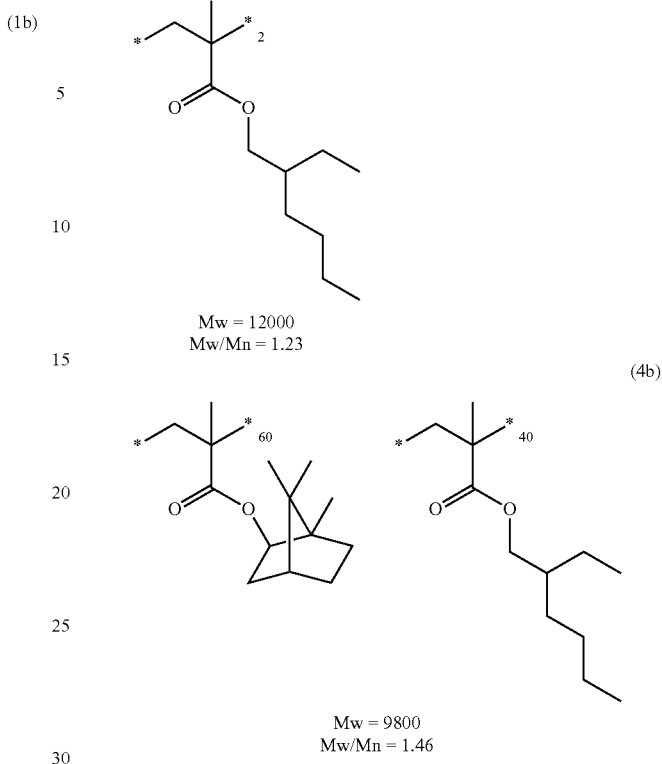

Mw = 18600
Mw/Mn = 1.57

(3b)

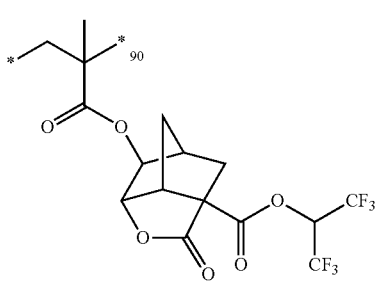

<Surfactant>
Solvents used to prepare the composition are shown below.
W-1: MEGAFACE F176 (manufactured by Dainippon Ink and Chemicals, Inc.; fluorine-based surfactant)
W-2: PolyFox PF-6320 (manufactured by OMNOVA Solutions Inc.; fluorine-based surfactant)
<Solvent>
Solvents used to prepare the composition are shown below.
SL-1: Propylene glycol monomethyl ether acetate (PGMEA)
SL-2: Propylene glycol monomethyl ether (PGME)
SL-3: Cyclohexanone
SL-4: γ-Butyrolactone

[Preparation of Composition]

The respective components shown in the tables in the next section were dissolved in a solvent so as to have the composition described in the tables in the section, thereby preparing a solution having a concentration of solid contents of 3.8% by mass. Then, the obtained solution was filtered through a polyethylene filter having a pore size of 0.1 m to prepare an actinic ray-sensitive or radiation-sensitive resin composition (composition). In addition, in the resist composition, the solid content means all the components excluding the solvent. The obtained resist composition was used in Examples and Comparative Examples.

[Evaluation]

<Pattern Formation>

A composition for forming an organic antireflection film ARC29SR (manufactured by Nissan Chemical Industries, Ltd.) was applied onto a silicon wafer and baked at 205° C. for 60 seconds to form an antireflection film having a film thickness of 95 nm. A resist composition was applied onto the obtained antireflection film and baked (PB: prebaking) at 100° C. for 60 seconds to form a resist film having a film thickness of 85 nm.

The obtained wafer was exposed through a 6% halftone mask having a 1:1 line-and-space pattern with a line width of 44 nm by using an ArF excimer laser liquid immersion scanner (XT1700i, manufactured by ASML, NA 1.20, C-Quad, outer sigma: 0.900, inner sigma: 0.812, XY deflection). Ultrapure water was used as the immersion liquid. Thereafter, the wafer was baked at 105° C. for 60 second (PEB: post-exposure baking).

Thereafter, in Examples 1 to 24 and Comparative Examples 1 to 3, development was performed by puddling with a negative developer (butyl acetate) for 30 seconds, and further rinsed with pure water to form a 1:1 line-and-space pattern with a line width of 44 nm (negative tone pattern).

In addition, in Examples 25 to 30 and Comparative Examples 4 and 5, development was performed with a positive developer (2.38%-by-mass aqueous tetraammonium hydroxide solution), and further rinsed with pure water to form a 1:1 line-and-space pattern with a line width of 44 nm (positive tone pattern).

<LWR Performance>

The obtained 1:1 line-and-space pattern with a line width of 44 nm was observed. In the observation of the pattern, the pattern was observed from the top with a critical dimension scanning electron microscope (SEM (S-9380II manufactured by Hitachi High Technologies Corporation)).

The line width at 50 points was measured at equal intervals in the range of 2 μm in the longitudinal direction of the line pattern, and 3a (nm) was calculated from the standard deviation thereof. The smaller the value, the better the LWR performance of the pattern.

[Results]

The formulation of the composition and the results of the evaluations performed using these compositions are shown in the following table.

In the column of "Solid content", the number described below each component name indicates the amount (g) of each component to be added. Further, in each composition, 10 g of a resin and 0.05 g of a hydrophobic resin are added, and in a case of adding a surfactant, 0.03 g of the surfactant is added.

In addition, in the composition of Example 13, the resins P-3 and P-6 are each added in an amount of 5 g, and the total amount thereof is 10 g. In the composition of Example 30, resins P-7 and P-9 are each added in an amount of 5 g, and the total amount thereof is 10 g.

In the table, the column of "Cyclic $R^3$" indicates whether or not the group corresponding to $R^3$ is an organic group including a ring structure in a case where an acid generated by a photoacid generator corresponding to the photoacid generator A in each composition is applied to General Formula (I). A case where the requirements were satisfied was described as A, and a case where the requirements were not satisfied was described as B.

The description of the numerical values in parentheses in the column of "Solvent" indicates a mixing ratio (mass ratio) of each solvent included in each composition.

The column of "A/D Molar ratio" means a ratio of the number of moles of the photoacid generator A to the number of moles of a photoacid generator D, each included in the composition in a case where the composition includes the photoacid generator D

TABLE 1

| | | Formulation ||||||||
| | | Solid content ||||||||
| | | Photoacid generator A ||| Photoacid generator B || Photoacid generator D || Nitrogen-containing compound C ||
| | | Type/content [g] | pKa | Cyclic $R^3$ | Type/content [g] | pKa | Type/content [g] | pKa | Type/content [g] | pKaH |
|---|---|---|---|---|---|---|---|---|---|---|
| Negative tone pattern formation | Example 1 | PAG-1 [1.55] | 0.53 | A | PAG-7 [0.36] | 3.01 | — | — | — | — |
| | Example 2 | PAG-2 [1.40] | 0.63 | B | PAG-7 [0.37] | 3.01 | — | — | — | — |
| | Example 3 | PAG-3 [1.70] | 0.11 | A | PAG-8 [0.44] | 1.17 | — | — | — | — |
| | Example 4 | PAG-4 [1.80] | 0.42 | A | — | — | — | — | Q-1 [0.35] | 10.08 |
| | Example 5 | PAG-5 [1.65] | 0.09 | A | — | — | — | — | Q-2 [0.17] | 11.72 |
| | Example 6 | PAG-6 [1.70] | 0.30 | A | — | — | — | — | Q-3 [0.80] | 4.20 |
| | Example 7 | PAG-3 [1.70] | 0.11 | A | PAG-7 [0.36] | 3.01 | — | — | — | — |
| | Example 8 | PAG-1 [1.56] | 0.53 | A | — | — | — | — | Q-3 [0.75] | 4.20 |
| | Example 9 | PAG-5 [1.65] | 0.09 | A | PAG-7 [0.36] | 3.01 | — | — | — | — |
| | Example 10 | PAG-4 [1.80] | 0.42 | A | PAG-7 [0.36] | 3.01 | — | — | — | — |
| | Example 11 | PAG-6 [1.10] | 0.30 | A | — | — | PAG-9 [0.62] | −3.62 | Q-3 [0.76] | 4.20 |
| | Example 12 | PAG-5 [0.85] | 0.09 | A | — | — | PAG-9 [0.88] | −3.62 | Q-1 [0.35] | 10.08 |
| | Example 13 | PAG-1 [1.55] | 0.53 | A | PAG-7 [0.36] | 3.01 | — | — | — | — |
| | Example 14 | PAG-10 [1.40] | 0.53 | B | PAG-21 [0.20] | 11.6 | — | — | — | — |

TABLE 1-continued

| | | | | | | | | | | |
|---|---|---|---|---|---|---|---|---|---|---|
| Example 15 | PAG-11 [1.55] | 0.80 | B | PAG-22 [0.36] | 4.18 | — | — | Q-3 [0.20] | 4.20 |
| Example 16 | PAG-12 [1.20] | 1.36 | B | PAG-7 [0.50] | 3.01 | — | — | — | — |
| Example 17 | PAG-13 [1.55] | 0.09 | B | — | — | — | — | Q-2 [0.35] | 11.72 |
| Example 18 | PAG-14 [1.55] | 0.29 | B | — | — | — | — | Q-4 [0.20] | 14.80 |
| Example 19 | PAG-15 [1.55] | 0.35 | B | — | — | — | — | Q-3 [0.20] | 4.20 |
| Example 20 | PAG-16 [1.55] | 0.72 | A | PAG-22 [0.30] | 4.18 | — | — | Q-2 [0.10] | 11.72 |
| Example 21 | PAG-17 [1.90] | 0.04 | A | PAG-7 [0.25] | 3.01 | PAG-9 [0.40] | −3.62 | — | — |
| Example 22 | PAG-18 [1.55] | 0.30 | A | PAG-12 [0.50] | 1.36 | — | — | — | — |
| Example 23 | PAG-19 [1.55] | 1.36 | A | — | — | PAG-9 [0.10] | −3.62 | Q-3 [0.15] | 4.20 |
| Example 24 | PAG-20 [1.55] | 0.87 | A | — | — | — | — | Q-3 [0.40] | 4.50 |
| Comparative Example 1 | PAG-1 [0.50] | 0.53 | A | — | — | PAG-9 [1.8] | −3.62 | — | — |
| Comparative Example 2 | — | — | A | — | — | PAG-9 [1.8] | −3.62 | Q-1 [0.35] | 10.08 |
| Comparative Example 3 | PAG-5 [0.66] | 0.09 | A | — | — | PAG-9 [1.05] | −3.62 | Q-1 [0.35] | 10.08 |

| | | | Formulation of composition | | | | | |
|---|---|---|---|---|---|---|---|---|
| | | | Solid content | | | | | |
| | | | Acid-decomposable resin [10 g] | Hydrophobic resin [0.05 g] | Surfactant [0.03 g] | Solvent (mass ratio) | A/D molar ratio | Evaluation LWR [nm] |
| Negative tone pattern formation | Example 1 | | P-3 | 1b | — | SL-1/SL-2 (80/20) | | 3.37 |
| | Example 2 | | P-3 | 1b | — | SL-1/SL-2 (80/20) | | 3.43 |
| | Example 3 | | P-1 | 1b | — | SL-1/SL-2/SL-4 (80/10/10) | | 3.36 |
| | Example 4 | | P-1 | 2b | — | SL-1/SL-3 (70/30) | | 3.41 |
| | Example 5 | | P-2 | 1b | — | SL-1/SL-2 (80/20) | | 3.38 |
| | Example 6 | | P-1 | 1b | W-1 | SL-1/SL-2 (80/20) | | 3.36 |
| | Example 7 | | P-5 | 1b | — | SL-1/SL-2/SL-4 (80/10/10) | | 3.35 |
| | Example 8 | | P-4 | 1b | — | SL-1/SL-2 (80/20) | | 3.37 |
| | Example 9 | | P-2 | 1b | — | SL-1/SL-2 (80/20) | | 3.37 |
| | Example 10 | | P-6 | 2b | — | SL-1/SL-3 (70/30) | | 3.41 |
| | Example 11 | | P-1 | 1b | W-1 | SL-1/SL-2 (80/20) | 1.9 | 3.42 |
| | Example 12 | | P-2 | 1b | — | SL-1/SL-2 (80/20) | 1.1 | 3.46 |
| | Example 13 | | P-3/P-6 [5 g/5 g] | 1b | W-2 | SL-1/SL-2 (80/20) | | 3.38 |
| | Example 14 | | P-7 | 3b | — | SL-1/SL-3 (70/30) | | 3.42 |
| | Example 15 | | P-10 | 1b | — | SL-1/SL-2 (80/20) | | 3.43 |
| | Example 16 | | P-1 | 1b | — | SL-1/SL-2 (80/20) | | 3.48 |
| | Example 17 | | P-1 | 1b | — | SL-1/SL-2 (80/20) | | 3.42 |
| | Example 18 | | P-1 | 1b | — | SL-1/SL-2/SL-4 (80/10/10) | | 3.44 |
| | Example 19 | | P-1 | 4b | — | SL-1/SL-3 (70/30) | | 3.43 |
| | Example 20 | | P-1 | 1b | — | SL-1/SL-3 (70/30) | | 3.32 |
| | Example 21 | | P-1 | 1b | — | SL-1/SL-2 (80/20) | 4.7 | 3.43 |
| | Example 22 | | P-1 | 1b | — | SL-1/SL-2 (80/20) | | 3.28 |

TABLE 1-continued

| | | | | | | |
|---|---|---|---|---|---|---|
| Example 23 | P-1 | 1b | — | SL-1/SL-2 (80/20) | 17.4 | 3.39 |
| Example 24 | P-1 | 1b | — | SL-1/SL-2 (80/20) | | 3.33 |
| Comparative Example 1 | P-4 | 1b | — | SL-1/SL-2 (80/20) | 0.3 | 3.74 |
| Comparative Example 2 | P-1 | 2b | — | SL-1/SL-3 (70/30) | | 3.79 |
| Comparative Example 3 | P-2 | 1b | — | SL-1/SL-2 (80/20) | 0.7 | 3.72 |

TABLE 2

| | | Formulation of composition ||||||||| 
| | | Solid content ||||||||| 
| | | Photoacid generator A ||| Photoacid generator B || Photoacid generator D || Nitrogen-containing compound C ||
| | | Type/ content [g] | pKa | Cyclic $R^3$ | Type/ content [g] | pKa | Type/ content [g] | pKa | Type/ content [g] | pKaH |
|---|---|---|---|---|---|---|---|---|---|---|
| Positive tone pattern formation | Example 25 | PAG-3 [1.90] | 0.11 | A | PAG-7 [0.30] | 3.01 | — | — | — | — |
| | Example 26 | PAG-6 [1.50] | 0.30 | A | PAG-23 [0.45] | 1.53 | — | — | — | — |
| | Example 27 | PAG-11 [1.60] | 0.80 | B | PAG-23 [0.50] | 1.53 | — | — | Q-4 [0.20] | 14.80 |
| | Example 28 | PAG-13 [1.55] | 0.09 | B | — | — | — | — | Q-3 [0.60] | 4.20 |
| | Example 29 | PAG-17 [2.00] | 0.04 | A | PAG-22 [0.30] | 4.18 | PAG-9 [0.15] | −3.62 | Q-3 [0.40] | 4.20 |
| | Example 30 | PAG-19 [1.15] | 1.36 | A | — | — | — | — | Q-4 [0.35] | 14.80 |
| | Comparative Example 4 | — | — | — | — | — | PAG-9 [1.50] | −3.62 | Q-4 [0.45] | 14.80 |
| | Comparative Example 5 | PAG-18 [0.50] | 0.30 | A | PAG-8 [0.40] | 1.17 | PAG-9 [1.00] | −3.62 | — | — |

| | | Formulation of composition ||||||
| | | Solid content |||| | |
| | | Acid-decomposable resin [10 g] | Hydrophobic resin [0.05 g] | Surfactant [0.03 g] | Solvent (mass ratio) | A/D molar ratio | Evaluation LWR [nm] |
|---|---|---|---|---|---|---|---|
| Positive tone pattern formation | Example 25 | P-7 | 3b | — | SL-1/SL-2/SL-4 (80/15/5) | | 3.30 |
| | Example 26 | P-8 | 3b | — | SL-1/SL-4 (90/10) | | 3.25 |
| | Example 27 | P-9 | 1b | — | SL-1/SL-2 (80/20) | | 3.42 |
| | Example 28 | P-10 | 1b | — | SL-1/SL-4 (90/10) | | 3.49 |
| | Example 29 | P-8 | 2b | — | SL-1/SL-4 (90/10) | 13.2 | 3.46 |
| | Example 30 | P-7/P-9 [5 g/5 g] | 3b | — | SL-1/SL-3 (70/30) | | 3.31 |
| | Comparative Example 4 | P-8 | 3b | — | SL-1/SL-2/SL-4 (80/15/5) | | 3.85 |
| | Comparative Example 5 | P-9 | 1b | — | SL-1/SL-4 (90/10) | 0.5 | 3.75 |

From the results shown in the tables, it was confirmed that it is possible to obtain a pattern having excellent LWR performance with the composition of the embodiment of the present invention.

It was also confirmed that in a case where the group corresponding to $R^3$ of an acid generated by the photoacid generator A was an organic group including a ring structure, the LWR of a pattern thus obtained was more excellent (Comparison between Examples 1 and 2, and the like).

It was confirmed that in a case where the composition includes the photoacid generator D, and the ratio of the number of moles of the photoacid generator A to the number of moles of the photoacid generator D in the composition (the content of the photoacid generator A/the content of the photoacid generator D (molar ratio)) is 1.5 times or more (more preferably 5 times or more), the LWR of a pattern thus obtained was more excellent (Comparison between Examples 11 and 12, and the like).

What is claimed is:

1. An actinic ray-sensitive or radiation-sensitive resin composition comprising:
   a photoacid generator A that generates an acid having a pKa of −1.00 or more;
   one or more selected from the group consisting of a photoacid generator B that generates an acid having a pKa larger than that of an acid generated from the photoacid generator A by 1.00 or more, and a nitrogen-containing compound C having a pKa of a conjugate acid thereof larger than that of the acid generated from the photoacid generator A by 1.00 or more; and
   an acid-decomposable resin,
   wherein the actinic ray-sensitive or radiation-sensitive resin composition may further include a photoacid generator D that is a compound different from the nitrogen-containing compound C and generates an acid having a pKa of less than −1.00, and
   in a case where the actinic ray-sensitive or radiation-sensitive resin composition includes the photoacid generator D, a ratio of the number of moles of the photoacid generator A to the number of moles of the photoacid generator D in the actinic ray-sensitive or radiation-sensitive resin composition, is 1.0 or more,
   wherein, the photoacid generator A is any one selected from the group consisting of PAG-4, PAG-6, PAG-11, PAG-14 to PAG-16, PAG-18 and PAG-20,

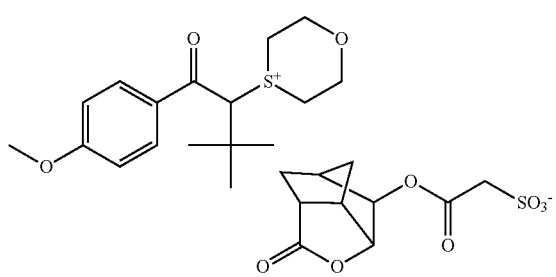

PAG-4
pKa = 0.42

-continued

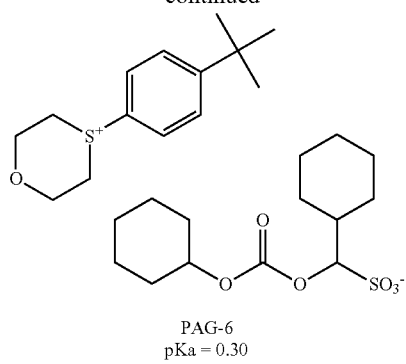

PAG-6
pKa = 0.30

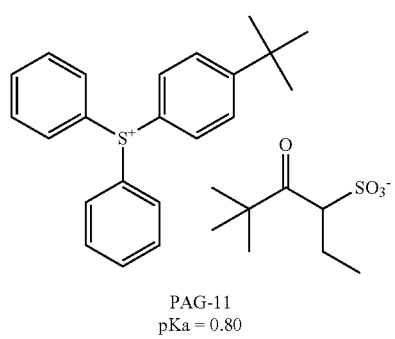

PAG-11
pKa = 0.80

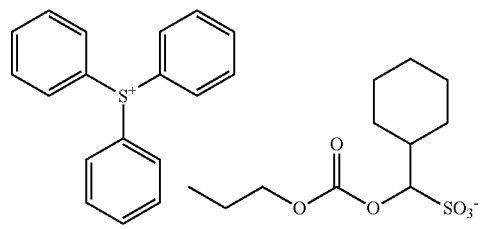

PAG-14
pKa = 0.29

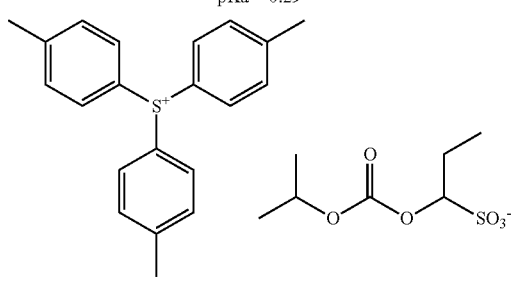

PAG-15
pKa = 0.35

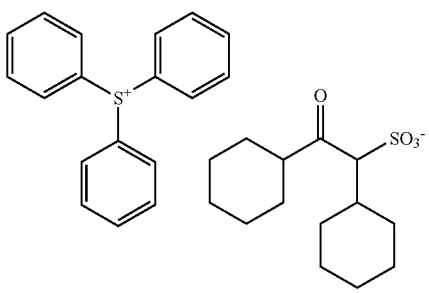

PAG-16
pKa = 0.72

-continued

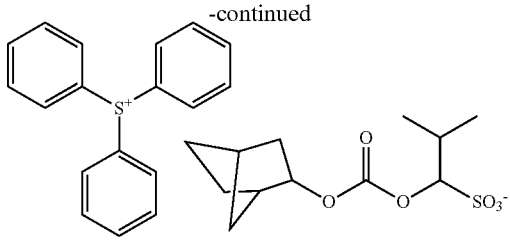

PAG-18
pKa = 0.30

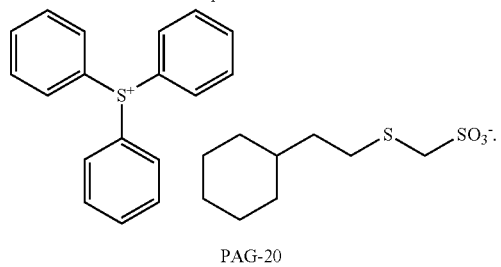

PAG-20
pKa = 0.87

2. The actinic ray-sensitive or radiation-sensitive resin composition according to claim 1,
wherein the acid-decomposable resin is a methacrylic ester-based resin.

3. A resist film formed from the actinic ray-sensitive or radiation-sensitive resin composition according to claim 1.

4. A pattern forming method comprising:
forming a resist film using the actinic ray-sensitive or radiation-sensitive resin composition according to claim 1 on a support;
exposing the resist film; and
developing the exposed resist film using a developer.

5. A method for manufacturing an electronic device, comprising the pattern forming method according to claim 4.

* * * * *